(12) United States Patent
Xiao et al.

(10) Patent No.: US 8,598,158 B2
(45) Date of Patent: Dec. 3, 2013

(54) FUSED TRICYCLIC COMPOUNDS FOR THE TREATMENT OF INFLAMMATORY DISORDERS

(75) Inventors: Dong Xiao, Warren, NJ (US); Anandan Palani, Bridgewater, NJ (US); Robert G. Aslanian, Rockaway, NJ (US); Sylvia Degrado, Scotch Plains, NJ (US); Xianhai Huang, Warren, NJ (US); Wei Zhou, Scotch Plains, NJ (US); Michael Sofolarides, Hoboken, NJ (US); Xiao Chen, Edison, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 13/515,638

(22) PCT Filed: Dec. 9, 2010

(86) PCT No.: PCT/US2010/059614
§ 371 (c)(1),
(2), (4) Date: Aug. 21, 2012

(87) PCT Pub. No.: WO2011/075375
PCT Pub. Date: Jun. 23, 2011

(65) Prior Publication Data
US 2012/0316154 A1    Dec. 13, 2012

Related U.S. Application Data

(60) Provisional application No. 61/286,164, filed on Dec. 14, 2009.

(51) Int. Cl.
C07D 417/02    (2006.01)
C07D 417/14    (2006.01)
A61K 31/55     (2006.01)
A61P 29/00     (2006.01)

(52) U.S. Cl.
USPC ..................... 514/212.06; 540/521

(58) Field of Classification Search
USPC ..................... 514/212.06; 540/521
See application file for complete search history.

(56) References Cited

U.S. PATENT DOCUMENTS

| | | | |
|---|---|---|---|
| 6,514,964 B1 * | 2/2003 | Chen et al. | 514/212.06 |
| 6,514,965 B1 | 2/2003 | Tomazic et al. | |
| 7,105,508 B1 | 9/2006 | Kling et al. | |
| 2007/0299050 A1 | 12/2007 | Lal et al. | |

FOREIGN PATENT DOCUMENTS

WO    WO00/73312 A1    12/2000
WO    WO02/45702 A2    6/2002

OTHER PUBLICATIONS

Int'l Search Report and Written Opinion for PCT/US2010/059614 mailed Feb. 2, 2011.
Xiao, D., et al. "Conformation constraint of anilides enabling the discovery of tricyclic lactams as potent MK2 non-ATP competitive inhibitors", Bioorganic & Medicinal Chemistry Letters 23 (2013), p. 3262-3266.
Supplemental European Search Report & Opinion, dated Apr. 12, 2013, for European Patent Application No. EP 2512238.

* cited by examiner

*Primary Examiner* — Bruck Kifle
(74) *Attorney, Agent, or Firm* — Eric A. Meade; Valerie J. Camara

(57) ABSTRACT

The present invention relates to certain lactam ring-containing compounds of the Formula (I) and pharmaceutically acceptable salts thereof, wherein D, E, $X^1$, $R^1$, $R^2$, $R^3$, $R^4$, $R^9$, and $R^{10}$ are as herein described. In addition, the invention relates to pharmaceutically acceptable compositions comprising at least one such compound, and methods of using the compounds for treating or preventing various inflammatory disorders such as rheumatoid arthritis, inflammatory bowel disease, psoriasis, asthma, and chronic obstructive pulmonary disorder.

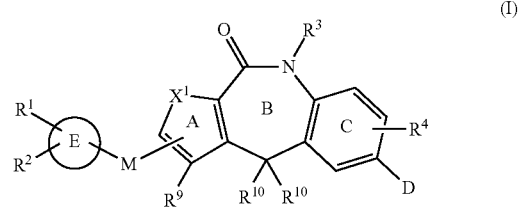

(I)

16 Claims, No Drawings

FUSED TRICYCLIC COMPOUNDS FOR THE TREATMENT OF INFLAMMATORY DISORDERS

CROSS REFERENCE TO RELATED APPLICATIONS

This application is a U.S. National Phase application under 35 U.S.C. §371 of PCT Application No. PCT/US2010/59614, filed Dec. 9, 2010, which claims priority under 35 U.S.C. §119(e) from U.S. Provisional Application Ser. No. 61/286,164, filed Dec. 14, 2009.

FIELD OF THE INVENTION

The present invention relates to certain lactam ring-containing compounds of the Formula (I) (also referred to as the "Fused Tricyclic Compounds"), compositions comprising at least one Fused Tricyclic Compound, and methods of using the Fused Tricylic Compounds for treating or preventing various inflammatory disorders such as rheumatoid arthritis, inflammatory bowel disease, psoriasis, asthma, and chronic obstructive pulmonary disease, or for treating cancer.

BACKGROUND OF THE INVENTION

Inflammatory conditions are often associated with inappropriate regulation of cytokines, which are proteins that affect cellular functions. Han et al., *Nature Cell Bial.*, E39-E40 (1999). Such inflammatory conditions include rheumatoid arthritis, inflammatory bowel disease, and psoriasis. Protein-based agents which antagonize cytokines such as antibodies or soluble receptors have recently been approved for therapy in certain chronic inflammatory diseases. Since such biologic agents must be administered to patients by injection, alternative therapies wherein anti-inflammatory agents are orally administered may be more convenient and desirable.

Strategies that involve modulating the activity of kinases involved in inflammatory regulatory pathways using small molecule inhibitors may provide alternative therapeutic approaches to treat inflammation. Kinases play a major role in the upregulation of major pro-inflammatory cytokines such as tumor necrosis factor alpha (TNF-α). One such kinase is mitogen-activated protein kinase-activated protein kinase 2 (MAPKAP K2 or MK2) which mediates multiple p38 MAPK-dependent cellular responses. MK2 is phosphorylated by p38 MAP kinase in response to certain environmental stress or inflammatory cytokines. Kotlyarov et al., *Nat. Cell Biol.*, 1: 94-97 (1999). Upon stimulation,. MK2 phosphorylates heat shock protein (HSP) 27, tyrosine hydroxylase, and leukocyte-specific protein-1 (LSPI), Duraisarny et al., *Expert Opin. Ther. Targets*, 12: 921-936 (2008).

Experimental observations support the prediction that inhibition of MK2 is an appropriate approach for treating inflammation. Kotlyarov et al. in *Nat. Cell Biol.*, 1: 94-97 (1999) showed that mice that lack MK2 function, due to a mutation in the mouse MK2 gene, show increased stress resistance and survive LPS-induced endotoxic shock. These obervations were explained by a reduced production of the pro-inflammatory cytokine TNF-α. Id. In addition, in an animal model of rheumatoid arthritis, deletion of the MK2 gene in mice conferred protection to the mice toward collagen-induced arthritis. Heger) et al., *J. Immunol.*, 177: 1913-1917 (2006).

Thus, due to MK2's involvement in inflammatory responses, it serves as a promising target for therapeutic intervention. Small molecule therapeutic agents that inhibit the activity of MK2 would be particularly useful for treating inflammatory conditions in humans and animals.

SUMMARY OF THE INVENTION

In one aspect, the present invention provides compounds of Formula (I) (herein referred to as the "Fused Tricyclic Compounds"):

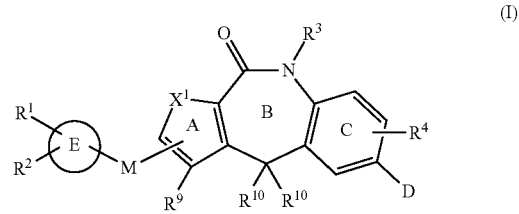

(I)

or a pharmaceutically acceptable salt thereof, wherein

E is phenyl, or is a monocyclic or bicyclic heteroaryl ring containing five to 10 ring atoms, wherein said heteroaryl ring contains from one to four heteroatoms selected from the group consisting of N, O, and S;

$R^1$ and $R^2$ are independently present or absent, and if present, are independently $(C_1-C_6)$alkyl, halo, $(C_1-C_6)$alkoxy, —CN, $(C_1-C_6)$ haloalkyl, azido, —C(=O)—$(C_1-C_6)$ alkyl, —S(O)—$(C_1-C_6)$alkyl, or —S(O)$_2$—$(C_1-C_6)$alkyl, amino, $(C_1-C_6)$alkylamino, di$(C_1-C_6)$alkylamino, carbamyl, —NH—C(=O)—$(C_1-C_6)$alkyl, or hydroxyl;

M is —O—, —S(O)—, —S(O)$_2$—, $(C_1-C_4)$alkylene, $(C_1-C_4)$alkenylene, $(C_1-C_4)$alkynylene, fluoro$(C_1-C_4)$alkylene, hydroxy$(C_1-C_4)$alkylene, or alkoxy$(C_1-C_4)$alkylene;

or M is absent, such that E is bonded directly to ring A;

$X^1$ is O or S;

$R^9$ is H, $(C_1-C_6)$alkyl, or halo;

each occurrence of $R^{10}$ is independently H, $(C_1-C_3)$alkyl, fluoro, $(C_1-C_3)$ fluoroalkyl, or $(C_1-C_3)$alkoxy;

$R^3$ is H, $(C_1-C_6)$ alkyl, $(C_1-C_6)$ haloalkyl, or $(C_1-C_6)$alkoxy $(C_1-C_6)$alkyl, or $R^3$ is a group of the formula -J-K, wherein J is $(C_1-C_3)$ alkylene, —C(=O)—, or —C(=S)—;

K is $(C_3-C_{10})$ cycloalkyl, $(C_6-C_{10})$ aryl, 5- to 6-membered heteroaryl, or 5- to 6-membered heterocyclyl, wherein said cycloalkyl, aryl, heteroaryl, or heterocyclyl of K is unsubstituted or substituted with one to four moieties, wherein said moieties are the same or different, and wherein said moieties are selected from the group consisting of $(C_1-C_6)$ alkyl, $(C_1-C_6)$ alkoxy, $(C_1-C_6)$ haloalkyl, halo, amino, $(C_1-C_6)$ alkylamino, di$(C_1-C_6)$ alkylamino, —CN, —OCF$_3$, and $R^{25}$;

$R^{25}$ is $(C_6-C_{10})$ aryl or 5- to 6-membered heteroaryl, wherein said aryl or heteroaryl of $R^{25}$ is unsubstituted or substituted with one to four moieties, wherein said moieties are selected from the group consisting of $(C_1-C_6)$ alkyl, hydroxyl, $(C_1-C_6)$ alkoxy, halo, amino, $(C_1-C_6)$ alkylamino, di$(C_1-C_6)$alkylamino, —CF$_3$, —OCF$_3$, or —CN;

$R^4$ is absent, halo, —CN, $(C_1-C_6)$ alkyl, or $(C_1-C_6)$ fluoroalkyl;

wherein D is a heterocyclic or heteroaryl ring selected from the group consisting of:

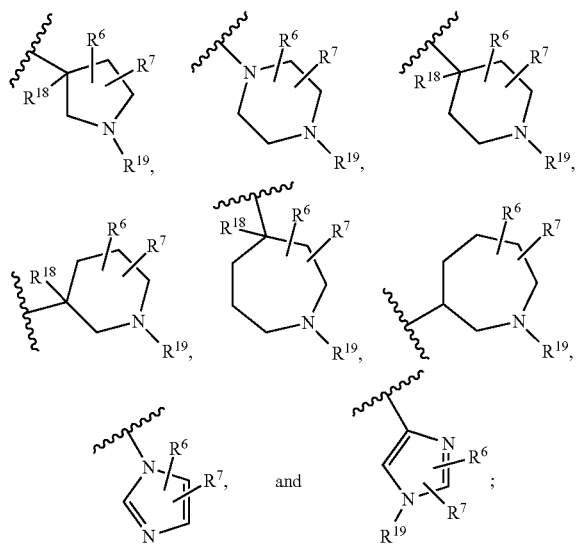

wherein $R^6$ and $R^7$ are independently absent or present, and if present, are independently $(C_1$-$C_3)$ alkyl, $(C_1$-$C_3)$ fluoroalkyl, —$CH_2$—O—$(C_1$-$C_3)$alkyl, —$CH_2CH_2$—O—$(C_1$-$C_3)$alkyl, or —$CH_2CH_2CH_2$—O—$(C_1$-$C_3)$ alkyl, and wherein $R^6$ and $R^7$ are substituted on a carbon atom;

$R^{18}$ is H, —CN, hydroxy, $(C_1$-$C_6)$ alkyl, or $(C_1$-$C_6)$ alkoxy; and $R^{19}$ is H or $(C_1$-$C_3)$ alkyl.

The invention also provides a method for treating an inflammatory disorder such as rheumatoid arthritis, inflammatory bowel disease, psoriasis; asthma, or chronic obstructive pulmonary disease, comprising administering a Fused Tricyclic Compound, or a pharmaceutically acceptable salt thereof, to a patient, e.g., a human patient, in need of such treatment.

The present invention further provides pharmaceutical compositions comprising an effective amount of at least one Fused Tricyclic Compound or a pharmaceutically acceptable salt thereof, and a pharmaceutically acceptable carrier. In some embodiments, the pharmaceutical compositions can be useful for treating an inflammatory disorder such as rheumatoid arthritis, inflammatory bowel disease, psoriasis, asthma, or chronic obstructive pulmonary disease in a patient in need of such treatment.

The details of the invention are set forth in the accompanying detailed description below.

Although any methods and materials similar to those described herein can be used in the practice or testing of the present invention, illustrative methods and materials are now described. Other features, objects, and advantages of the invention will be apparent from the description and the claims. All patents and publications cited in this specification are incorporated herein by reference.

DETAILED DESCRIPTION OF THE INVENTION

The present invention provides Fused Tricyclic Compounds, pharmaceutical compositions comprising at least one Fused Tricyclic Compound, and methods of using the Fused Tricyclic Compounds for treating various inflammatory disorders, such as rheumatoid arthritis, inflammatory bowel disease, psoriasis, asthma, and chronic obstructive pulmonary disease, or cancer in a patient, e.g., a human patient.

Definitions and Abbreviations

As used above, and throughout this disclosure, the following terms, unless otherwise indicated, shall be understood to have the following meanings:

"Patient" includes both human and animals.

"Mammal" means humans and other mammalian animals.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. "Alkyl" may be unsubstituted or optionally substituted by one or more substituents which may be the same or different, each substituent being independently selected from the group consisting of halo, aryl, cycloalkyl, cyano, hydroxy, alkoxy, alkylthio, amino, oxime (e.g., =N—OH), —NH(alkyl), —NH(cycloalkyl), —N(alkyl)$_2$, —O—C(O)-alkyl, —O—C(O)-aryl, —O—C(O)-cycloalkyl, —SF$_5$, carboxy and —C(O)O-alkyl. Non-limiting examples of suitable alkyl groups include methyl, ethyl, n-propyl, isopropyl and t-butyl.

"Alkylene" means a difunctional group obtained by removal of a hydrogen atom from an alkyl group that is defined above. Non-limiting examples of alkylene include methylene, ethylene and propylene. Unless otherwise indicated, an alkylene group is unsubstituted.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. "Alkenyl" may be unsubstituted or optionally substituted by one or more substituents which may be the same or different, each substituent being independently selected from the group consisting of halo, aryl, cycloalkyl, cyano, alkoxy and —S(alkyl). Non-limiting examples of suitable alkenyl groups include ethenyl, propenyl, n-butenyl, 3-methylbut-2-enyl, n-pentenyl, octenyl and decenyl. Unless otherwise indicated, an alkyl group is unsubstituted.

"Alkenylene" means a difunctional group obtained by removal of a hydrogen atom from an alkenyl group that is defined above. Unless otherwise indicated, an alkenylene group is unsubstituted.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and 3-methylbutynyl. The "alkynyl" may be unsubstituted or optionally substituted by one or more substituents which may be the same or different, each substituent being independently selected from the group consisting of aryl and cycloalkyl. Unless otherwise indicated, an alkynyl group is unsubstituted.

"Alkynylene" means a difunctional group obtained by removal of a hydrogen atom from an alkynyl group that is defined above. Unless otherwise indicated, an alkynylene group is unsubstituted.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl. Unless otherwise indicated, an aryl group is unsubstituted.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. In one embodiment, the heteroaryl contains from one to three heteroatoms selected from the group consisting of nitrogen, oxygen, and sulfur. Preferred heteroaryls contain about 5 to about 6 ring atoms. The "heteroaryl" can be optionally substituted by one or more "ring system substituents" which may be the same or different, and are as defined herein. The prefix aza, oxa or thin before the heteroaryl root name means that at least a nitrogen, oxygen or sulfur atom respectively, is present as a ring atom. A nitrogen atom of a heteroaryl can be optionally oxidized to the corresponding N-oxide. "Heteroaryl" may also include a heteroaryl as defined above fused to an aryl, as defined above. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like. Unless otherwise indicated, a heteroaryl group is unsubstituted.

"Aralkyl" or "arylalkyl" means an aryl-alkyl- group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like.

"Halogen" means fluorine, chlorine, bromine, or iodine. Preferred halogens are fluorine, chlorine and bromine.

"Haloalkyl" means an alkyl as defined above wherein one or more hydrogen atoms on the alkyl is replaced by a halogen group as defined above. Non-limiting examples of haloalkyl include trifluoromethyl, 2,2,2-trifluoroethyl, and 2-chloropropyl.

"Fluoroalkyl" means an alkyl as defined above wherein one or more hydrogen atoms on the alkyl is replaced by a fluorine. Non-limiting examples of fluoroalkyl include trifluoromethyl and 2,2,2-trifluoroethyl.

"Ring system substituent" means a substituent attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —SF$_5$, —OSF$_5$ (for aryl), —O—C(O)-alkyl, —O—C(O)-aryl, —O—C(O)-cycloalkyl, —(=N—CN)—NH$_2$, —C(=NH)—NH$_2$, —C(=NH)—NH(alkyl), oxime (e.g., =N—OH), —NY$_1$Y$_2$, -alkyl-NY$_1$Y$_2$, —C(C)NY$_1$Y$_2$, —SO$_2$NY$_1$Y$_2$ and —S(O)NY$_1$Y$_2$, wherein Y$_1$ and Y$_2$ can be the same or different and are independently selected from the group consisting of hydrogen, alkyl, aryl, cycloalkyl, and aralkyl. "Ring system substituent" may also mean a single moiety which simultaneously replaces two available hydrogens on two adjacent carbon atoms (one H on each carbon) on a ring system. Examples of such a moiety are methylene dioxy, ethylenedioxy, —C(CH$_3$)$_2$— and the like which form moieties such as, for example:

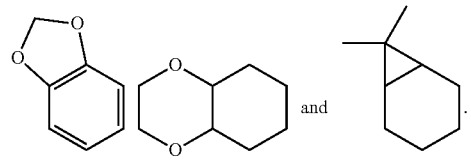

"Heteroarylalkyl" means a heteroaryl moiety as defined above linked via an alkyl moiety (defined above) to a parent core. Non-limiting examples of suitable heteroaryls include 2-pyridinylmethyl, quinolinylmethyl and the like.

"Heterocyclyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example, nitrogen, oxygen or sulfur, alone or in combination. There are no adjacent oxygen and/or sulfur atoms present in the ring system. In one embodiment, the heterocyclyl contains from one to three heteroatoms selected from the group consisting of nitrogen, oxygen, and sulfur. Preferred heterocyclyls contain about 5 to about 6 ring atoms. The prefix aza, oxa or thia before the heterocyclyl root name means that at least a nitrogen, oxygen or sulfur atom, respectively, is present as a ring atom. Any —NH in a heterocyclyl ring may exist in protected form such as, for example, as an —N(Boc), —N(CBz), —N(Tos) group and the like; such protections are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like. "Heterocyclyl" also includes heterocyclyl rings as described above wherein =O replaces two available hydrogens on the same ring carbon atom. An example of such a moiety is pyrrolidone:

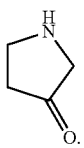

Unless otherwise indicated, a heterocyclyl is unsubstituted.

"Heterocyclylalkyl" means a heterocyclyl moiety as defined above linked via an alkyl moiety (defined above) to a parent core. Non-limiting examples of suitable heterocyclylalkyls include piperidinylmethyl, piperazinylmethyl and the like.

It should be noted that in hetero-atom containing ring systems of this invention, there are no hydroxyl groups on carbon atoms adjacent to a N, O or S, as well as there are no N or S groups on carbon adjacent to another heteroatom. Thus, for example, in the ring:

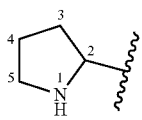

there is no —OH attached directly to carbons marked 2 and 5.

It should also be noted that tautomeric forms such as, for example, the moieties:

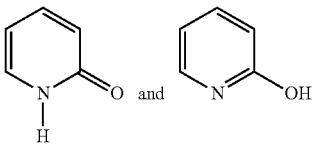 [SMILES: O=c1cccc[nH]1 ; "and" ; Oc1ccccn1]

are considered equivalent in certain embodiments of this invention.

"Hydroxyalkyl" means a HO-alkyl- group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1- naphthoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Alkylthio" means an alkyl-S— group in which the alkyl group is as previously described. Non-limiting examples of suitable alkylthio groups include methylthio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-S($O_2$)— group. Preferred groups are those in which the alkyl group is lower alkyl. The bond to the parent moiety is through the sulfonyl.

"Arylsulfonyl" means an aryl-S($O_2$)— group. The bond to the parent moiety is through the sulfonyl.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. A reference to a "stable compound" or "stable structure" means that the compound is sufficiently robust to survive isolation to a useful degree of purity from a reaction mixture, and to survive formulation into an efficacious therapeutic agent.

The term "optionally substituted" means optional substitution with the specified groups, radicals or moieties.

The term "purified", "in purified form" or "in isolated and purified form" for a compound refers to the physical state of said compound after being isolated from a synthetic process (e.g., from a reaction mixture), or natural source or combination thereof. Thus, the term "purified", "in purified form" or "in isolated and purified form" for a compound refers to the physical state of said compound after being obtained from a purification process or processes described herein or well known to the skilled artisan (e.g., chromatography, recrystallization and the like), in sufficient purity to be characterized by standard analytical techniques described herein or well known to the skilled artisan.

It should also be noted that any carbon as well as heteroatom with unsatisfied valences in the text, schemes, examples and Tables herein is assumed to have the sufficient number of hydrogen atom(s) to satisfy the valences. In addition, any one or more of these hydrogen atoms can be deuterium.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

When any variable (e.g., aryl, heterocycle, $R^2$, etc.) occurs more than one time in any constituent or in Formula (I), its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward. B. Roche, ed., American Pharmaceutical Association and Pergamon Press. The term "prodrug" means a compound (e.g., a drug precursor) that is transformed in vivo to yield a compound of Formula (I) or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of Formula (I) or a pharmaceutically acceptable salt, hydrate or solvate of the compound contains a carboxylic acid functional group, a prodrug can comprise an ester formed by the replacement of the hydrogen atom of the acid group with a group such as, for example, $(C_1-C_8)$alkyl, $(C_2-C_{12})$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N-$(C_1-C_2)$alkylamino$(C_2-C_3)$alkyl (such as β-dimethylaminoethyl), carbamoyl-$(C_1-C_2)$alkyl, N,N-di $(C_1-C_2)$alkylcarbamoyl-$(C_1-C_2)$alkyl and piperidino-, pyrrolidino- or morpholino$(C_2-C_3)$ alkyl, and the like.

Similarly, if a compound of Formula (I) contains an alcohol functional group, a prodrug can be formed by the replacement of the hydrogen atom of the alcohol group with a group such as, for example, $(C_1-C_6)$alkanoyloxymethyl, 1-(($C_1-C_6$)alkanoyloxy)ethyl, 1-methyl-1-(($C_1-C_6$)alkanoyloxy)ethyl, $(C_1-C_6)$alkoxycarbonyloxymethyl, N—$(C_1-C_6)$alkoxycarbonylaminomethyl, succinoyl, $(C_1-C_6)$alkanoyl, α-amino$(C_1-C_4)$alkanyl, arylacyl and α-aminoacyl, or α-aminoacyl-α-aminoacyl, where each α-aminoacyl group is independently selected from the naturally occurring L-amino acids, —P(O)(OH)$_2$, —P(O)(O($C_1-C_6$)alkyl)$_2$ or glycosyl (the radical resulting from the removal of a hydroxyl group of the hemiacetal form of a carbohydrate), and the like.

If a compound of Formula (I) incorporates an amine functional group, a prodrug can be formed by the replacement of a hydrogen atom in the amine group with a group such as, for example, R-carbonyl, RO-carbonyl, NRR'-carbonyl where R and R' are each independently $(C_1-C_{10})$alkyl, $(C_3-C_7)$cycloalkyl, benzyl, or R-carbonyl is a natural α-aminoacyl or natural α-aminoacyl, —C(OH)C(O)OY$^1$ wherein Y$^1$ is H, $(C_1-C_6)$alkyl or benzyl, —C(OY$^2$)Y$^3$ wherein Y$^2$ is $(C_1-C_4)$alkyl and Y$^3$ is $(C_1-C_6)$alkyl, carboxy $(C_1-C_6)$alkyl, amino $(C_1-C_4)$alkyl or mono-N— or di-N,N—$(C_1-C_6)$alkylaminoalkyl, —C(Y$^4$)Y$^5$ wherein Y$^4$ is H or methyl and Y$^5$ is mono-N— or di-N,N—$(C_1-C_6)$alkylamino morpholino, piperidin-1-yl or pyrrolidin-1-yl, and the like.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

One or more compounds of the invention may optionally be converted to a solvate. Preparation of solvates is generally known. Thus, for example, M. Caira et al, *J. Pharmaceutical Sci.*, 93(3), 601-611 (2004) describes the preparation of the solvates of the antifungal fluconazole in ethyl acetate as well as from water. Similar preparations of solvates, hemisolvate, hydrates and the like are described by E. C. van Tonder et al, *AAPS PharmSeiTech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

"Effective amount" or "therapeutically effective amount" is meant to describe an amount of compound or a composition of the present invention effective in inhibiting the above-noted diseases and thus producing the desired therapeutic, ameliorative, inhibitory or preventative effect.

The compounds of Formula (I) can form salts which are also within the scope of this invention. Reference to a compound of Formula (I) or a Fused Tricyclic Compound herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula (I) contains both a basic moiety, such as, but not limited to a pyridine or imidazole, and an acidic moiety, such as, but not limited to a carboxylic acid, zwitterions ("inner salts") may be formed and are included within the term "salt(s)" as used herein. All such acidic and basic salts intended to be used within the scope of the invention are pharmaceutically acceptable (i.e., non-toxic, physiologically acceptable) salts. Salts of the compounds of the Formula (I) may be formed, for example, by reacting a compound of Formula (I) with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quartemized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

Pharmaceutically acceptable esters of the present compounds include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_1$-$C_4$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di ($C_{6-24}$)acyl glycerol.

The compounds of Formula (I), and salts thereof, may exist in their tautomeric form (for example, as an amide or imino ether). All such tautomeric forms are contemplated herein as part of the present invention.

The compounds of Formula (I) may contain asymmetric or chiral centers, and, therefore, exist in different stereoisomeric forms.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula (I) may be atropisomers (e.g., substituted biaryls) and are considered as part of this invention. Enantiomers can also be separated by use of chiral HPLC column.

It is also possible that the compounds of Formula (I) may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). For example, if a compound of Formula (I) incorporates a double bond or a fused ring, both the cis- and trans-forms, as well as mixtures, are embraced within the scope of the invention. Also, for example, all keto-enol and imine-enamine forms of the compounds are included in the invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, sulfur, fluorine and chlorine and iodine, such as $^2$H, $^3$H, $^{11}$C, $^{13}$C, $^{14}$C, $^{15}$N, $^{18}$O, $^{17}$O, $^{31}$P, $^{32}$P, $^{35}$S, $^{18}$F, $^{36}$Cl and $^{123}$I, respectively.

Certain isotopically-labelled compounds of Formula (I) (e.g., those labeled with $^3$H and $^{14}$C) are useful in compound and/or substrate tissue distribution assays. Tritiated (i.e., $^3$H) and carbon-14 (i.e., $^{14}$C) isotopes are particularly preferred for their ease of preparation and detectability. Certain isotopically-labelled compounds of Formula (I) can be useful for medical imaging purposes. For instance those compounds labeled with positron-emitting isotopes like $^{11}$C or $^{18}$F can be useful for application in Positron Emission Tomography (PET) and those labeled with gamma ray emitting isotopes like $^{123}$I can be useful for application in Single Photon Emission Computed Tomography (SPECT). Further, substitution of compounds with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Additionally, isotopic substitution of a compound at a site where epimerization occurs may slow or reduce the epimerization process and thereby retain the more active or efficacious form of the compound for a longer period of time. Isotopically labeled compounds of Formula (I), in particular those containing isotopes with longer half lives (T1/2 >1 day), can generally be prepared by following procedures analogous to those disclosed in the Schemes and/or in the Examples herein below, by substituting an appropriate isotopically labeled reagent for a non-isotopically labeled reagent.

Polymorphic forms of the compounds of Formula (I), and of the salts, solvates, esters and prodrugs of the compounds of Formula (I), are intended to be included in the present invention.

The present invention further includes the compounds of Formula (I) in all their isolated forms. For example, the above-identified compounds are intended to encompass all forms of the compounds such as, any solvates, hydrates, stereoisomers, and tautomers thereof.

The compounds according to the invention have pharmacological properties; in particular, the compounds of Formula (I) can be inhibitors of MK2.

The following abbreviations are used below and have the following meanings: BINAP is racemic-2,2'-bis(diphenylphosphino)-1,1'-binaphthyl; BOC or Boc is tert-butyloxycarbonyl; CDI is carbonyl diimidazole; Ci/mmol is Curie/mmol; CSA is camphorsulfonic acid; DBPD is 2-(Di-t-butylphosphino)biphenyl, DBU is 1,8-diazabicyclo[5.4.0]undec-7-ene; DBN is 1,5-diazabicyclo[4.3.0]non-5-ene; DCC is dicyclohexylcarbodiimide; DCM is dichloromethane; Dibal-H is diisobutylaiuminum hydride; DIPEA is N,N-Diisopropylethylamine; DMAP is dimethylaminopyridine; DME is dimethoxyethane; DMF is dimethylformamide; DMPU is N,N'-Dim ethylpropyleneurea; dppf is diphenylphosphinoferrocene; EDCI is 1-(3-dimethylaminopropyl)-3- ethylcarbodiimide; EtOAc is ethyl acetate; FABMS is fast atom bombardment mass spectrometry; HATU is O-(7-azabenzotriazol-1-yl)-N,N,N',N'-tetramethyluronium hexafluorophosphate; HOBT is 1-hydroxybenzotriazole; HOOBt is 3-hydroxy-1,2,3-benzotriazin-4(3H)-one; HPLC is high performance liquid chromatography; HRMS is high resolution mass spectrometry; Hunig's base is N,N-diisopropylethylamine; LAH is lithium aluminum hydride; LDA is lithium diisopropylamide; LRMS is low resolution mass spectrometry; m-CPBA is m-chloroperbenzoic acid; MeOH is methanol; NaBH(OAc)$_3$ is sodium triacetoxyborohydride; NaHMDS is sodium hexamethyldisilazane; NH$_4$OAc is ammonium acetate; p-TsOH is p-toluenesulfonic acid; p-TsCl is p-toluenesulfonyl chloride; PPTS is pyridinium p-toluenesulfonate; PYBROP is bromotripyrrolidinophosphonium hexafluorophosphate; RT is room temperature; SEM is β-(trimethylsilyl)ethoxy]methyl; SEMCl is β-(trimethylsilyl)ethoxy]methyl chloride; TFA is trifluoroacetic acid; THF is tetrahydrofuran; TLC is thin-layer chromatography; TMAD is N,N,N',N'-tetramethylazodicarboxamide; Tr is triphenylmethyl; and Tris is tris(hydroxymethyl)aminoinethane.

The Compounds of Formula (I)

In one aspect, the present invention provides compounds of Formula (I):

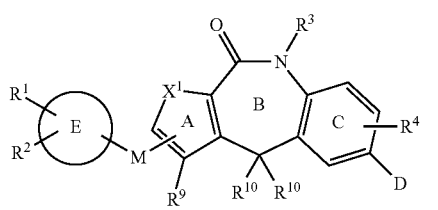

(I)

or pharmaceutically acceptable salts thereof, wherein D, E, X$^1$, R$^1$, R$^2$, R$^3$, R$^4$, R$^9$, and R$^{10}$ are as defined above for the compounds of Formula (I).

Ring A in Formula (I) is the five-membered ring which includes X$^1$ as a ring atom. Ring B in Formula (I) is the central azepinone ring. Ring C in Formula (I) is the phenyl ring fused to the central azepinone ring (Ring B).

In specific embodiments, the compounds of Formula (I) are in the form of pharmaceutically acceptable salts. In other specific embodiments, the compounds of Formula (I) are not formed into salts.

In certain embodiments, the compounds of Formula (I) are in purified form.

In some embodiments of the compounds of Formula (I), M is absent such that ring E is bonded directly to ring A.

In certain embodiments of the compounds of Formula (I), X$^1$ is O.

In certain embodiments of the compounds of Formula (I), R$^4$ is absent.

In some embodiments of the compounds of Formula (I), D is

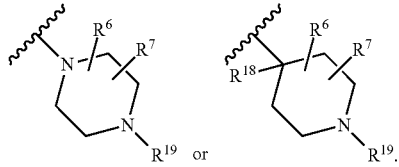

In specific instances, in the D ring, R$^6$ and R$^7$ are absent and R$^{18}$ and R$^{19}$ are H.

In specific embodiments of the compounds of Formula (I), E is phenyl, or a 5 to 6-membered heteroaryl ring. Generally, the 5- to 6-membered heteroaryl ring of E contains 1 to 3 heteroatoms selected from the group consisting of N, O, and S.

In certain embodiments of the compounds of Formula (I), R$^{18}$ and R$^{19}$ are H.

In some embodiments of the compounds of Formula (I), R$^3$ is —CH$_2$—K, wherein K is 3- to 6-membered cycloalkyl, phenyl, 5- to 6-membered monocyclic heteroaryl having from one to three heteroatoms selected from N, O, and S, or 3- to 8-membered monocyclic heterocyclyl having from one to two heteroatoms selected from N, O, and S, wherein said cycloalkyl, phenyl, heteroaryl, or heterocyclyl of K is unsubstituted or substituted with one to four moieties, wherein said moieties are the same or different, and wherein said moieties are selected from the group consisting of (C$_1$-C$_6$) alkyl, (C$_1$-C$_6$) alkoxy, (C$_1$-C$_6$) fluoroalkyl, halo, amino, (C$_1$-C$_6$) alkylamino, di(C$_1$-C$_6$)alkylamino, —CN, —OCF$_3$, and R$^{25}$.

In specific embodiments of the compounds of Formula (I), R$^3$ is —CH$_2$—K, wherein K is phenyl or 5- to 6-membered monocyclic heteroaryl having from one to three heteroatoms selected from N, O, and S, wherein said phenyl or heteroaryl of K is substituted by R$^{25}$, wherein R$^{25}$ is phenyl or a 5- to 6-membered heteroaryl ring having from one three heteroatoms selected from N, O, and S, wherein said phenyl or 5- to 6-membered heteroaryl ring is unsubstituted or substituted with (C$_1$-C$_6$) alkoxy, halo, or amino.

In another aspect, the present invention provides compounds of the Formula (Ia):

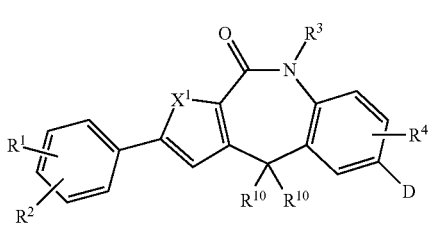

(Ia)

or pharmaceutically acceptable salts thereof, wherein $R^1$ and $R^2$ are independently absent or present, and if present are independently halo, $(C_1-C_6)$ alkoxy, —CN, $(C_1-C_6)$ haloalkyl, azido, acetyl, propionyl, butanoyl, —S(O)—$(C_1-C_4)$alkyl, or —S(O)$_2$—$(C_1-C_4)$alkyl;

$X^1$ is O or S;

each occurrence of $R^{10}$ is independently H, $(C_1-C_3)$ alkyl, fluoro, $(C_1-C_3)$ fluoroalkyl, or $(C_1-C_3)$ alkoxy;

$R^3$ is H, $(C_1-C_6)$ alkyl, $(C_1-C_6)$ haloalkyl, or $(C_1-C_6)$ alkoxy$(C_1-C_6)$alkyl, or $R^3$ is a group of the formula -J-K, wherein J is $(C_1-C_3)$ alkylene, —C(=S)—, or —C(=S)—;

K is $(C_3-C_{10})$ cycloalkyl, $(C_6-C_{10})$ aryl, 5- to 6-membered heteroaryl, or 5- to 6-membered heterocyclyl, wherein said cycloalkyl, aryl, heteroaryl, or heterocyclyl of K is unsubstituted or substituted with one to four moieties, wherein said moieties are the same or different, and wherein said moieties are selected from the group consisting of $(C_1-C_6)$ alkyl, $(C_1-C_6)$ alkoxy, $(C_1-C_6)$ haloalkyl, halo, amino, $(C_1-C_6)$ alkylamino, di$(C_1-C_6)$ alkylamino, —CN, —OCF$_3$, and $R^{25}$;

$R^{25}$ is $(C_6-C_{10})$ aryl or 5- to 6-membered heteroaryl, wherein said aryl or heteroaryl of $R^{25}$ is unsubstituted or substituted with one to four moieties, wherein said moieties are selected from the group consisting of $(C_1-C_6)$ alkyl, hydroxyl, $(C_1-C_6)$ alkoxy, halo, amino, $(C_1-C_6)$ alkylamino, di$(C_1-C_6)$alkylamino, —CF$_3$, —OCF$_3$, and —CN;

each occurrence of $R^{10}$ is independently H, $(C_1-C_3)$ alkyl, fluoro, $(C_1-C_3)$ fluoroalkyl, or $(C_1-C_3)$ alkoxy;

$R^4$ is absent, halo, cyano, $(C_1-C_3)$ alkyl, or $(C_1-C_3)$ fluoroalkyl;

D is a group of the formula:

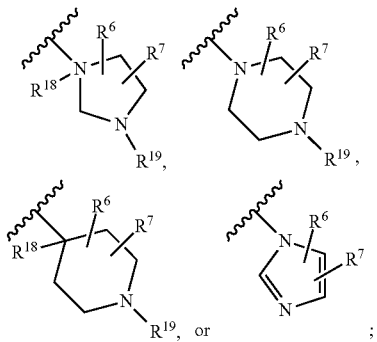

wherein $R^6$ and $R^7$ are independently absent or present, and if present are independently $(C_1-C_3)$ alkyl, $(C_1-C_3)$ fluoroalkyl, —CH$_2$—O—$(C_1-C_3)$alkyl, —CH$_2$CH$_2$—O—$(C_1-C_3)$ alkyl, —CH$_2$CH$_2$CH$_2$—O—$(C_1-C_3)$ alkyl, and wherein $R^6$ and $R^7$ are substituted on a carbon atom;

$R^{18}$ is H, —CN, hydroxy, $(C_1-C_6)$ alkyl, or $(C_1-C_6)$ alkoxy; and $R^{19}$ is H or $(C_1-C_3)$ alkyl.

In some embodiments of the compounds of the Formula (Ia), $R^1$ is halo or cyano, and $R^2$ is absent.

In certain embodiments of the compounds of the Formula (Ia), $X^1$ is O.

In other embodiments of the compounds of the Formula (Ia), $X^1$ is S.

In some embodiments of the compounds of the Formula (Ia), each occurrence of $R^{10}$ is H.

In certain embodiments of the compounds of the Formula (Ia), $R^3$ is $(C_1-C_6)$ alkyl, $(C_1-C_6)$ haloalkyl, or $(C_1-C_6)$alkoxy$(C_1-C_6)$alkyl.

In some embodiments of the compounds of the Formula (Ia), $R^3$ is -J-K, wherein J is methylene, K is 3- to 6-membered cycloalkyl or phenyl, wherein said cycloalkyl or phenyl of K is unsubstituted or is substituted with one to two moieties, wherein said moieties are the same or different, and wherein said moieties are selected from the group consisting of $(C_1-C_6)$ alkyl, $(C_1-C_6)$ alkoxy, $(C_1-C_6)$ haloalkyl, halo, amino, $(C_1-C_6)$ alkylamino, di$(C_1-C_6)$alkylamino, —CN, —OCF$_3$, and $R^{25}$; and $R^{25}$ is phenyl or 5- to 6-membered heteroaryl, wherein said phenyl or heteroaryl of $R^{25}$ is unsubstituted or substituted with one to four moieties, wherein said moieties are selected from the group consisting of $(C_1-C_6)$ alkyl, hydroxyl, $(C_1-C_6)$ alkoxy, halo, amino, $(C_1-C_6)$ alkylamino, di$(C_1-C_6)$alkylamino, —CF$_3$, —OCF$_3$, and —CN.

In specific instances of such embodiments, $R^{25}$ is pyridyl or pyrimidyl wherein said pyridyl or pyrimidyl is unsubstituted or substituted with one to four moieties, wherein said moieties are selected from the group consisting of $(C_1-C_6)$ alkyl, hydroxyl, $(C_1-C_6)$ alkoxy, halo, amino, $(C_1-C_6)$ alkylamino, di$(C_1-C_6)$alkylamino, —CF$_3$, —OCF$_3$, and —CN.

In certain embodiments of the compounds of the Formula (Ia), $R^4$ is absent.

In some embodiments of the compounds of the Formula (Ia), D is

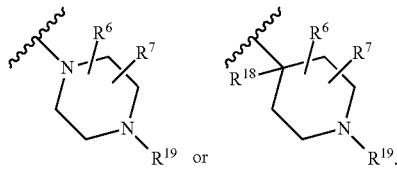

In certain instances, $R^6$ and $R^7$ are absent and $R^{18}$ is H in the D ring.

In another aspect, the present invention provides compounds having the Formula (Ib):

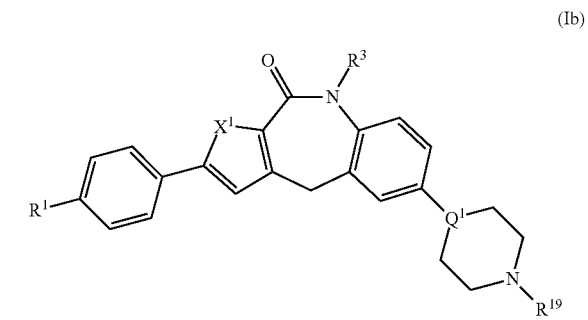

(Ib)

or a pharmaceutically acceptable salt thereof, wherein $R^1$ is halo or cyano;

$X^1$ is O or S;

$R^3$ is H, $(C_1-C_6)$ alkyl, halo$(C_1-C_6)$alkyl, or $(C_1-C_6)$ alkoxy $(C_1-C_6)$alkyl, or $R^3$ is a group of the formula wherein J is $(C_1-C_3)$ alkylene, —C(=O)—, or —C(=S)—;

K is $(C_3-C_{10})$cycloalkyl, $(C_6-C_{10})$ aryl, 5- to 6-membered heteroaryl, or 5- to 6-membered heterocyclyl, wherein said cycloalkyl, aryl, heteroaryl, or heterocyclyl of K is unsubstituted or substituted with one to four moieties, wherein said moieties are the same or different, and wherein said moieties are selected from the group consisting of ($C_1$-$C_6$) alkyl, ($C_1$-$C_6$) alkoxy, ($C_1$-$C_6$) haloalkyl, halo, amino, ($C_1$-$C_6$) alkylamino, di($C_1$-$C_6$) alkylamino, —CN, —$OCF_3$, and $R^{25}$;

$R^{25}$ is ($C_6$-$C_{10}$) aryl or 5- to 6-membered heteroaryl, wherein said aryl or heteroaryl of $R^{25}$ is unsubstituted or substituted with one to four moieties, wherein said moieties are selected from the group consisting of ($C_1$-$C_6$) alkyl, hydroxyl, ($C_1$-$C_6$) alkoxy, halo, amino, ($C_1$-$C_6$) alkylamino, di($C_1$-$C_6$)alkylamino, —$CF_3$, —$OCF_3$, or —CN;

$Q^1$ is N or C($R^{18}$);

$R^{18}$ is H, —CN, hydroxy, ($C_1$-$C_6$) alkyl, or ($C_1$-$C_6$) alkoxy; and $R^{19}$ is H or ($C_1$-$C_3$) alkyl.

In some embodiments of the compounds of the Formula (Ib), $X^1$ is O.

In other embodiments of the compounds of the Formula (Ib), $X^1$ is S.

In some embodiments of the compounds of the Formula (Ib), $R^3$ is H, methyl, ethyl, propyl, butyl, trifluoromethyl, 2,2,2-trifluoroethyl, 2,2-difluoroethyl, methoxymethyl, ethoxymethyl, propoxymethyl, 2-methoxyethyl, 2-ethoxyethyl, 2-propoxyethyl; or $R^3$ is -J-K wherein J is methylene, K is 3- to 6-membered cycloalkyl or phenyl, wherein said cycloalkyl or phenyl of K is unsubstituted or is substituted with one to two moieties, wherein said moieties are the same or different, and wherein said moieties are selected from the group consisting of ($C_1$-$C_6$) alkyl, ($C_1$-$C_6$) alkoxy, ($C_1$-$C_6$) haloalkyl, halo, amino, ($C_1$-$C_6$) alkylamino, di($C_1$-$C_6$)alkylamino, —CN, —$OCF_3$, and $R^{25}$;

$R^{25}$ is phenyl or 5- to 6-membered heteroaryl, wherein phenyl or heteroaryl of $R^{25}$ is unsubstituted or substituted with one to four moieties, wherein said moieties are selected from the group consisting of ($C_1$-$C_6$) alkyl, hydroxyl, ($C_1$-$C_6$) alkoxy, halo, amino, ($C_1$-$C_6$) alkylamino, di($C_1$-$C_6$)alkylamino, —$CF_3$, —$OCF_3$, and —CN.

In certain embodiments of the compounds of the Formula (Ib), $R^3$ is H, methyl, 2,2-difluoroethyl, methoxymethyl; or $R^3$ is —$CH_2$—K, wherein K is cyclopropyl, phenyl, or phenyl substituted with one to two moieties, wherein said moieties are the same or different, and wherein said moieties are selected from the group consisting of halo, amino, and $R^{25}$;

wherein $R^{25}$ is phenyl or 5- to 6-membered heteroaryl, wherein said phenyl or heteroaryl of $R^{25}$ is unsubstituted or substituted with one moiety, wherein said moiety is selected from the group consisting of ($C_1$-$C_6$) alkoxy and amino.

In specific embodiments of the compounds of the Formula (Ib), $R^3$ is H, methyl, 2,2-difluoroethyl, methoxymethyl; or $R^3$ is —$CH_2$—K, wherein K is cyclopropyl, phenyl, or phenyl substituted with one to two moieties, wherein said moieties are the same or different, and wherein said moieties are selected from the group consisting of halo, amino, and $R^{25}$;

wherein $R^{25}$ is phenyl or 5- to 6-membered heteroaryl, wherein said phenyl or heteroaryl of $R^{25}$ is unsubstituted or substituted with one moiety, wherein said moiety is selected from the group consisting of ($C_1$-$C_6$) alkoxy and amino.

In some embodiments of the compounds of the Formula (Ib), $R^3$ is —$CH_2$—K, wherein K is phenyl substituted by one $R^{25}$, wherein $R^{25}$ is pyridyl or pyrimidyl, wherein said pyridyl or pyrimidyl is unsubstituted or substituted with one to four moieties, wherein said moieties are selected from the group consisting of ($C_1$-$C_6$) alkyl, hydroxyl, alkoxy, halo, amino, alkylamino, dialkylamino, —$CF_3$, —$OCF_3$, and —CN.

In some embodiments of the compounds of the Formula (Ib), $R^3$ is —$CH_2$—K, 3 is methylene, and K is phenyl substituted by one $R^{25}$, wherein $R^{25}$ is pyridyl or pyrimidyl, wherein said pyridyl or pyrimidyl is unsubstituted or substituted with one moiety, wherein said moiety is selected from the group consisting of ($C_1$-$C_6$) alkoxy and amino.

In certain embodiments of the compounds of the Formula (Ib), $R^{19}$ is H, methyl, ethyl, or n-propyl. For instance, $R^{19}$ can be H or methyl.

In some embodiments of the compounds of the Formula (Ib), $Q^1$ is N.

In other embodiments of the compounds of the Formula (Ib), $Q^1$ is C($R^{18}$), wherein $R^{18}$ is H, —CN, hydroxy, ($C_1$-$C_6$) alkyl, or ($C_1$-$C_6$) alkoxy. For example, in some embodiments, $Q^1$ is C(H).

In some embodiments of the compounds of the Formula (Ib), $R^3$ is H, methyl, 2,2-difluoroethyl, methoxymethyl; or —$CH_2$—K, wherein K is cyclopropyl, phenyl, or phenyl substituted with one to two moieties, wherein said moieties are the same or different, and wherein said moieties are selected from the group consisting of ($C_1$-$C_6$) alkyl, ($C_1$-$C_6$) alkoxy, halo($C_1$-$C_6$)alkyl, halo, —CN, —$OCF_3$, and $R^{25}$;

$R^{25}$ is phenyl, pyridyl, or pyrimidyl, wherein said phenyl, pyridyl, or pyrimidyl of $R^{25}$ is unsubstituted or substituted with one moiety, wherein said moiety is selected from the group consisting of ($C_1$-$C_6$)alkoxy and amino.

$Q^1$ is N or C(H); and $R^{39}$ is H or methyl.

In another embodiment, the present invention provides a compound of the Formula (I), or a pharmaceutically acceptable salt thereof, wherein the compound is selected from one of the following compounds (wherein the compound number is set forth under the compound's structure):

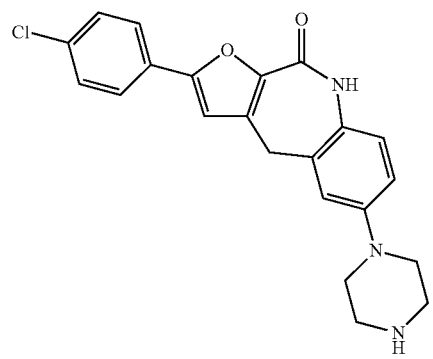

1

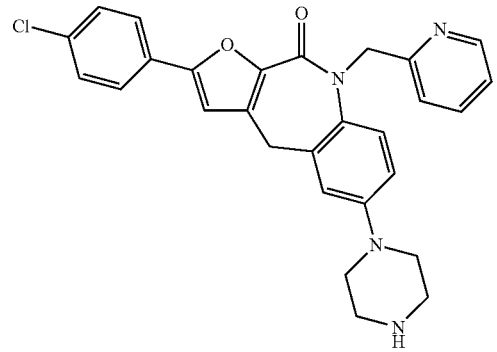

2

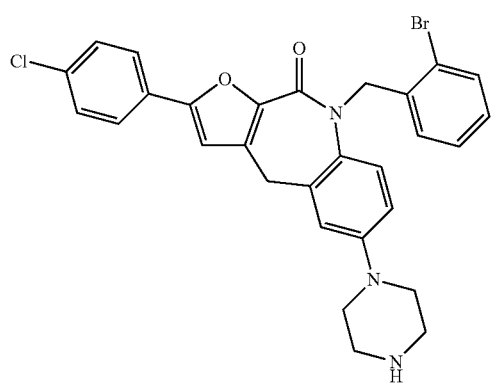
3
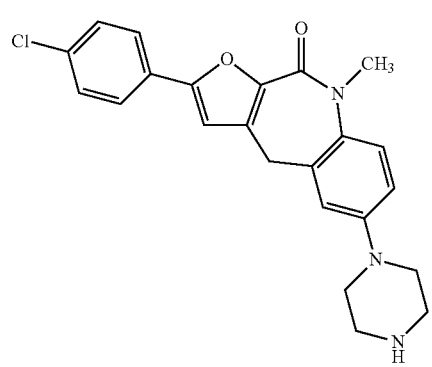
4
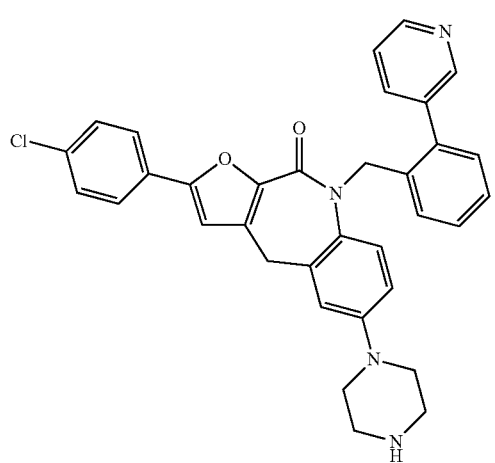
5
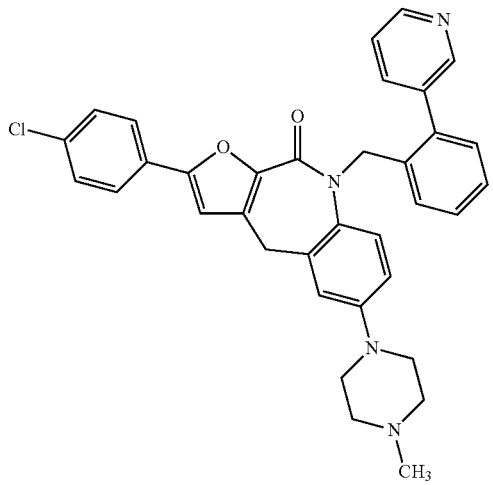
6
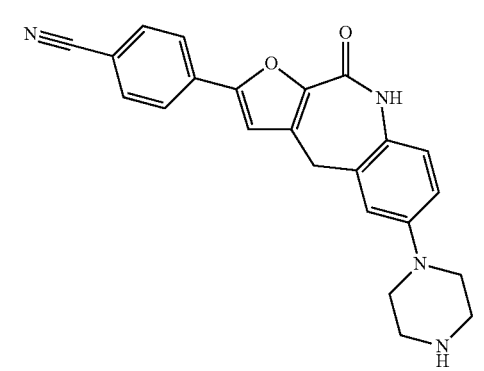
7
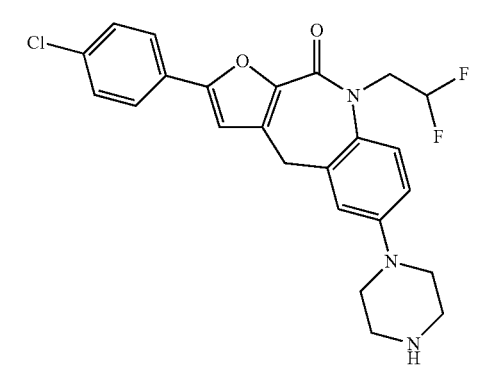
8
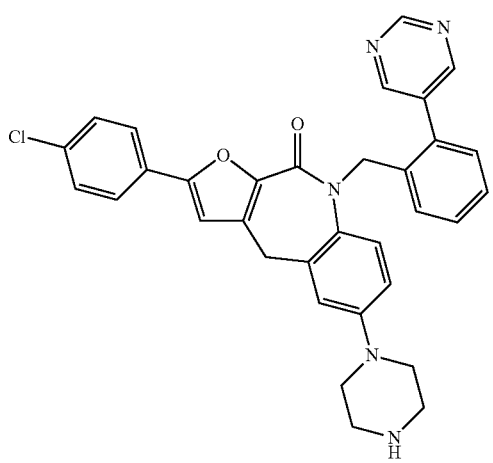
9

10
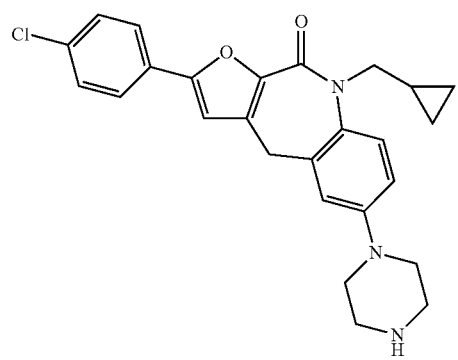
11
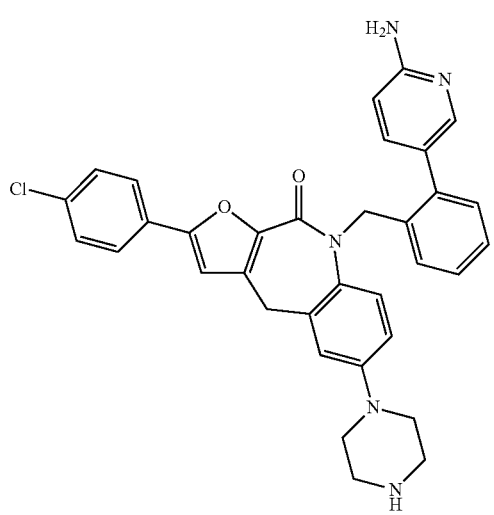
12
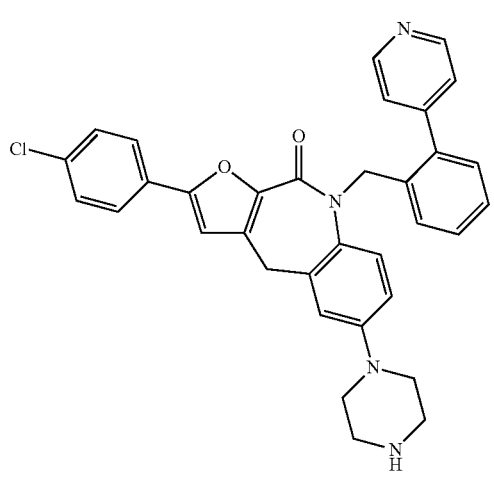
13
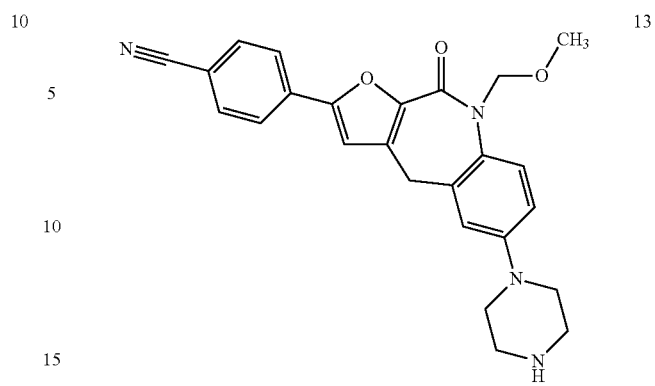
14
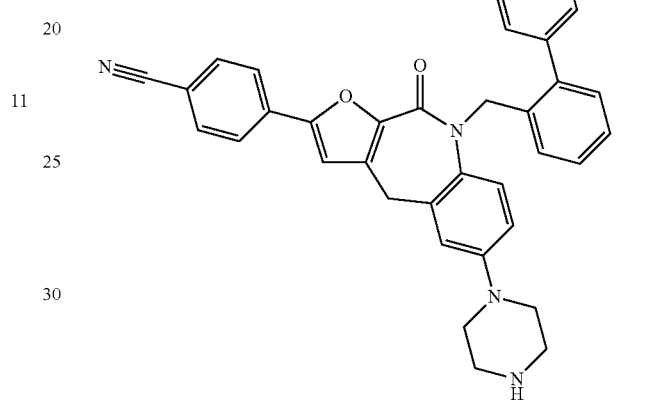
15
16
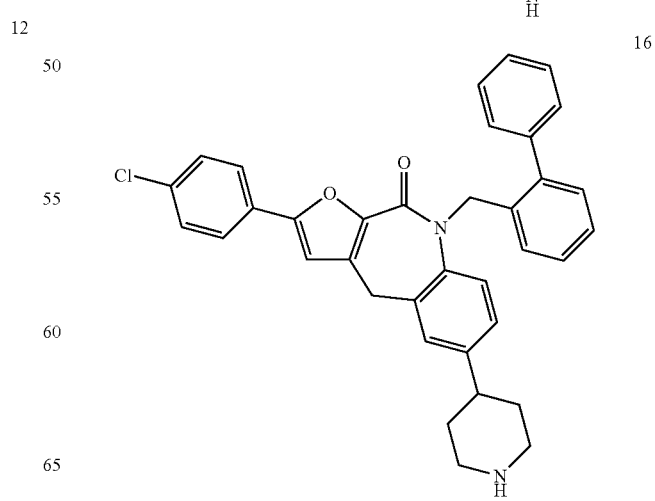

17
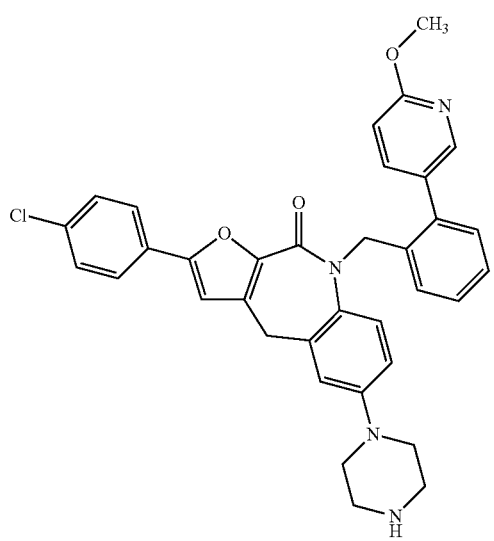
18
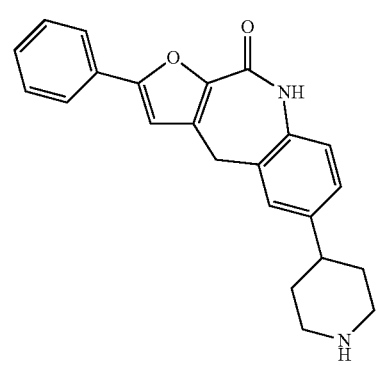
19
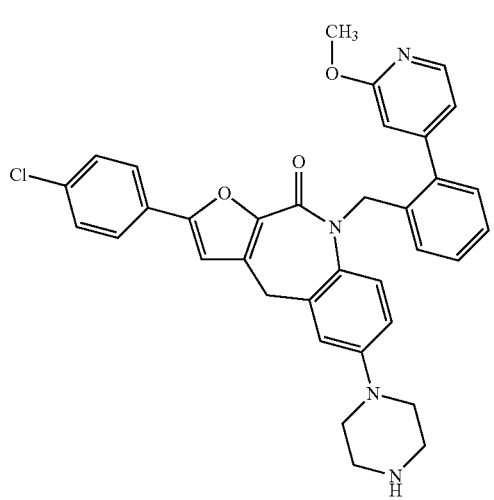
20
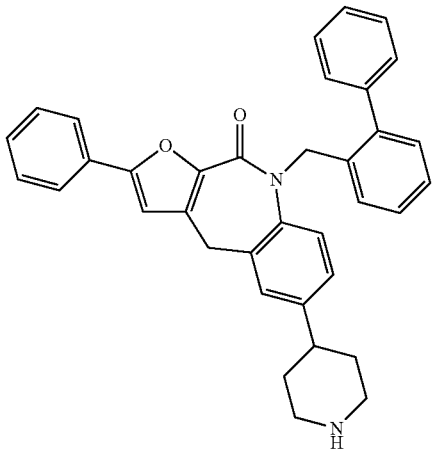
21
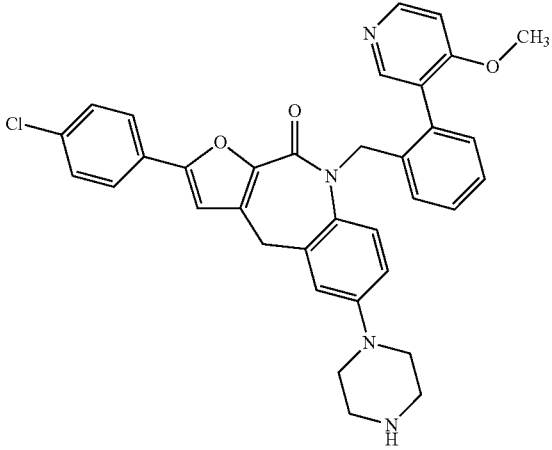
22
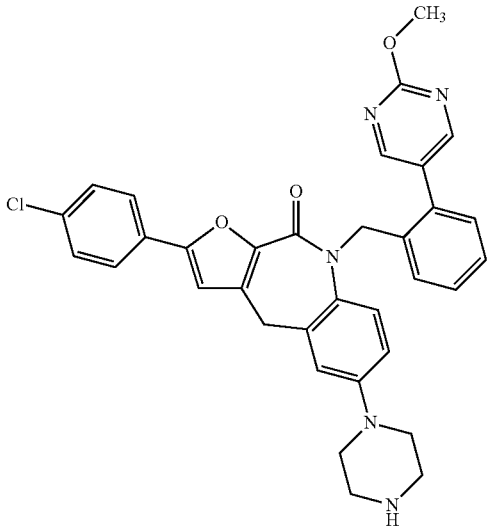

-continued

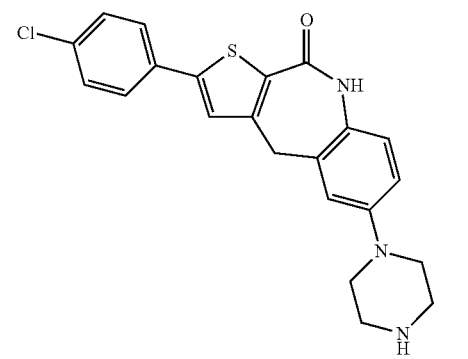
23

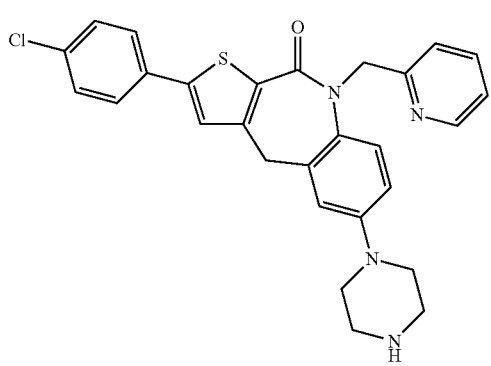
24

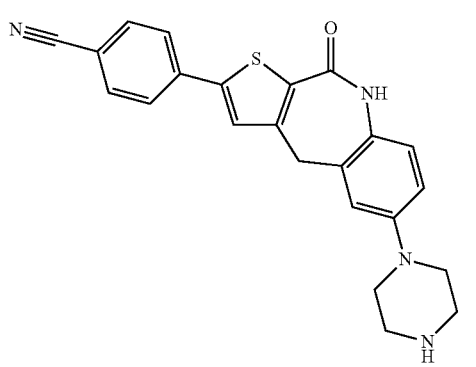
25

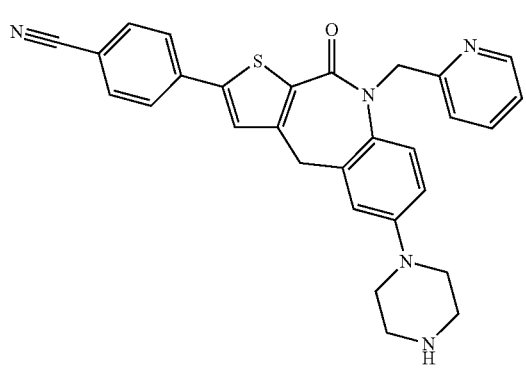
26

-continued

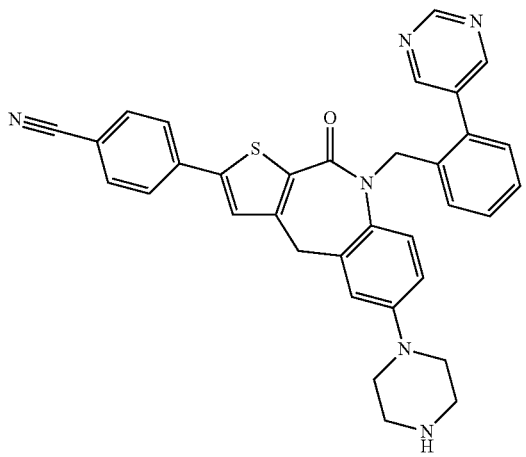
27

Methods For Making the Compounds of Formula (I)

The compounds of Formula (I) may be prepared from known or readily prepared starting materials, following methods known to one skilled in the art of organic synthesis. Methods useful for making the compounds of Formula (I) are set forth in the Examples below. Alternative synthetic pathways and analogous structures will be apparent to those skilled in the art of organic synthesis. All stereoisomers and tautomeric forms of the compounds are contemplated.

The starting materials and reagents described in the Examples and in the schemes below are either available from commercial suppliers such as Sigma-Aldrich (St. Louis, Mo.) and Acros Organics Co. (Fair Lawn, N.J.), or can be prepared using methods well-known to one skilled in the art of organic synthesis.

One skilled in the art of organic synthesis will also recognize that the synthesis of Fused Tricyclic compounds of Formula (I) may require protection of certain functional groups (i.e., derivatization for the purpose of chemical compatibility with a particular reaction condition). Suitable protecting groups for the various functional groups of these compounds and methods for their installation and removal can be found in Greene et al., *Protective Groups in Organic Synthesis*, Wiley-Interscience, New York, (1999).

The starting materials used and the intermediates prepared using the methods set forth in the schemes above may be isolated and purified if desired using conventional techniques, including but not limited to filtration, distillation, crystallization, chromatography and alike. Such materials can be characterized using conventional means, including physical constants and spectral data.

EXAMPLES

General Methods

Solvents, reagents, and intermediates that are commercially available were used as received. Reagents and intermediates that are not commercially available were prepared in the manner as described below. $^1$H NMR spectra were obtained on a Varian AS-400 (400 MHz) and are reported as ppm down field from $Me_4Si$ with number of protons, multiplicities, and coupling constants in Hz indicated parenthetically. Where LC/MS data are presented, analyses were performed using an Applied Biosystems API-100 mass spectrometer and Shimadzu SCL-10A LC column: Altech platinum C18, 3 micron, 33 mm×7 mm ID; gradient flow: 0 min—10% CH₃CN, 5 min—95% CH₃CN, 7 min—95% CH₃CN, 7.5 min—10% CH₃CN, 9 min—stop. MS data were obtained using Agilent Technologies LC/MSD SL or 1100 series LC/MSD mass spectrometer.

Final compounds were purified by PrepLC using the column of Varian Pursuit XRs C18 10µ 250×21.2 mm and an eluent mixture of mobile phase A and B. The mobile phase A is composed of 0.1% TFA in H₂O and the mobile phase B is composed of CH₃CN (95%)/H₂O (5%)/TFA (0.1%). The mixture of mobile phase A and B was eluted through the column at a flow rate of 20 mL/min at room temperature.

The purity of all the final discrete compounds was checked by LCMS using a Higgins Haisil HL C18 5µ 150×4.6 mm column and an eluent mixture of mobile phase A and B, wherein mobile phase A is composed of 0.1% TFA in H₂O and the mobile phase B is composed of CH₃CN (95%)/H₂O (5%)/TFA (0.1%). The column was eluted at a flow rate of 3 mL/min at a temperature of 60° C.

Intermediate compounds were characterized by LCMS using a Higgins Haisil HL C18 5µ 50×4.6 mm column and an eluent mixture of mobile phase A and B, wherein mobile phase A is composed of 0.1% TFA in H₂O and the mobile phase B is composed of CH₃CN (95%)/H₂O (5%)/TFA (0.1%). The column was eluted at a flow rate of 3 mL/min at a column temperature of 60° C.

Example 1

Preparation of Compound 5

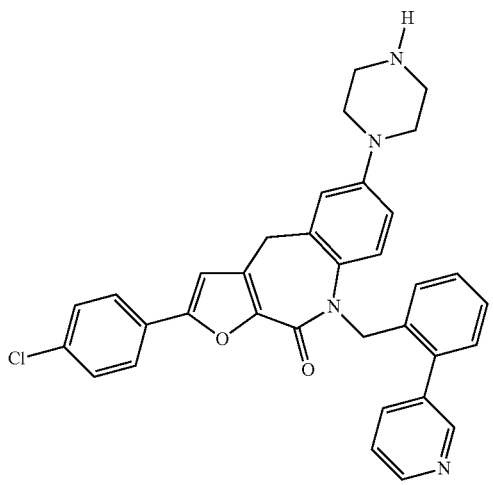

This example illustrates embodiments of the invention wherein D is a piperazine ring; $R^3$ is a -group of the formula J-K, wherein J is methylene; and K is aryl substituted by $R^{25}$, wherein $R^{25}$ is pyridine.

Step A—Synthesis of Int-1a

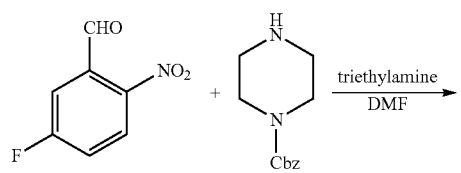

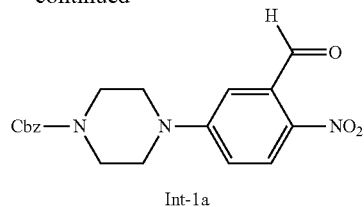

A mixture of 5-fluoro-2-nitrobenzaldehyde (20 g, 118 mmol) in DMF (150 mL), benzyl 1-piperazine carboxylate (31.2 g, 142 mmol), and triethylamine (14.3 g, 142 mmol) was heated to 80° C. for 15 hours. After cooling to room temperature, the reaction mixture was diluted with EtOAc (300 mL), washed with brine (3×150 mL), dried over Na₂SO₄, filtered, and concentrated. The resulting thick oil was purified by a flash column, eluting with 20% EtOAc/hexanes to yield 36.2 g (86%) of Int-1a as a yellow solid.

Step B—Synthesis of Int-1b

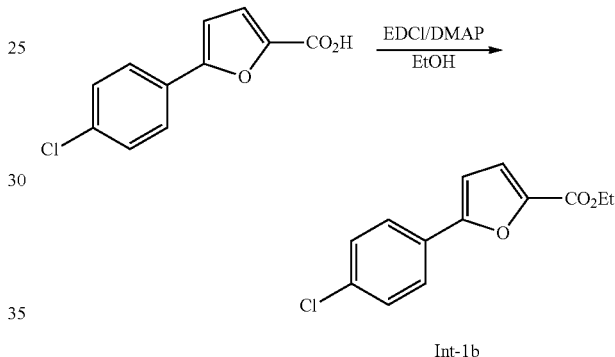

A mixture of 5-(4-chlorophenyl)furic acid (10 g, 45 mmol) in EtOH (200 mL), EDCI (17.3 g, 90 mmol), and DMAP (5.5 g, 45 mmol) was stirred at RT for 15 hours. The reaction mixture was diluted with EtOAc (300 mL), washed with water (2×150 mL), dried over Na₂SO₄, filtered, and concentrated. The resulting oil was purified by a flash column, eluting with 10% EtOAc/hexanes to yield 10.2 g (93%) of Int-1b as a white solid.

Step C—Synthesis of Int-1c

-continued

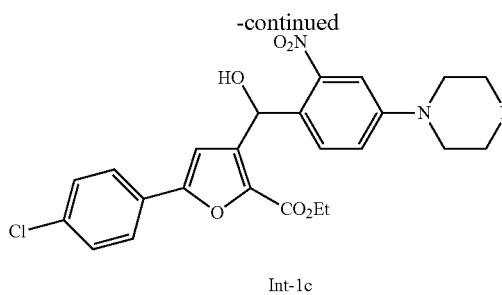

Int-1c

Into 2,2,6,6-tetramethyl piperidine (4.2 g, 30 mmol) was added (via syringe) isopropylmagnesium chloride lithium chloride complex (1.3 M in THF). After stirring at RT for 15 hours, the solution was cooled to −20° C. A solution of compound Int-1b (5 g, 20 mmol) in THF (15 mL) was added (via syringe) at −20° C. After the reaction mixture was stirred at −20° C. for 2 hours, a solution of compound Int-1a (7.4 g, 20 mmol) in THF/DMPU (30 mL, 9:1) was added (via syringe). Then, the reaction mixture was stirred at −20° C. for 2 hours. The reaction mixture was diluted with EtOAc (300 mL), washed with saturated $NH_4Cl$ (200 mL), dried over $Na_2SO_4$, filtered, and concentrated to ~120 mL. The yellow precipitate was isolated to give compound Int-1c (6.9 g, 55%) as a yellow solid.

Step D—Synthesis of Int-1d

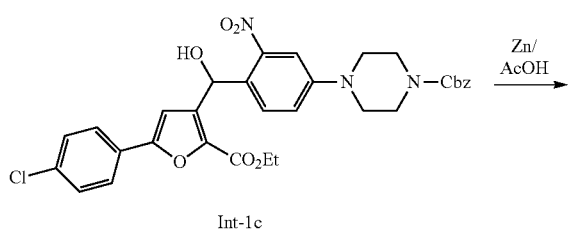

Int-1c

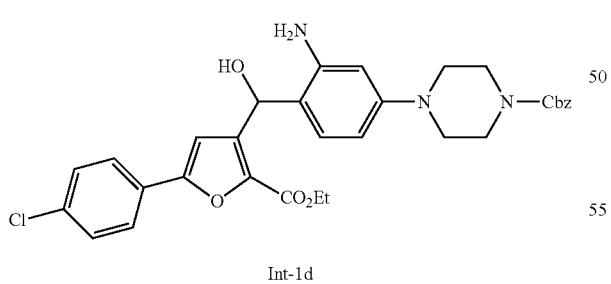

Int-1d

A mixture of compound Int-1c (5 g, 8.1 mmol) in acetic acid (30 mL) and Zn dust (3.2 g, 48.4 mmol) was stirred at RT for 2 hours. The reaction mixture was diluted with EtOAc (200 mL) and filtered from the catalyst. The resulting filtrate was concentrated, neutralized, and purified by flash column chromatography, eluting with 2% $NH_3$ (7 N in MeOH)/$CH_2Cl_2$ to yield 4.4 g (94%) of compound Int-1d as a beige solid.

Step E—Synthesis of Int-1e

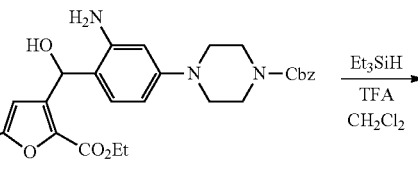

Int-1d

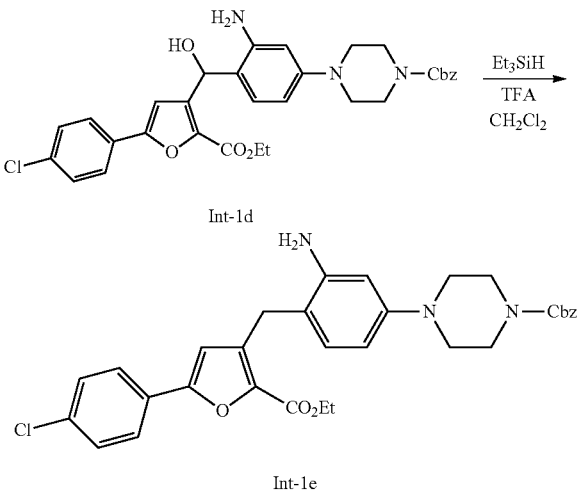

Int-1e

Into a solution of Int-4-d (4.4 g, 7.4 mmol) in $CH_2Cl_2$ (30 mL) and triethyl silane (8.7 g, 74 mmol) was added (via addition funnel) TFA (36 mL). After the reaction mixture was stirred at RT for 15 hours, the reaction mixture was concentrated. The resulting paste was diluted with EtOAc (300 mL), washed with saturated $K_2CO_3$ (2×150 mL), dried over $Na_2SO_4$, filtered, and concentrated. The resulting thick oil was purified by a flash column, eluting with 30% EtOAc/hexanes to yield 2.8 g (65%) of Int-1e as a yellow solid.

Step F—Synthesis of Int-1f

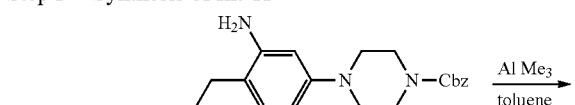

Int-1e

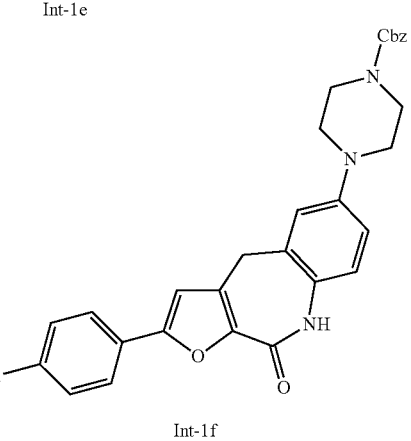

Int-1f

Into a solution of compound Int-1e (2.5 g, 4.3 mmol) in toluene (60 mL) was added dropwise (via syringe) trimethylaluminum (2 M in hexanes, 11 mL). After the reaction mixture was stirred at RT for two hours, it was heated to 80° C. for one hour. The reaction mixture was diluted with EtOAc (100 mL), washed with saturated sodium potassium tartrate (2×100 mL), dried over $Na_2SO_4$, filtered, and concentrated. The resulting solid was purified by flash column chromatography, eluting with 40% EtOAc/hexanes to yield 1.3 g (57%) of compound Int-1f as a yellow solid.

Step G—Synthesis of Int-1g

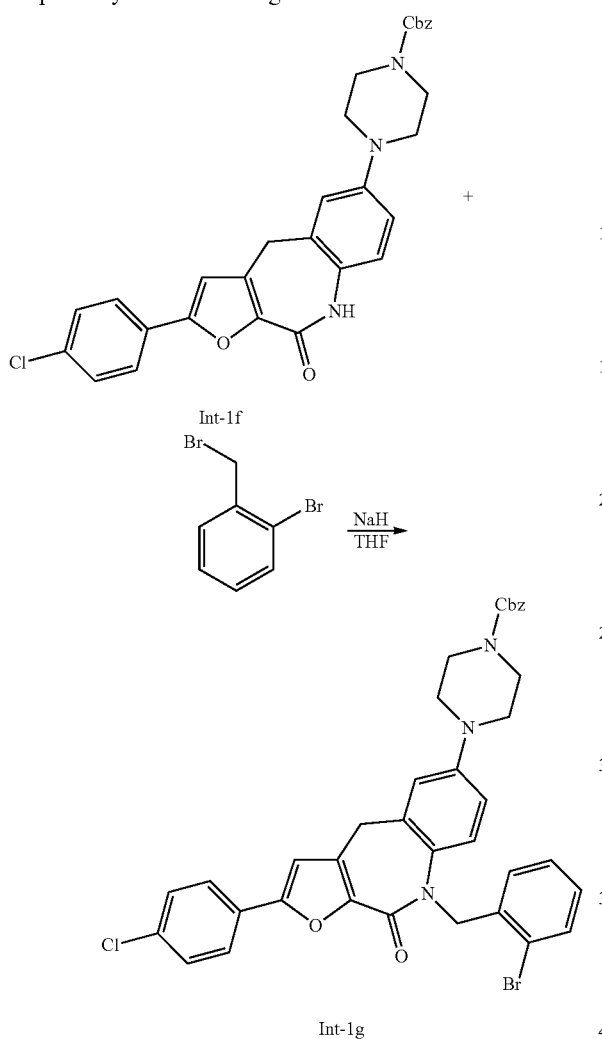

A mixture of compound Int-1f (0.26 g, 0.5 mmol) in THF (5 mL) and NaH (60% on mineral oil, 60 mg, 1.5 mmol), and 2-bromophenyl methylbromide was stirred at RT for 15 hours. The reaction mixture was diluted with EtOAc (40 mL), washed with saturated $NH_4Cl$ (2×30 mL), dried over $Na_2SO_4$, filtered, and concentrated. The concentrate was purified by flash column chromatography, eluting with 30% EtOAc/hexanes to yield 0.26 g (74%) of compound Int-1g as a beige solid.

Step H—Synthesis of Int-1 h

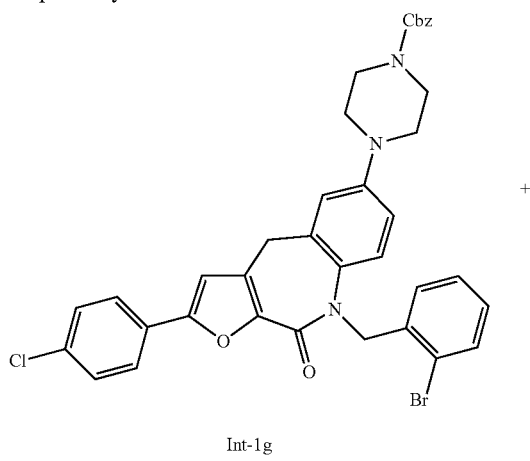

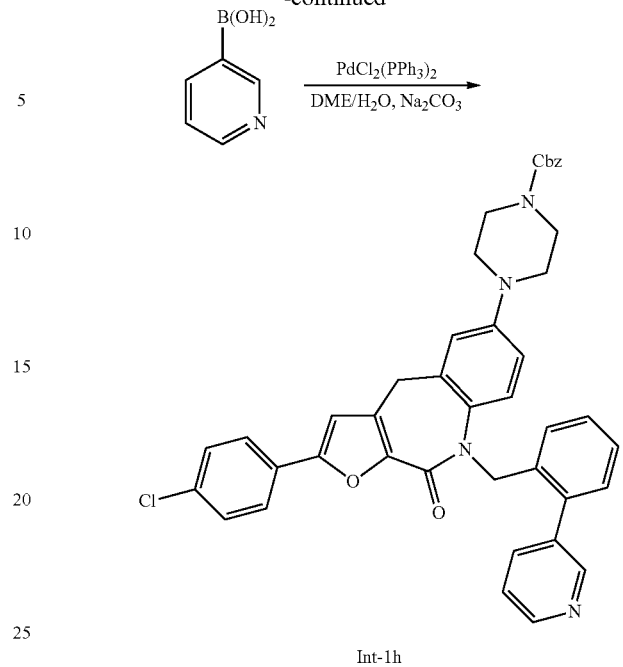

A mixture of compound Int-1g (0.16 g, 0.23 mmol) in $DME/H_2O$ (3 mL, 4:1), 3-pyridineboronic acid (51 mg, 0.41 mmol), $PdCl_2(PPh_3)_2$ (16 mg, 0.023 mmol), and $Na_2CO_3$ (73 mg, 0.69 mmol) was subjected a microwave reaction at 140° C. for one hour. The reaction mixture was purified by a flash column, eluting with 1.5% $NH_3$ (7 N in MeOH)/$CH_2Cl_2$ to yield 0.1 g (62%) of compound Int-1 h as a yellow solid.

Step I—Synthesis of Compound 5

-continued

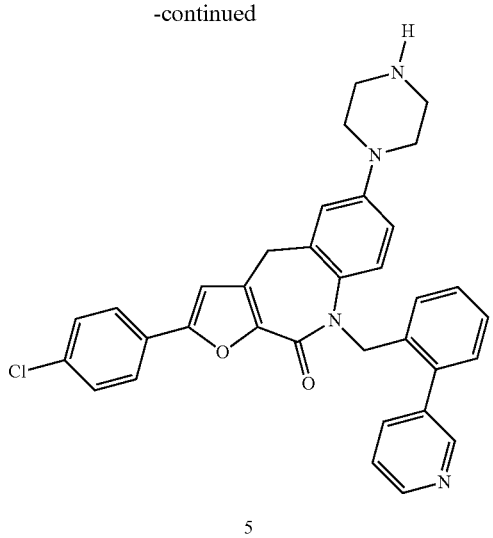

5

A mixture of compound Int-1h (95 mg, 0.134 mmol) in CH$_2$Cl$_2$ (2 mL) and TMSI (164 mg, 0.82 mmol) was stirred at RT for 1 hour. The reaction mixture was quenched with water (0.1 mL), diluted with EtOAc (8 mL), washed with brine (2×8 mL), dried over Na$_2$SO$_4$, filtered, and concentrated, then purified by a flash column, eluting with 5% NH$_3$ (7 N in MeOH)/CH$_2$Cl$_2$ to yield 72 mg (62%) of compound 5 as a yellow solid.

Example 2

Preparation of Compound 9

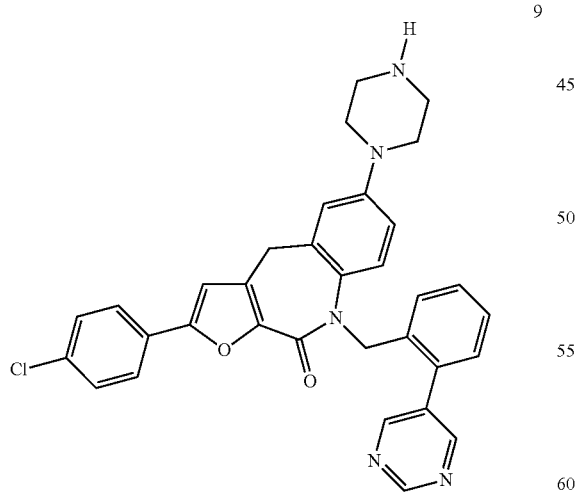

9

The preparation of Compound 9 was performed analogously to the preparation of compound 5 as described in Example 1 by substituting 5-pyrimidineboronic acid for 3-pyridineboronic acid in Step H.

Example 3

Preparation of Compound 14

Compound 14 was prepared according to the following scheme and the descriptions below. This example illustrates embodiments of the compounds of Formula (I) wherein ring E is phenyl substituted by —CN.

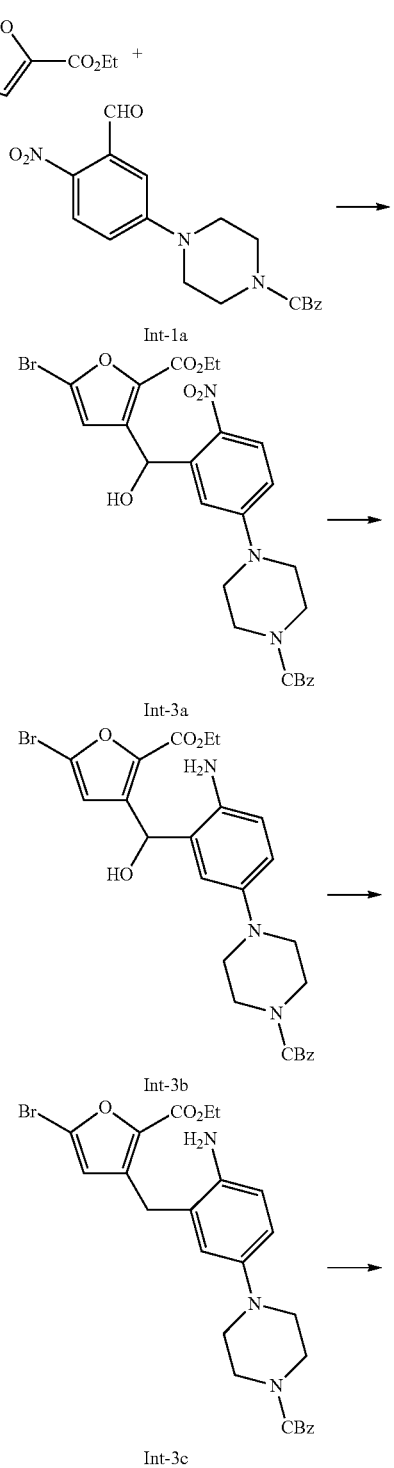

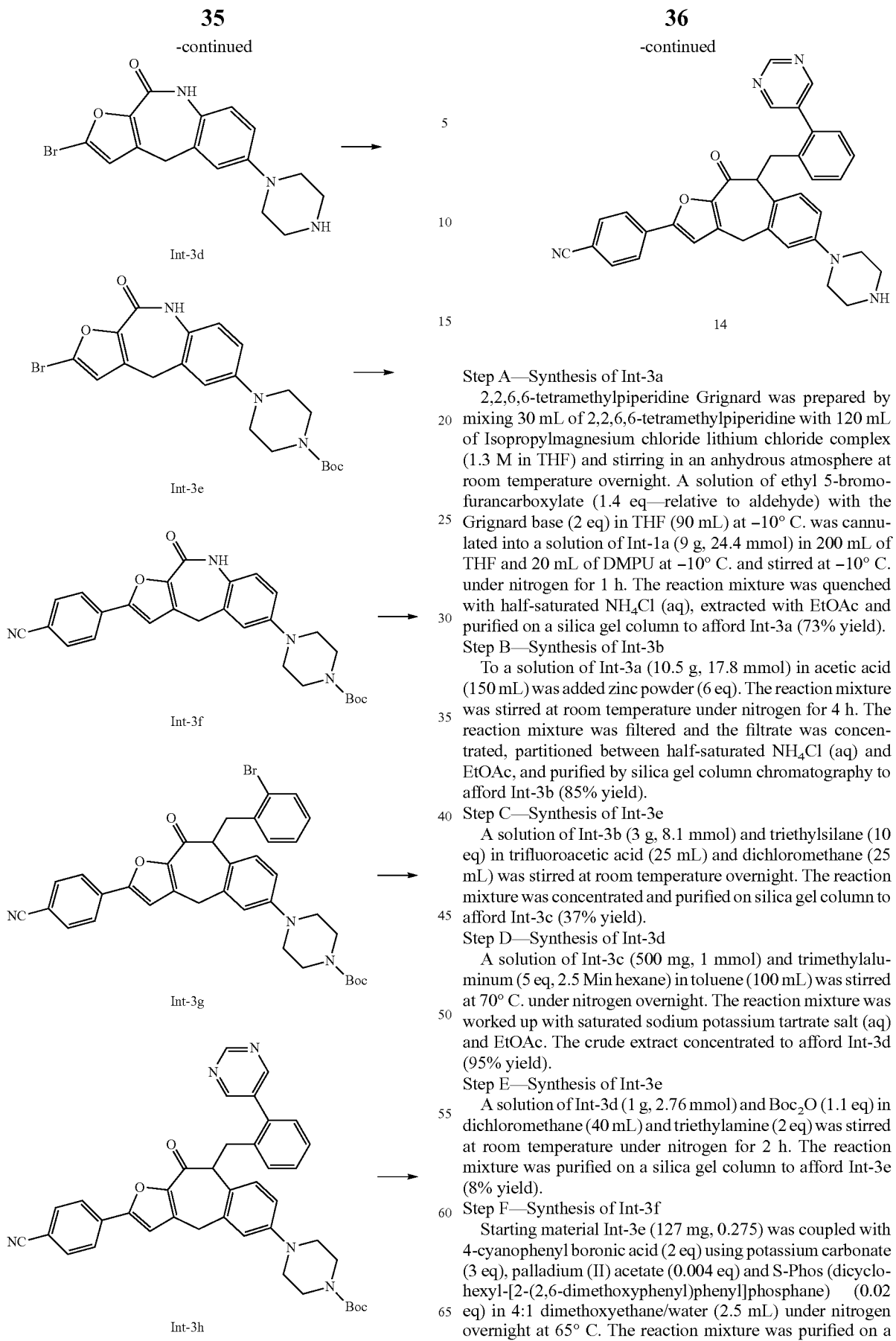

Step A—Synthesis of Int-3a 2,2,6,6-tetramethylpiperidine Grignard was prepared by mixing 30 mL of 2,2,6,6-tetramethylpiperidine with 120 mL of Isopropylmagnesium chloride lithium chloride complex (1.3 M in THF) and stirring in an anhydrous atmosphere at room temperature overnight. A solution of ethyl 5-bromo-furancarboxylate (1.4 eq—relative to aldehyde) with the Grignard base (2 eq) in THF (90 mL) at −10° C. was cannulated into a solution of Int-1a (9 g, 24.4 mmol) in 200 mL of THF and 20 mL of DMPU at −10° C. and stirred at −10° C. under nitrogen for 1 h. The reaction mixture was quenched with half-saturated $NH_4Cl$ (aq), extracted with EtOAc and purified on a silica gel column to afford Int-3a (73% yield).

Step B—Synthesis of Int-3b

To a solution of Int-3a (10.5 g, 17.8 mmol) in acetic acid (150 mL) was added zinc powder (6 eq). The reaction mixture was stirred at room temperature under nitrogen for 4 h. The reaction mixture was filtered and the filtrate was concentrated, partitioned between half-saturated $NH_4Cl$ (aq) and EtOAc, and purified by silica gel column chromatography to afford Int-3b (85% yield).

Step C—Synthesis of Int-3c

A solution of Int-3b (3 g, 8.1 mmol) and triethylsilane (10 eq) in trifluoroacetic acid (25 mL) and dichloromethane (25 mL) was stirred at room temperature overnight. The reaction mixture was concentrated and purified on silica gel column to afford Int-3c (37% yield).

Step D—Synthesis of Int-3d

A solution of Int-3c (500 mg, 1 mmol) and trimethylaluminum (5 eq, 2.5 M in hexane) in toluene (100 mL) was stirred at 70° C. under nitrogen overnight. The reaction mixture was worked up with saturated sodium potassium tartrate salt (aq) and EtOAc. The crude extract concentrated to afford Int-3d (95% yield).

Step E—Synthesis of Int-3e

A solution of Int-3d (1 g, 2.76 mmol) and $Boc_2O$ (1.1 eq) in dichloromethane (40 mL) and triethylamine (2 eq) was stirred at room temperature under nitrogen for 2 h. The reaction mixture was purified on a silica gel column to afford Int-3e (8% yield).

Step F—Synthesis of Int-3f

Starting material Int-3e (127 mg, 0.275) was coupled with 4-cyanophenyl boronic acid (2 eq) using potassium carbonate (3 eq), palladium (II) acetate (0.004 eq) and S-Phos (dicyclohexyl-[2-(2,6-dimethoxyphenyl)phenyl]phosphane) (0.02 eq) in 4:1 dimethoxyethane/water (2.5 mL) under nitrogen overnight at 65° C. The reaction mixture was purified on a silica gel column to afford Int-3f (82% yield).

Step G—Synthesis of Int-3g

Starting material Int-3f (140 mg, 0.289 mmol) was deprotonated using sodium hydride (3 eq, 60% in mineral oil) in THF (3 mL) at room temperature under nitrogen for 10 minutes. The reaction mixture was then charged with 2-bromobenzyl bromide (1.2 eq) and stirred at room temperature overnight. The reaction mixture was purified using a Gilson HPLC to afford Int-3g (60% yield).

Step H—Synthesis of Int-3h

Starting material Int-3g (114 mg, 0.174 mmol) was coupled with pyrimidine-5-boronic acid (1.8 eq) using potassium carbonate (3 eq), $PdCl_2(PPh_3)_2$ (0.1 eq) in 3:1 dimethoxyethane/water (4 mL) using a microwave reactor at 130° C. for 66 minutes. The reaction mixture was worked up in water and EtOAc and crude Int-3h was isolated (88% yield).

Step I—Synthesis of Compound 14

Int-3h (100 mg, 0.15 mmol) was deprotected using trifluoroacetic acid (2 mL) and dichloromethane (2 mL) at room temperature for 2 h. The reaction mixture was concentrated and purified by silica gel chromatography. The free base form of compound 14 was converted to the hydrochloride salt form using HCl (1 eq, 2 M in $Et_2O$) in dichloromethane (1 mL) to afford the HCl salt of compound 14 (75%).

Example 4

Preparation of Compound 15

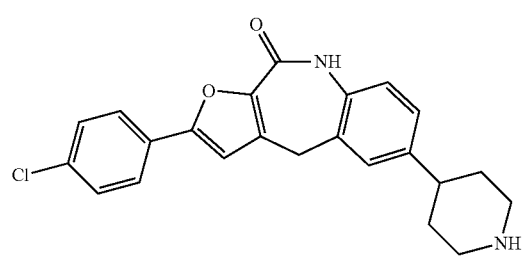

This example illustrates embodiments of the invention wherein ring D is a piperidine group in the compounds of Formula (I).

Step A—Synthesis of Int-4a

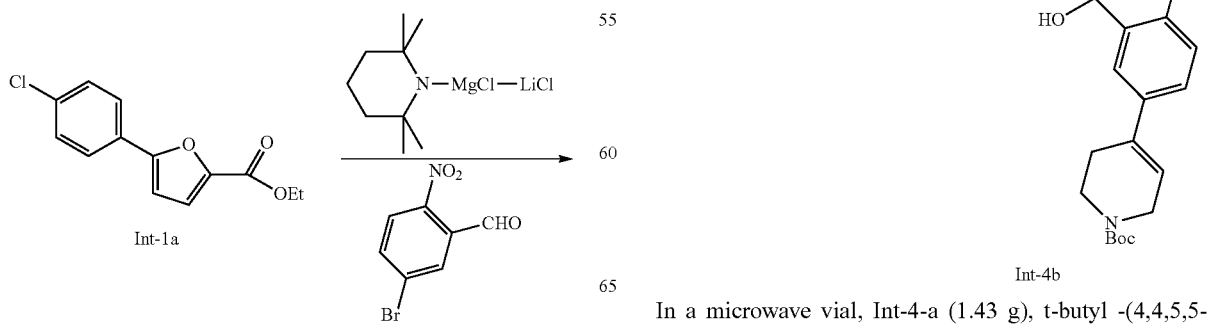

-continued

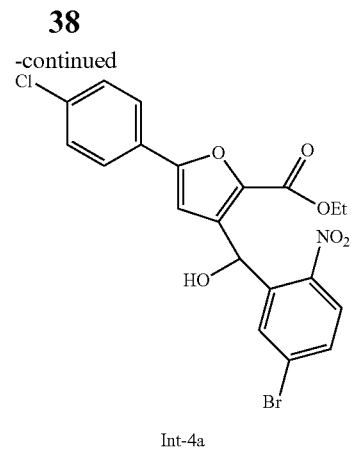

Int-4a

A solution of ethyl 5-(4-chlorophenyl)furan-2-carboxylate (Int-1a) (3.4 g) in THF (40 mL) was cooled to −15° C. in a dry ice/acetone bath over 20 min. A freshly made solution of Knochel's salt (22 mL, 1.5 eq) was added dropwise, and the reaction mixture was allowed to stir for 30 min at −30° C. In a separate flask, a solution of 5-bromo-2-nitrobenzaldehyde (3.1 g) in THF (135 mL, containing 10% DMPU) was cooled to −20° C. over 20 min, at which time the solution of deprotonated 5-(4-chlorophenyl)furan-2-carboxylate was added slowly via cannula. The combined reaction mixture was allowed to stir for 16 h while slowly warming up to 22° C. The reaction was then quenched by the addition of half saturated $NH_4Cl$ (aq) and extracted with EtOAc (3×). The combined organics were dried over $MgSO_4$, filtered and concentrated in vacuo. The residue was purified using an ISCO chromatography column in 0-25% EtOAc in (2:1 Hex/DCM) to afford 2.85 g of Int-4-a.

Step B—Synthesis of Int-4-b

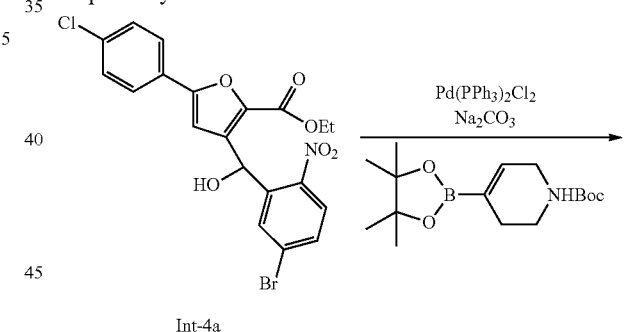

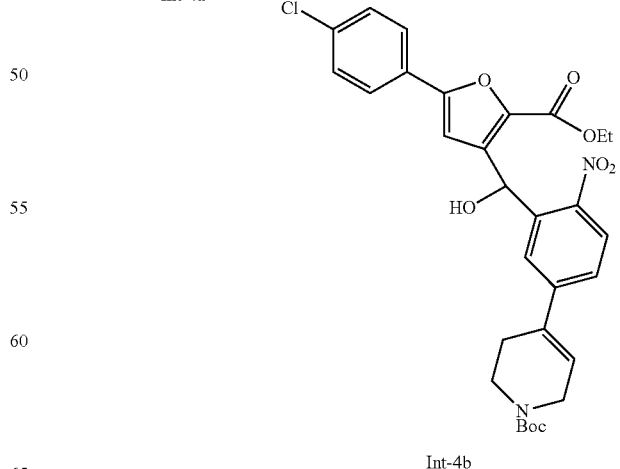

In a microwave vial, Int-4-a (1.43 g), t-butyl -(4,4,5,5-tetramethyl-1,3,2-dioxaborolan-2-yl)-5,6-dihydropyridine-1

(2H)-carboxylate (1.66 g), and Na$_2$CO$_3$ (944 mg) were combined and purged with N$_2$. To this mixture were added PdCl$_2$(PPh$_3$)$_2$ (208 mg) and 4:1 DME/H$_2$O (15 mL) and the mixture was purged with N$_2$ again. The vessel was sealed and the reaction was heated in the microwave at 120° C. for 45 min. The resulting mixture was filtered through a fiberglass frit and washed with MeOH. The filtrate was concentrated in vacuo and purified using an ISCO chromatography column in 0-80% EtOAc in Hex to afford 0.90 g of Int-4-b.

Step C—Synthesis of Int-4-c

Step D—Synthesis of Int-4-d

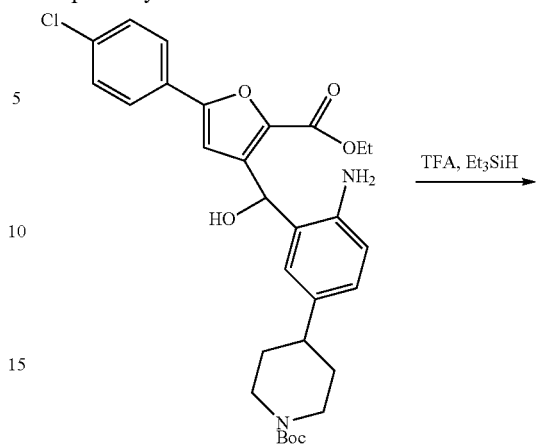

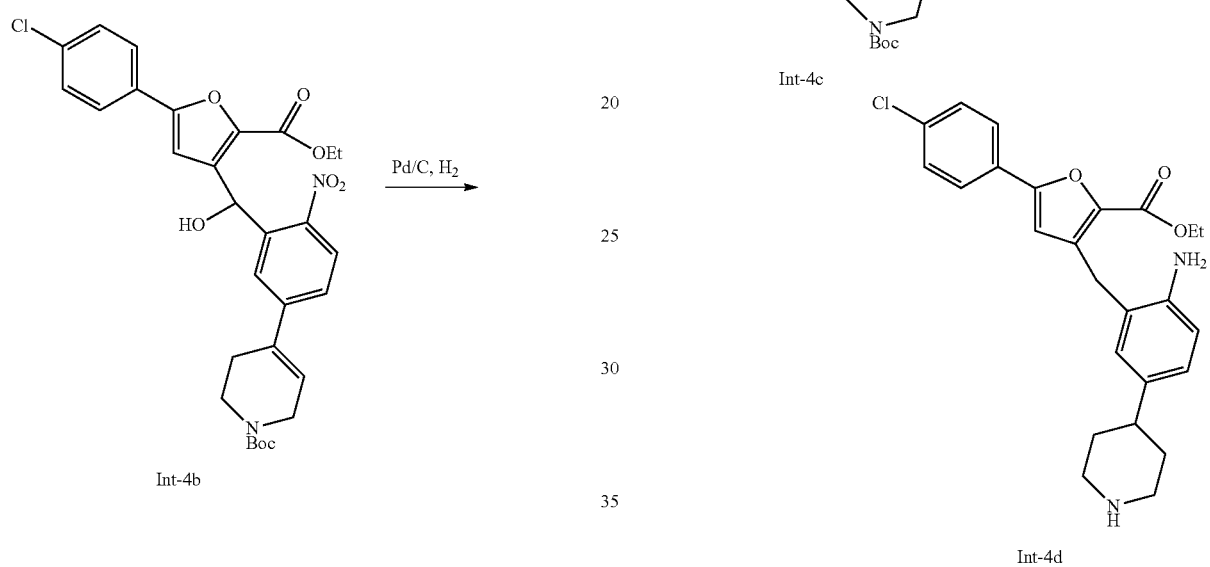

To a solution of Int-4-e (120g) in DCM (16 mL) was added triethylsilane (3.5 mL) and trifluoroacetic acid (1.6 mL). The combined reaction mixture was allowed to stir at 22° C. for 16 h. The resulting reaction mixture was concentrated in vacuo, and purified using an ISCO chromatography column in 0-20% (2N NH$_3$ in MeOH) in DCM to afford 0.63 g of Int-4-d.

Step E—Synthesis of Compound 15

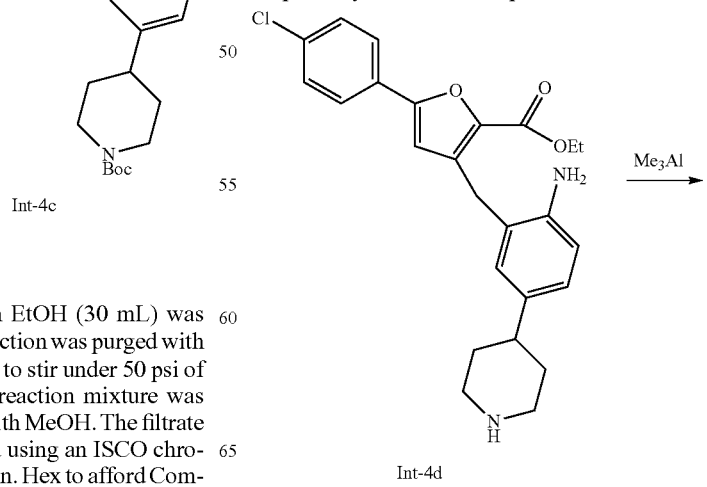

To a solution of Int-4-b (1.80 g) in EtOH (30 mL) was added 10% w/w Pd/C (360 mg). The reaction was purged with N$_2$ (3×), then with H$_2$ (3×) and allowed to stir under 50 psi of H$_2$ at 22° C. for 16 h. The resulting reaction mixture was filtered through Celite®, and washed with MeOH. The filtrate was concentrated in vacuo and purified using an ISCO chromatography column in 0-100% EtOAc in. Hex to afford Compound Int-4-c.

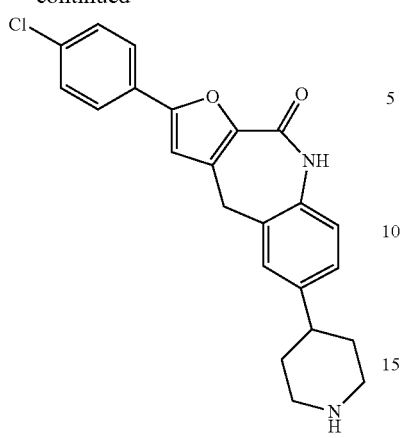

15

To a solution of Int-4-d (98 mg) in toluene (22 mL), purged with N₂, was added a 2 M solution of Me₃Al in hexanes (0.6 mL). The resulting reaction mixture was heated at 70° C. under N₂ for 8 h. The reaction was then quenched with sat. NaK tartrate (aq) and extracted with EtOAc (3×). The combined organics were dried over MgSO₄, filtered and concentrated in vacuo. The organic residue was purified by a Gilson reverse phase chromatography system to afford 22 mg of Compound 15 as the TFA salt.

Compounds, wherein $X^1$ is O in the compounds of Formula (I) such as 2-4, 6-8, 10-13, and 16-22 can be prepared using methods similar to those described in Examples 1-4. Compounds wherein $X^1$ is S in the compounds of Formula (I), such as compounds 23-27 can be prepared using methods similar to those described in Examples 1-4 from the corresponding thiophene starting materials. LC/MS data for compounds 1-27 is shown below in Table 1.

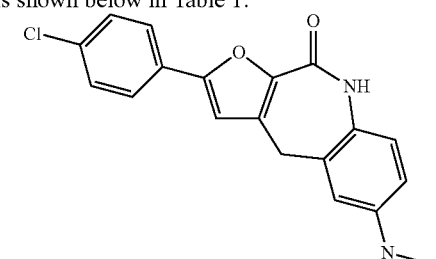

394.2 @ 3.52 min

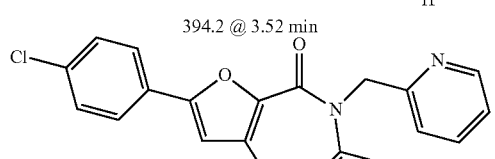

485.0 @ 2.70 min

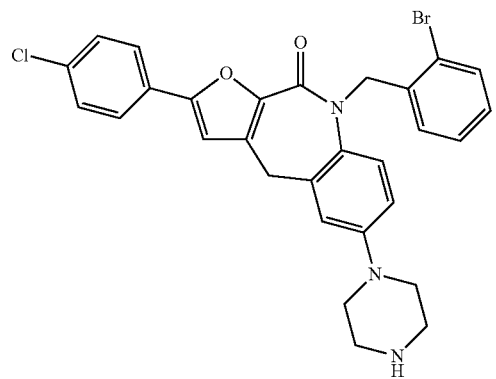

464.2 @ 4.51 min

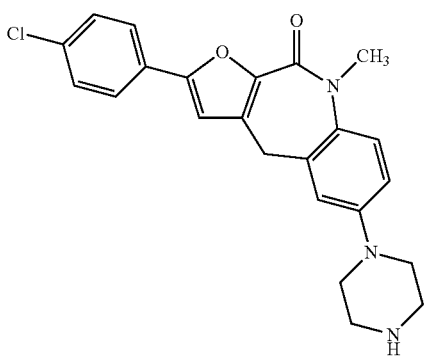

408.2 @ 3.84 min

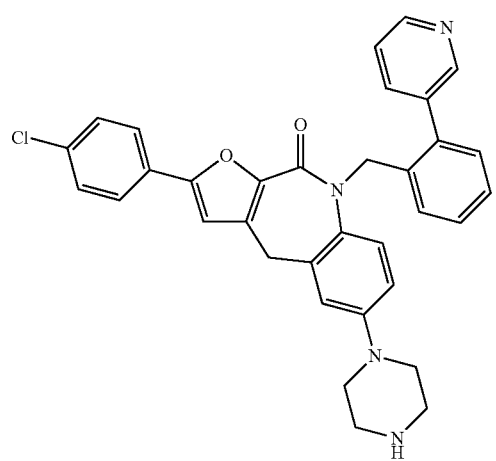

561.3 @ 3.45 min

-continued
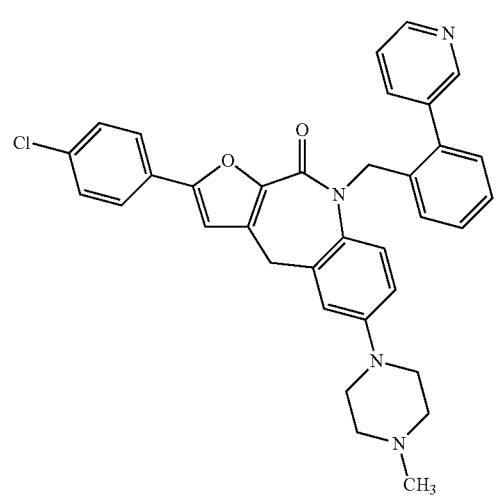
6
575.3 @ 3.57 min
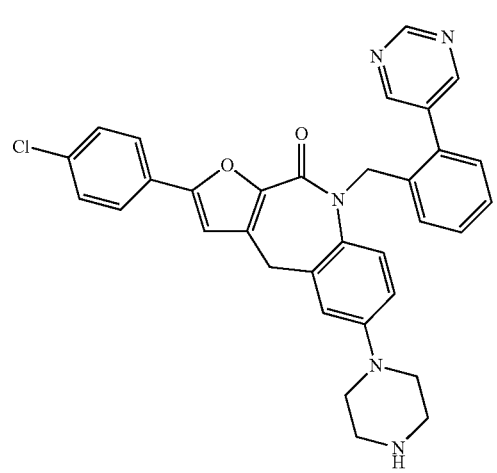
9
562.3 @ 3.18 min
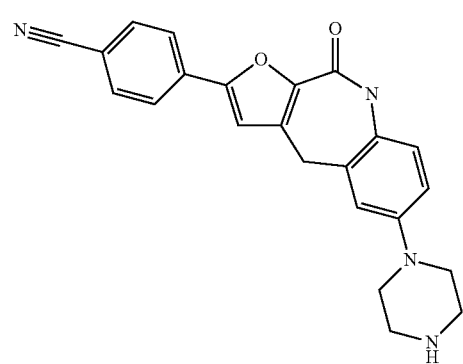
7
3.85 @ 2.89 min
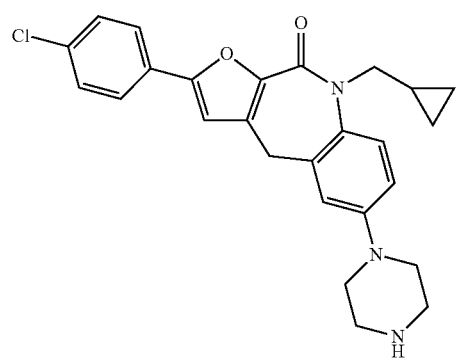
10
448.2 @ 2.43 min
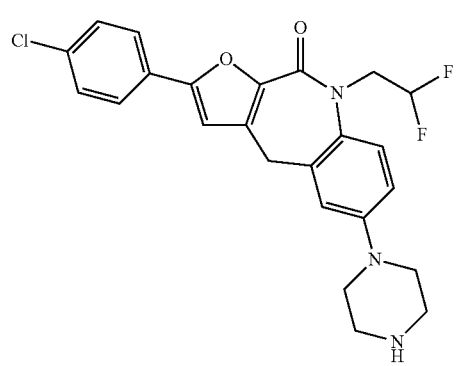
8
458.3 @ 3.79 min
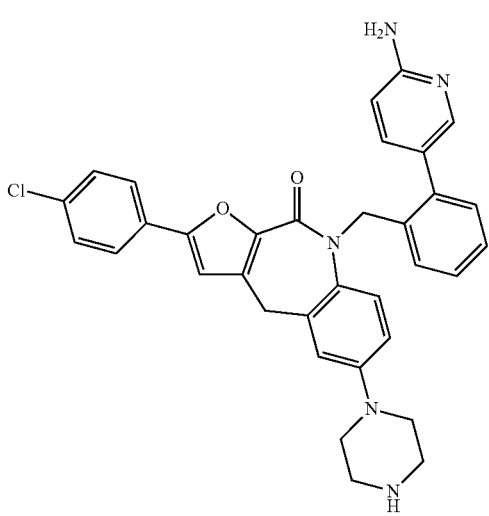
11
576.3 @ 3.63 min 12
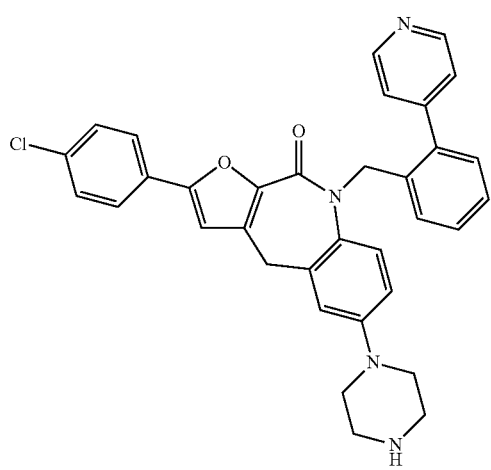
561.3 @ 2.04 min
13
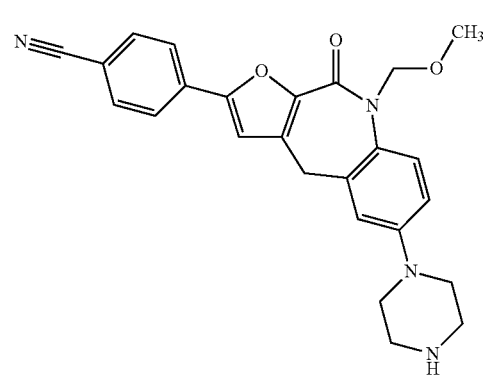
417.2 @ 1.79 min
14
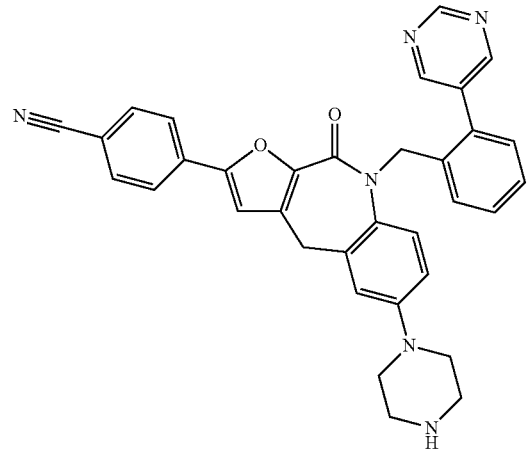
553.4 @ 1.88 min
15
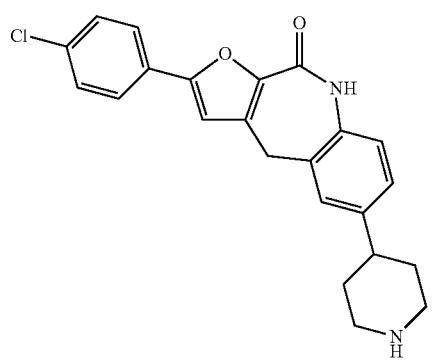
393.2 @ 2.08 min
16
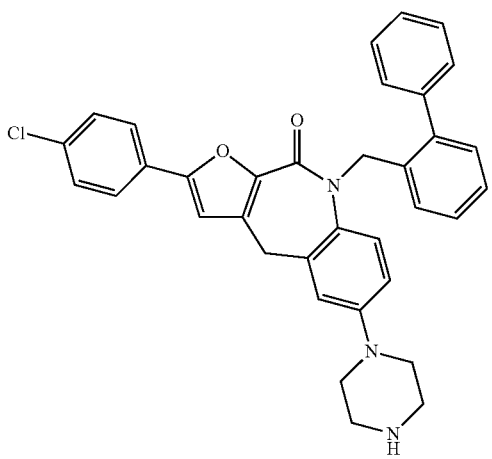
559.3 @ 2.98 min
17
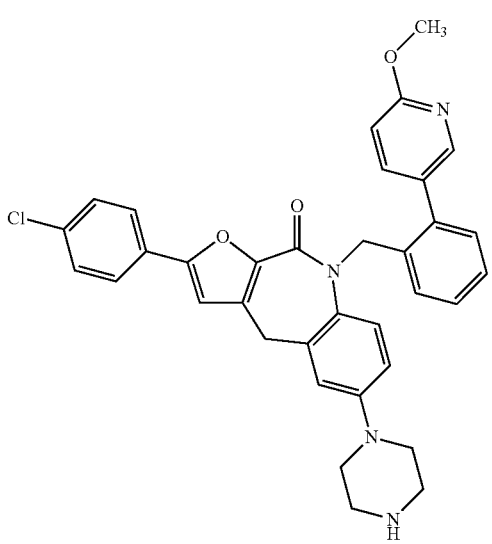
591.3 @ 4.41 min 18
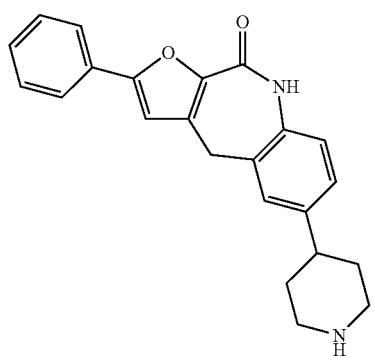
359.2 @ 1.84 min
19
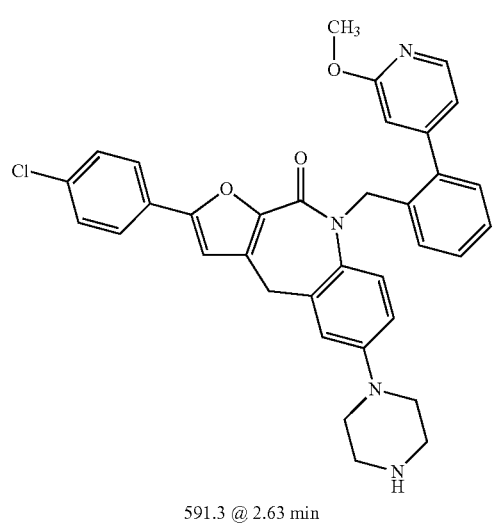
591.3 @ 2.63 min
20
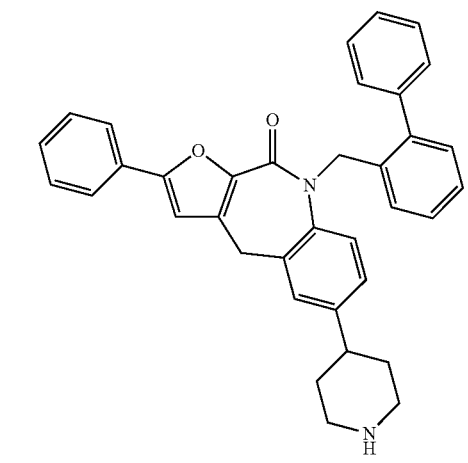
525.3 @ 2.73 min
21
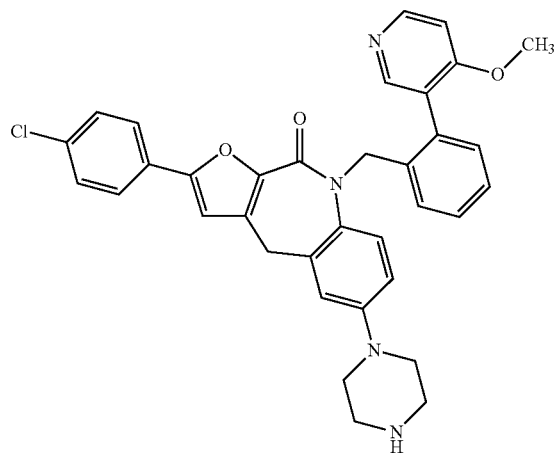
591.3 @ 2.01 min
22
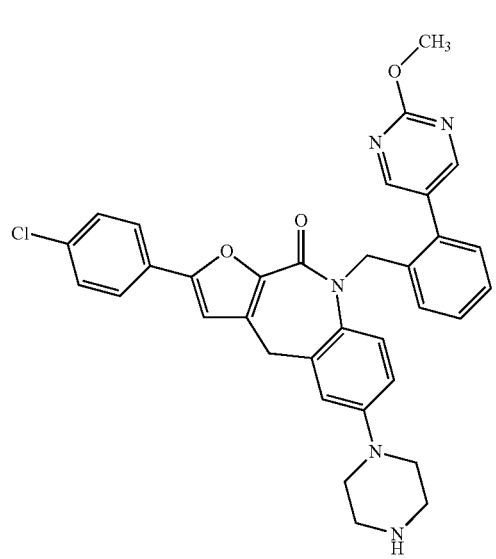
592.3 @ 2.47 min
23
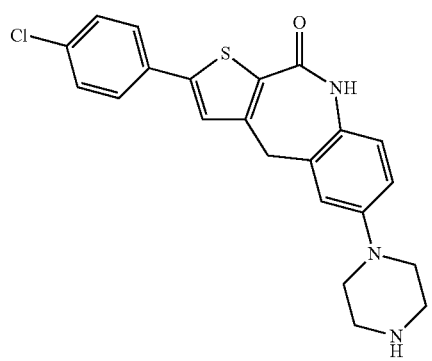
410.2 @ 3.66 min

24

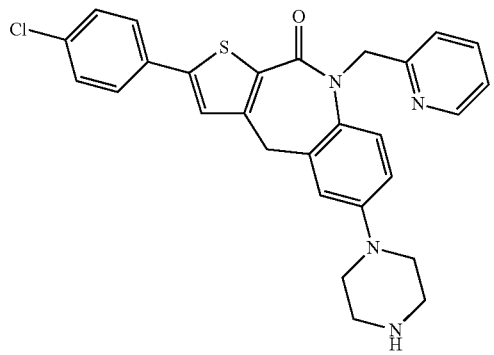

501.3 @ 2.50 min

25

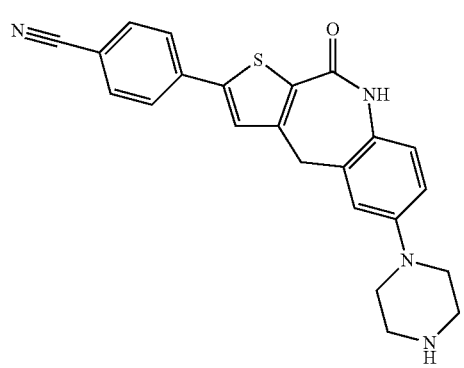

401.2 @ 3.12 min

26

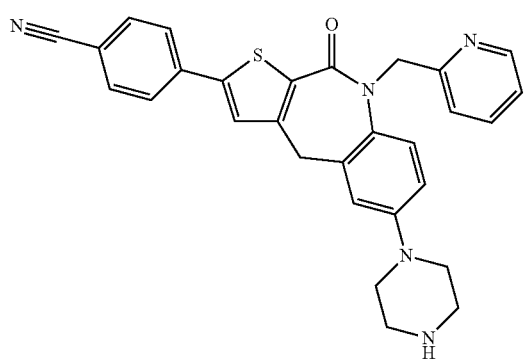

492.3 @ 2.24 min

27

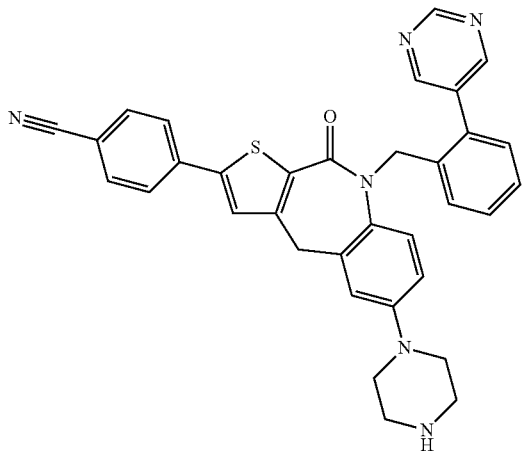

569.3 @ 2.87 min

Example 5

Preparation of Deuterated Intermediate Int-5b

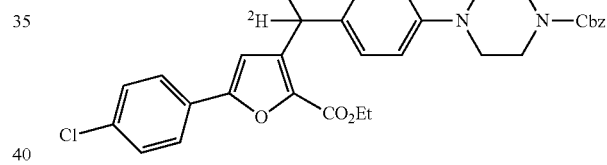

Int-5b

Compounds of the of the Formula (I) that incorporate deuterium atoms can be prepared from commercially available or known deuterium-containing reagents using modifications of the procedures described above. For instance, compounds of the Formula (I) which contain deuterium on ring B, i.e., wherein $R^{10}$ is $^2H$, can be prepared as shown in the scheme below.

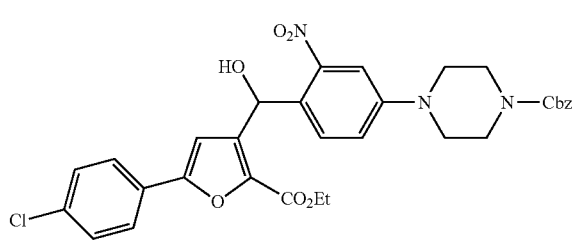

Int-1c

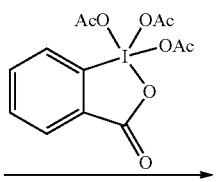

-continued

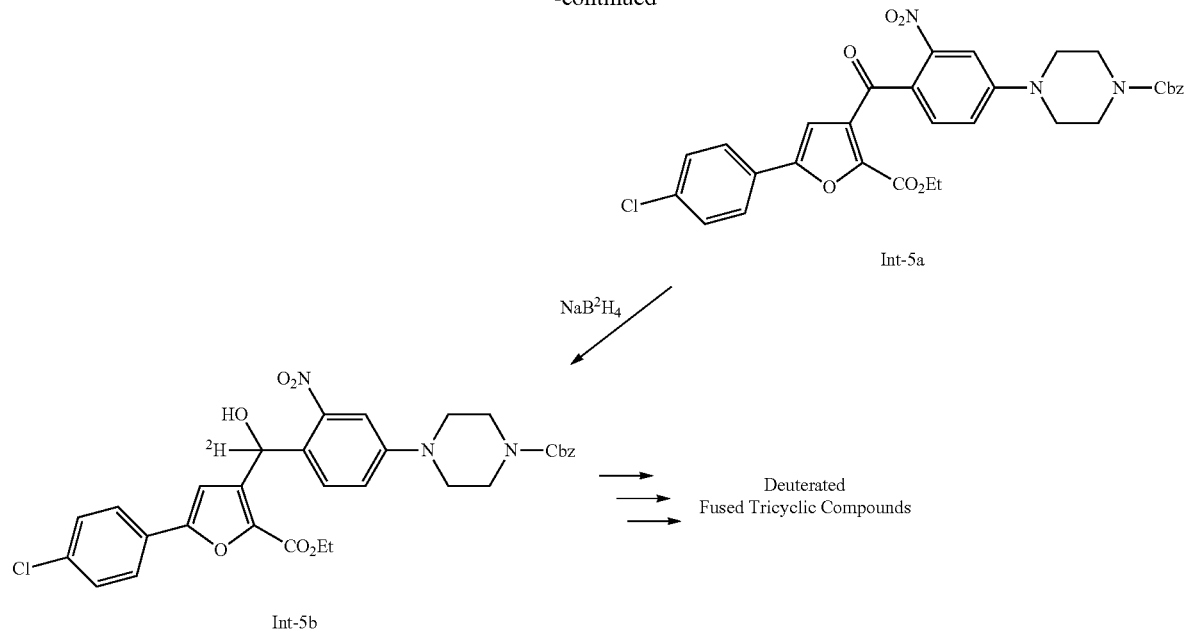

Int-1c from Example 1 is treated with the Dess-Martin periodinane reagent to provide the ketone Int-5a. Int-5a is treated with sodium borodeuteride to provide the deuterated intermediate Int-5b, which can be elaborated to the Fused Tricyclic Compounds using methods similar to those described in Examples 1-3.

Example 6

MK2 DELFIA Assay Protocol

All steps were carried out at room temperature. Active MK2 kinase (Millipore #14-337) was diluted into 2× reaction buffer* to prepare a 5 nM kinase concentration is combined in 96 well plates (Fisher # PC0198938) with a test compound prepared in 25% DMSO. Following a 15 minute pre-incubation, 20 microliters of 6 uM Acam peptide (1411B Autocam Biotinylated Peptide; Cell Signalling Technologies) was added and the reaction was allowed to proceed for 10 minutes. The reaction was terminated by transfer of 10 microliters into 190 microliters of DELFIA Assay buffer, 10 mM in EDTA (Perkin-Elmer #4002-0010) in Streptavidin plates (Roche Diagnostics Corp. #117347760001). After 1 hour of shaking the plates were washed (DELFIA wash buffer 4010-0010) and detection antibodies (Cell Signaling Technologies #9386; Perkin Elmer #AD0124) diluted into DELFIA Assay buffer were added to wells for 1 hour incubation. Following the antibody incubation the plates were washed a second time. Enhancement solution (Perkin Elmer#4001-0010) was added to the wells and after 10 minutes of shaking, activity (Europium fluorescence) was read on a Wallac Victor 1420 plate reader.

*FINAL REACTION BUFFER:
20 mM HEPES pH 7.3
50 mM NaCl
10 mM $MgCl_2$
1 mM dithiothreitol For MK2 enzymatic assays, concentration response curves were fitted by a sigmoidal regression with variable slope, and 50% inhibitory concentration ($IC_{50}$) values were derived by use of the Levenburg Marquardt algorithm utilizing a 4 parameter fit. The degree of MK2 inhibition was calculated from the amount of phosphorylated peptide generated in the presence of inhibitor compound compared to controls with no inhibitor in a 10 minute reaction. Basal MK2 activity was assessed in the presence of complete reaction mixtures containing a 10:1 ratio of ethylenediaminetetraacetic acid to magnesium chloride.

The $IC_{50}$ values for compounds 1 and 2 were determined in the MK2 delfia assay to be between 10 and 100 nM.

Example 7 bMK2 IMAP Assay Protocol

Assay Reagents:
5× Reaction Buffer T (Molecular Device, R7364)
10 mM ATP (New England, P0756S)
Substrate: TAMRA labeled Glycogen. Synthase-derived Peptide (5TAMRA-KKLNRTLSVA-COOH, Molecular Device, R7277)
5× Progressive Binding Buffer A (Molecular Device, R7279)
Progressive Binding Reagent (Molecular Device, R7281)
All the components of the MK2 phosphorylation reaction made as 4× concentrated in 1× Reaction Buffer T containing 10 mM Tris, pH 7.2, 10 mM $MgCl_2$, 1 mM DTT (freshly added), 0.05% azide and 0.01% Tween 20, and the reaction was carried out in a 384 well black reaction plate (Fisher, 09-761-85) at room temperature in the dark.

Reaction Setup
5 μl of 4× inhibitor in 4% DMSO, 5 μl of 400 μM ATP and 5 μl of 200 pM MK2 kinase were mixed and incubated for 30 min. The reaction was started by adding 5 ml of 400 nM TAMRA labeled peptide and incubating 30 min in dark. The final concentrations are: 1× inhibitor, 1% DMSO, 100 μM ATP, 50 pM MK2 and 100 nM substrate.

Detection
The reaction was stopped by adding 60 μl of 1:400 diluted Progressive Binding Reagent in 1× Progressive Binding Buffer A and incubating 30 min in the dark. The plate was read at an Analyst HT 96-384 Plate Reader (LJL BioSystem) equipped with Fluorescence Polarization module (Excitation wavelength 530 nm and Emission wavelength 580 nm).

Concentration response curves were fitted by a sigmoidal regression with variable slope, and 50% inhibitory concentration ($IC_{50}$) values were derived by use of PRISM® Version 4.0 (GraphPad, San Diego, Calif., USA). The degree of MK2 inhibition was calculated from the change in phosphorylated peptide generated in the presence of inhibitor compound added to each reaction followed by a 90 min reaction time. Basal MK2 activity was assessed in the absence of ATP which is required for enzymatic activity.

$IC_{50}$ values were determined for certain compounds of the present invention using the above-described method. $IC_{50}$ data for selected compounds of the present invention are provided below wherein A is 1-10 nM, B is 10-100 nM, and C is 100-1,000 nM, and D is 1,000-10,000 nM.

| No. | Structure | $IC_{50}$ Value |
|---|---|---|
| 1 | 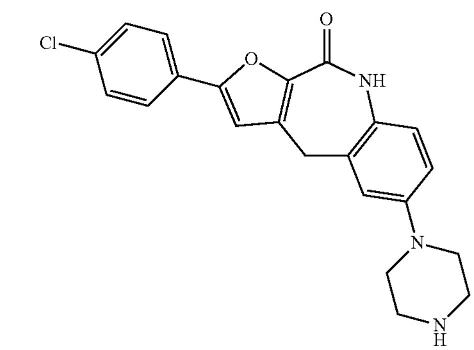 [SMILES: O=C1Nc2ccc(N3CCNCC3)cc2Cc2cc(-c3ccc(Cl)cc3)oc21] | B |
| 2 | 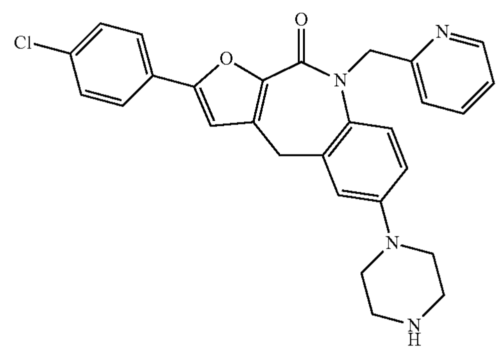 [SMILES: O=C1c2oc(-c3ccc(Cl)cc3)cc2Cc2cc(N3CCNCC3)ccc2N1Cc1ccccn1] | B |
| 3 | 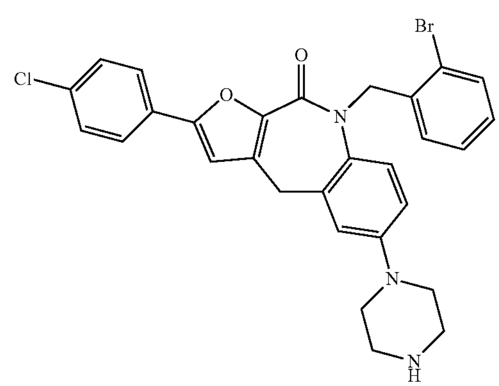 [SMILES: O=C1c2oc(-c3ccc(Cl)cc3)cc2Cc2cc(N3CCNCC3)ccc2N1Cc1ccccc1Br] | B |

-continued
| No. | Structure | IC$_{50}$ Value |
|---|---|---|
| 4 | 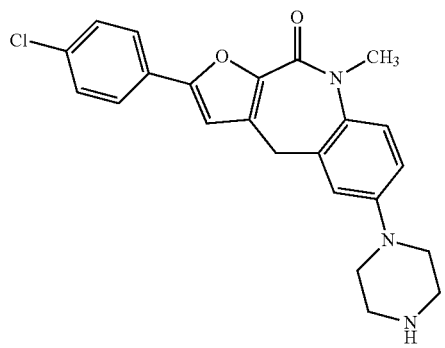 [SMILES: CN1C(=O)c2oc(-c3ccc(Cl)cc3)cc2Cc2cc(N3CCNCC3)ccc21] | B |
| 5 | 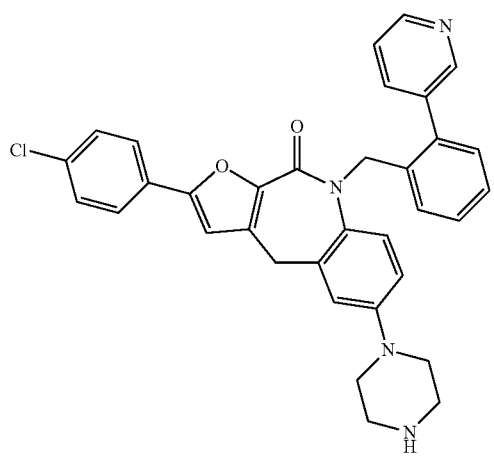 [SMILES: O=C1c2oc(-c3ccc(Cl)cc3)cc2Cc2cc(N3CCNCC3)ccc2N1Cc1ccccc1-c1cccnc1] | B |
| 6 | 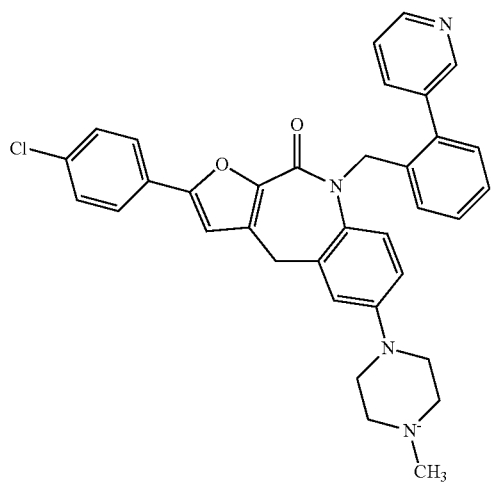 | B |

-continued
| No. | Structure | IC$_{50}$ Value |
|---|---|---|
| 7 | 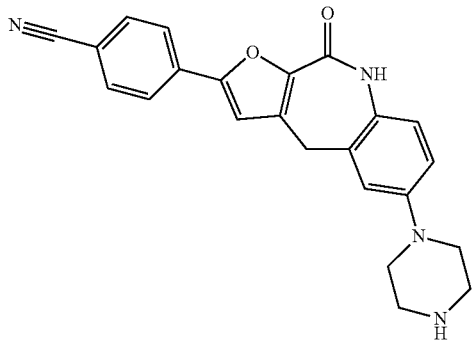 [SMILES: N#Cc1ccc(-c2cc3c(o2)C(=O)Nc2ccc(N4CCNCC4)cc2C3)cc1] | C |
| 8 | 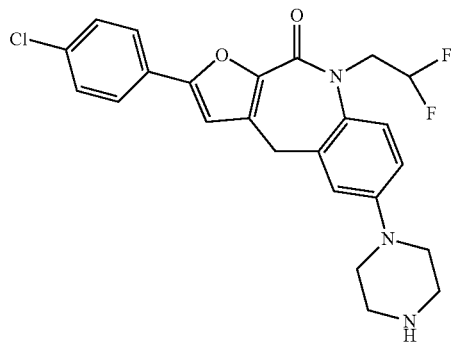 [SMILES: O=C1c2oc(-c3ccc(Cl)cc3)cc2Cc2cc(N3CCNCC3)ccc2N1CC(F)F] | C |
| 9 | 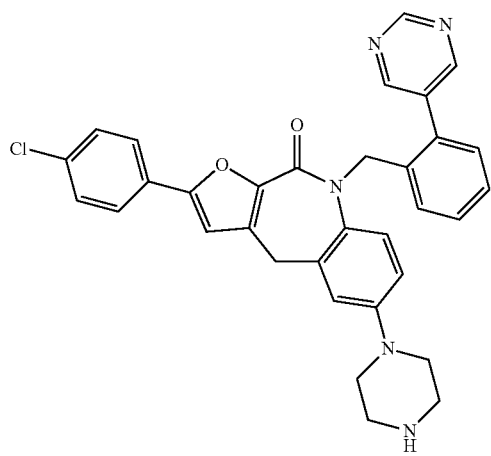 [SMILES: O=C1c2oc(-c3ccc(Cl)cc3)cc2Cc2cc(N3CCNCC3)ccc2N1Cc1ccccc1-c1cncnc1] | A |
| 10 | 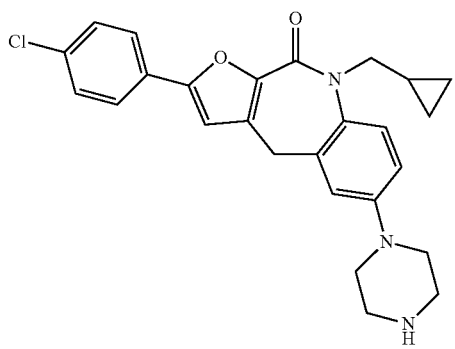 [SMILES: O=C1c2oc(-c3ccc(Cl)cc3)cc2Cc2cc(N3CCNCC3)ccc2N1CC1CC1] | C |

| No. | Structure | IC$_{50}$ Value |
|---|---|---|
| 11 | 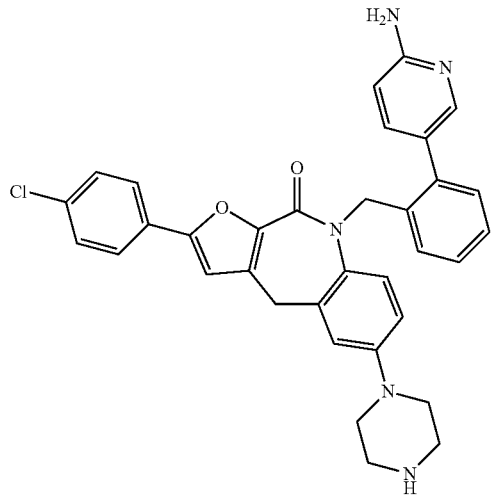 [SMILES: Nc1ccc(-c2ccccc2CN2C(=O)c3oc(-c4ccc(Cl)cc4)cc3Cc3cc(N4CCNCC4)ccc32)cn1] | B |
| 12 | 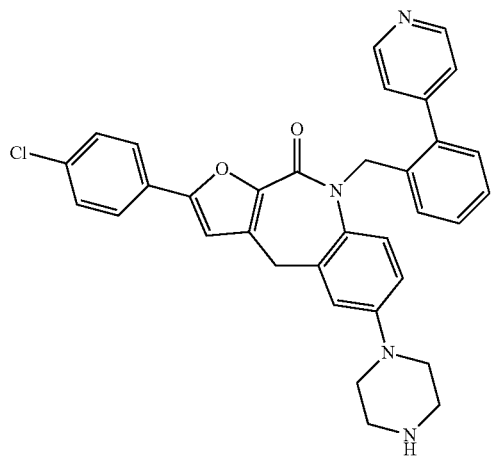 [SMILES: O=C1c2oc(-c3ccc(Cl)cc3)cc2Cc2cc(N3CCNCC3)ccc2N1Cc1ccccc1-c1ccncc1] | B |
| 13 | 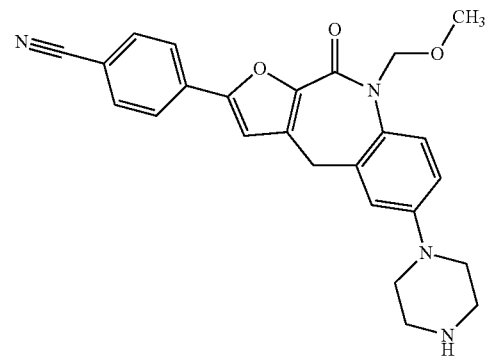 [SMILES: COCN1C(=O)c2oc(-c3ccc(C#N)cc3)cc2Cc2cc(N3CCNCC3)ccc21] | A |

-continued
| No. | Structure | IC$_{50}$ Value |
|---|---|---|
| 14 | 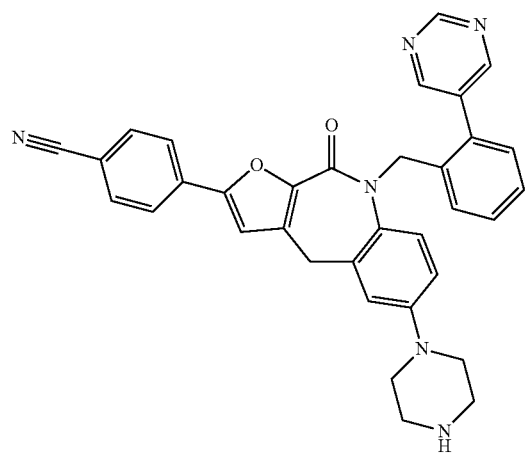 | A |
| 15 | 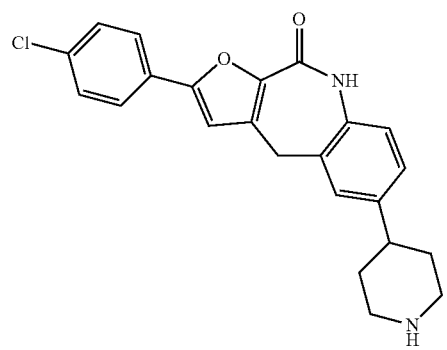 [SMILES: O=C1Nc2ccc(C3CCNCC3)cc2Cc2cc(-c3ccc(Cl)cc3)oc21] | B |
| 16 | 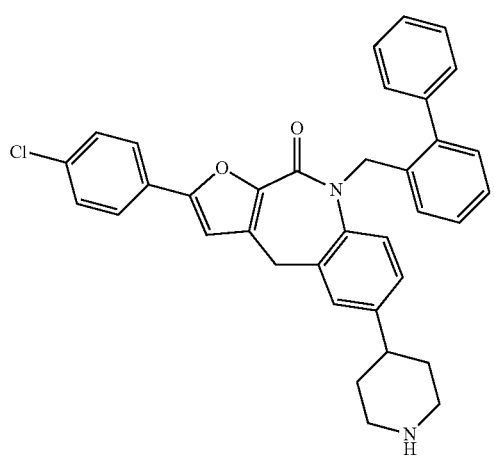 [SMILES: O=C1c2oc(-c3ccc(Cl)cc3)cc2Cc2cc(C3CCNCC3)ccc2N1Cc1ccccc1-c1ccccc1] | C |

-continued
| No. | Structure | IC50 Value |
|---|---|---|
| 17 | 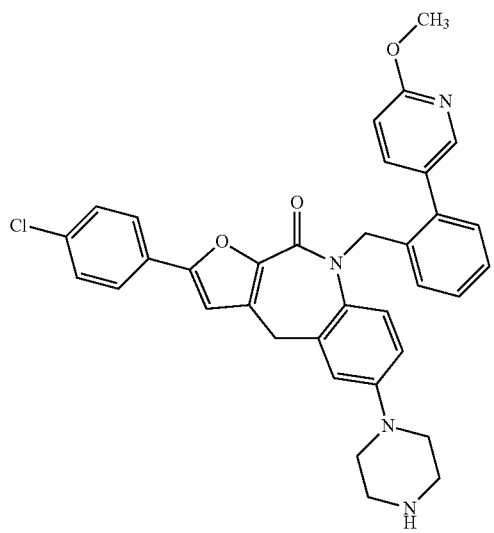 [SMILES: COc1ccc(-c2ccccc2CN2C(=O)c3oc(-c4ccc(Cl)cc4)cc3Cc3cc(N4CCNCC4)ccc32)cn1] | B |
| 18 | 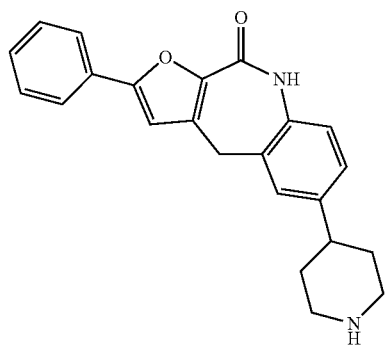 [SMILES: O=C1Nc2ccc(C3CCNCC3)cc2Cc2cc(-c3ccccc3)oc21] | C |
| 19 | 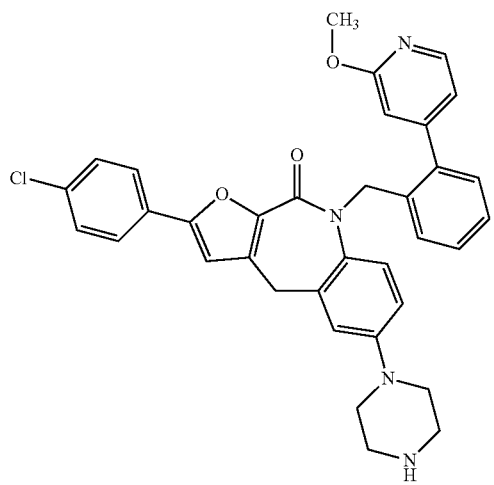 [SMILES: COc1cc(-c2ccccc2CN2C(=O)c3oc(-c4ccc(Cl)cc4)cc3Cc3cc(N4CCNCC4)ccc32)ccn1] | B |

-continued
| No. | Structure | IC$_{50}$ Value |
|---|---|---|
| 20 | 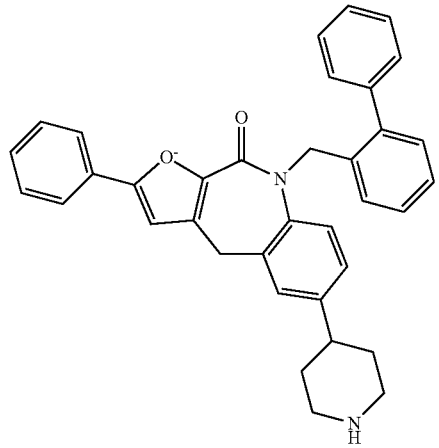 | D |
| 21 | 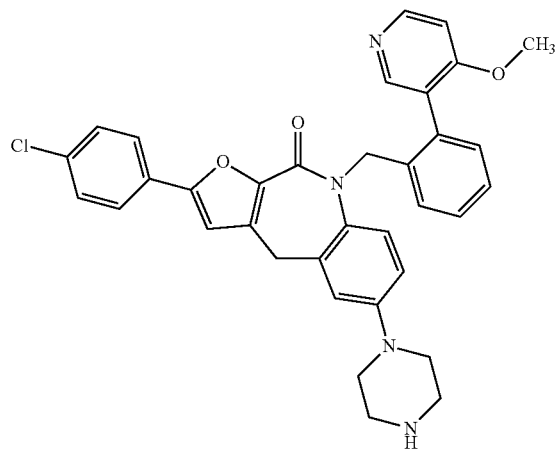 [SMILES: COc1ccncc1-c1ccccc1CN1C(=O)c2oc(-c3ccc(Cl)cc3)cc2Cc2cc(N3CCNCC3)ccc21] | B |
| 22 | 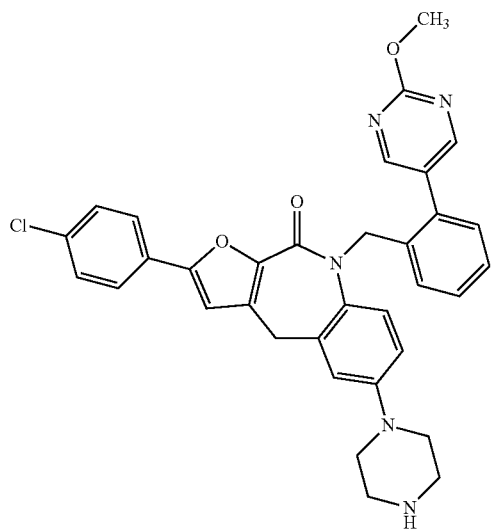 [SMILES: COc1ncc(-c2ccccc2CN2C(=O)c3oc(-c4ccc(Cl)cc4)cc3Cc3cc(N4CCNCC4)ccc32)cn1] | B |

-continued
| No. | Structure | IC$_{50}$ Value |
|---|---|---|
| 23 | 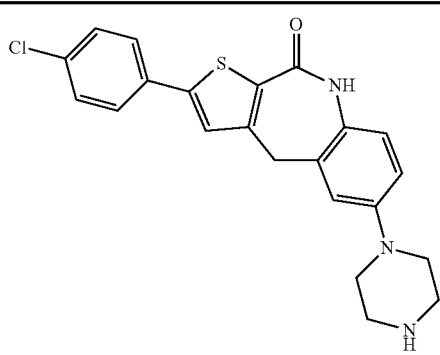 | D |
| 24 | 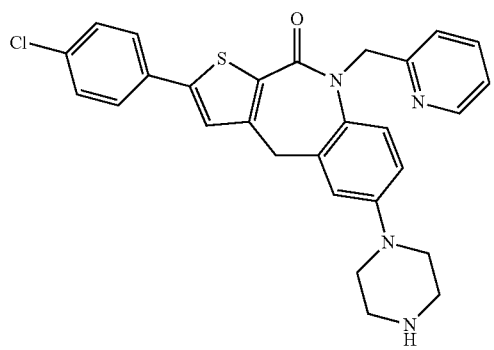 [SMILES: O=C1c2sc(-c3ccc(Cl)cc3)cc2Cc2cc(N3CCNCC3)ccc2N1Cc1ccccn1] | D |
| 25 | 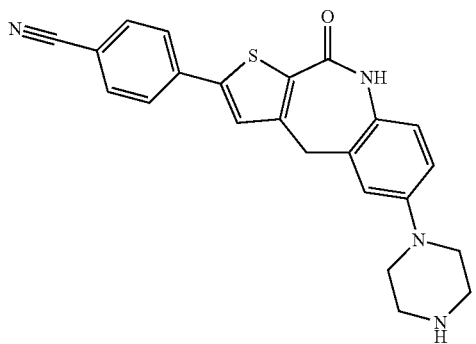 [SMILES: N#Cc1ccc(-c2cc3c(s2)C(=O)Nc2ccc(N4CCNCC4)cc2C3)cc1] | D |
| 26 | 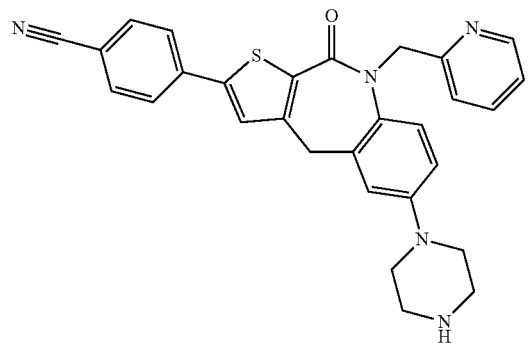 [SMILES: N#Cc1ccc(-c2cc3c(s2)C(=O)N(Cc2ccccn2)c2ccc(N4CCNCC4)cc2C3)cc1] | D |

| No. | Structure | IC$_{50}$ Value |
|---|---|---|
| 27 | 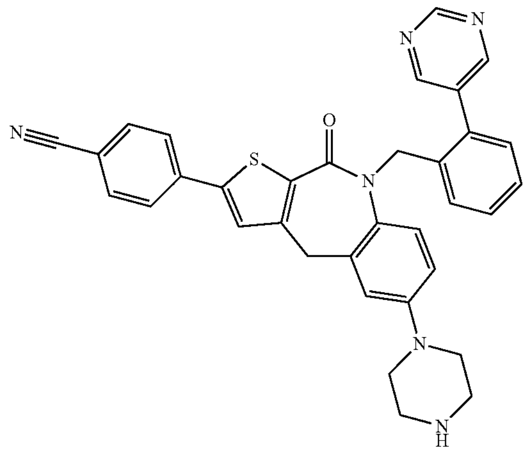 [SMILES: N#Cc1ccc(-c2cc3c(s2)C(=O)N(Cc2ccccc2-c2cncnc2)c2ccc(N4CCNCC4)cc2C3)cc1] | C |

Representative compounds of the invention had the following IC$_{50}$ values in the above-described assay: compound 5 (38.3 nM), compound 8 (107 nM), and compound 14 (2 nM).

Uses of the Fused Tricylic Compounds

The Fused Tricyclic Compounds are useful in human and veterinary medicine. The Fused Tricyclic Compounds are useful in a method of inhibiting the MK2 enzyme in a patient such as a mammal in need of such inhibition comprising the administration of an effective amount of the compound. The Fused Tricyclic Compounds are therefore useful to control, prevent, and/or treat conditions and diseases mediated by high or abnormal MK2 enzyme activity. For instance, the Fused Tricyclic Compounds can be administered to a patient in need of treatment for an inflammatory disorder.

The general value of the compounds of the invention in inhibiting, the activity of MK2 can be determined, for example, using the assays described above in Examples 6 and 7. Alternatively, the general value of the compounds in treating disorders and diseases for human and animal use may be established in industry standard animal models for demonstrating the efficacy of compounds in treating, for example, an anti-inflammatory disorder.

In one embodiment, the present invention provides a method of treating an anti-inflammatory disorder, which comprises administering to a patient in need of such treatment a therapeutically effective amount of a Fused Tricyclic Compound or a pharmaceutically salt thereof. In some instances, the anti-inflammatory disorder is selected from the group consisting of arthritis (e.g., rheumatoid arthritis, psoriatic arthritis, juvenile chronic arthritis, reactive arthritis, arthritis deformans, gouty arthritis, osteoarthritis, Lyme disease), inflammatory bowel disease, psoriasis, asthma, and chronic obstructive pulmonary disorder.

In another embodiment, the present invention provides a method of treating rheumatoid arthritis comprising administering to a patient in need of such treatment a therapeutically effective amount of a Fused Tricyclic Compound.

In another embodiment, the present invention provides a method of treating rheumatoid arthritis comprising administering to a patient in need of such treatment a therapeutically effective amount of a Fused Tricyclic Compound.

In yet another embodiment, the present invention provides a method of treating inflammatory bowel disease comprising administering to a patient in need of such treatment a therapeutically effective amount of a Fused Tricyclic Compound. For instance, the inflammatory bowel disease can be ulcerative colitis or Crohn's disease.

In another embodiment, the present invention provides a method of treating psoriasis comprising administering to a patient in need of such treatment a therapeutically effective amount of a Fused Tricyclic Compound. In some instances, the Fused Tricyclic Compound is administered topically to the patient.

In yet another embodiment, the present invention provides a method of treating asthma comprising administering to a patient in need of such treatment a therapeutically effective amount of a Fused Tricyclic Compound.

In another embodiment, the present invention provides a method of treating chronic obstructive pulmonary disorder comprising administering to a patient in need of such treatment a therapeutically effective amount of a Fused Tricyclic Compound.

In other embodiments the invention provides a method of treatment for a disorder selected from the group consisting of, acute synovitis, enterogenic spondyloarthropathies, ankylosing spondylitis, gastritis, pancreatitis, multiple sclerosis, lumbar spondylarthrosis, systemic lupus erythematosus, lupus nephritis, glomerulonephritis, polychondritis, scleroderma, Wegener granulomatosis, dermatomyositis, polymyositis, tendonitis and bursitis, graft- versus-host disease, sepsis, septic shock, Behcet's disease, uveitis (anterior and posterior), cutaneous lupus erythematosus, dermatitis, atopic dermatitis, contact dermatitis, eczema, xerosis, Sjogrens syndrome, atherosclerosis, myocarditis, inflammatory pain, cachexia or wasting syndrome associated with morbid TNF release (e.g., consequent to infection, cancer or organ dysfunction, especially AIDS-related cachexia), and bronchitis, comprising administering to a patient in need of such treatment a therapeutically effective amount of a Fused Tricyclic Compound.

In yet another embodiment, the present invention provides a method of treating cancer comprising administering to a patient in need of such treatment, a therapeutically effective amount of a Fused Tricylic Compound. In certain instances, the Fused Tricyclic Compounds are useful in the treatment of cancers and metastases thereof, including (but not limited to)

the following: carcinoma, including that of the bladder, breast, colon, kidney, liver, lung, including small cell lung cancer, non-small cell lung cancer, head and neck, esophagus, gall bladder, ovary, pancreas, stomach, cervix, thyroid, prostate, and skin, including squamous cell carcinoma; hematopoietic tumors of lymphoid lineage, including leukemia, acute lymphocytic leukemia, chronic lymphocytic leukemia, acute lymphoblastic leukemia, B-cell lymphoma, T- cell lymphoma, Hodgkins lymphoma, non-Hodgkins lymphoma, hairy cell lymphoma, mantle cell lymphoma, myeloma, and Burkett's lymphoma; hematopoietic tumors of myeloid lineage, including acute and chronic myelogenous leukemias, myelodysplastic syndrome and promyelocytic leukemia; tumors of mesenchymal origin, including fibrosarcoma and rhabdomyosarcoma; tumors of the central and peripheral nervous system, including brain tumors such as an astrocytoma, a neuroblastoma, a glioma (such as glioblastoma multiforme) or a schwannoma; and other tumors, including melanoma, seminoma, teratocarcinoma, osteosarcoma, xenoderoma pigmentosum, keratoctanthoma, thyroid follicular cancer and Kaposi's sarcoma. The Fused Trricyclic Compounds are useful for treating primary and/or metastatic tumors.

In some embodiments of the methods described above, a therapeutically effective amount of a pharmaceutically acceptable salt of the Fused Tricyclic Compound is administered to the patient. In other specific embodiments, the Fused Tricyclic Compound itself is administered to the patient, and not a salt thereof.

Combination Therapy

In another embodiment, the present methods for treating or preventing an anti-inflammatory disorder or cancer can further comprise the administration of one or more additional therapeutic agents which are not Fused Tricyclic Compounds.

The Fused Tricyclic Compounds may be used in combination with one or more additional therapeutic agents in the treatment, prevention, suppression or amelioration of diseases or conditions for which the Fused Tricyclic Compounds or the other agents may have utility, where the combination of the drugs together are safer or more effective than either agent alone. Such additional therapeutic agent(s) may be administered, by a route and in an amount commonly used therefore, contemporaneously or sequentially with a Fused Tricyclic Compound. When a Fused Tricyclic Compound is used contemporaneously with one or more additional therapeutic agents, a pharmaceutical composition in unit dosage form containing such additional therapeutic agents and the Fused Tricyclic Compound is preferred. However, the combination therapy may also include therapies in which the Fused Tricyclic Compound and one or more additional therapeutic agents are administered on different overlapping schedules. In some embodiments, when used in combination with one or more additional therapeutic agents, the Fused Tricyclic Compounds and the additional therapeutic agents may be used in lower doses than when each is used singly.

Accordingly, as discussed further below, the pharmaceutical compositions of the present invention include those that contain one or more additional therapeutic agents, in addition to a Fused Tricyclic Compound.

For treating anti-inflammatory disorders or disorders wherein inappropriate levels of cytokines are implicated (e.g., TNF-α), the Fused Tricyclic Compounds can be administered with one or more suitable additional therapeutic agents selected from the following classes of agents: anti cytokine and anti-cytokine receptor agents (e.g., TNF-α blockers such as infliximab or etanercept), disease-modifying anti-rheumatic agents (DMARDs) (e.g., methotrexate, leflunomide, sulfasalazine); and non-steroidal anti-inflammatories such as cyclooxygenase inhibitors.

For treating cancer, the Fused Tricylic Compounds can be administered in combination with an additional therapeutic agent which is an anticancer agent (also known as a an antineoplastic agent). Non-limiting examples of anticancer agents (suitable for use in combination with the Fused Tricyclic Compounds include cytostatic agents, cytotoxic agents (such as for example, but not limited to, DNA interactive agents (such as cisplatin or doxorubicin)); taxanes (e.g., taxotere, taxol); topoisomerase II inhibitors (such as etoposide or teniposide); topoisomerase I inhibitors (such as irinotecan (or CPT-11), camptostar, or topotecan); tubulin interacting agents (such as paclitaxel, docetaxel or the epothilones); hormonal agents (such as tamoxifen); thymidilate synthase inhibitors (such as 5-fluorouracil); anti-metabolites (such as methoxtrexate); alkylating agents (such as temozolomide (TEMODAR™ from Schering-Plough Corporation, Kenilworth, N.J.), cyclophosphamide); farnesyl protein transferase inhibitors (such as, SARASAR™ (4-[2-[4-[(11R)-3,10-dibromo-8-chloro-6,11-dihydro-5H-benzo[5,6]cyclohepta[1, 2-b]pyridin-11-yl-]-1-piperidinyl]-2-oxoethyl]-1-piperidinecarboxamide, or SCH 66336 from Schering- Corporation, Kenilworth, N.J.), tipifamib (Zarnestra® or R115777 from Janssen Pharmaceuticals), L778,123 (a farnesyl protein transferase inhibitor from Merck & Company, Whitehouse Station, N.J.), BMS 214662 (a farnesyl protein transferase inhibitor from Bristol-Myers Squibb Pharmaceuticals, Princeton, N.J.); signal transduction inhibitors (such as, Iressa (from Astra Zeneca Pharmaceuticals, England), Tarceva (EGFR kinase inhibitors), antibodies to EGFR (e.g., C225), GLEEVEC™ (C-abl kinase inhibitor from Novartis Pharmaceuticals, East Hanover, N.J.); interferons such as, for example, intron (from Schering-Plough Corporation), Peg-Intron (from Schering-Plough Corporation); hormonal therapy combinations; aromatase combinations; ara-C, adriamycin, cytoxan, and gemcitabine.

Other anticancer agents useful as additional therapeutic agents include but are not limited to uracil mustard, chlormethine, ifosfamide, melphalan, chlorambucil, pipobroman, triethylenemelamine, ara-C, adriamycin, cytoxan, clofarabine (Clolar® from Genzyme Oncology, Cambridge, Mass.), cladribine (Leustat® from Janssen-Cilag Ltd.), aphidicolon, rituxan (from Genentech/Biogen Idec), sunitinib (Sutent® from Pfizer), dasatinib (or BMS-354825 from Bristol-Myers Squibb), tezacitabine (from Aventis Pharma), Sml1, fludarabine (from Trigan Oncology Associates), pentostatin (from BC Cancer Agency), triapine (from Vion Pharmaceuticals), didox (from Bioseeker Group), trimidox (from ALS Therapy Development Foundation), amidox, 3-AP (3-aminopyridine-2-carboxaldehyde thiosemicarbazone), and MDL-101,731 ((E)-2'-deoxy-2'-(fluoromethylene)cytidine).

Other useful additional anticancer agents include but are not limited to triethylenethiophosphoramine, busulfan, carmustine, lomustine, streptozocin, dacarbazine, floxuridine, cytarabine, 6-mercaptopurine, 6-thioguanine, fludarabine phosphate, leucovirin, oxaliplatin (ELOXATIN™ from Sanofi-Synthelabo Pharmaceuticals, France), vinblastine, vincristine, vindesine, bleomycin, dactinomycin, daunorubicin, epirubicin, idarubicin, mithramycin, deoxycoformycin, mitomycin-C, L-asparaginase, teniposide 17α-ethinylestradiol, diethylstilbestrol, testosterone, prednisone, fluoxymesterone, dromostanolone propionate, testolactone, megestrolacetate, methylprednisolone, methyltestosterone, prednisolone, triamcinolone, chlorotrianisene, hydroxyprogesterone, aminoglutethimide, estramustine, medroxyprogesteroneacetate, leuprolide, flutamide, toremifene, goserelin, carboplatin, hydroxyurea, amsacrine, procarbazine, mitotane, mitoxantrone, levamisole, navelbene, anastrazole, letrazole, capecitabine, reloxafine, droloxafine, hexamethylmelamine, avastin, herceptin, bexxar, velcade, zevalin, trisenox, xeloda, vinorelbine, profimer, erbitux, thiotepa, altretamine, trastuzumab, lerozole, fulvestrant, exernestane, fulvestrant, ifosfomide, C225 and campath.

When administering an additional therapeutic agent in combination with a Fused Tricyclic Compound, the weight ratio of the Fused Tricyclic Compound to the additional therapeutic agent may be varied and will depend upon the effective dose of each agent. Generally, a therapeutically effective dose of each will be used. Thus, for example, when a Fused Tricyclic Compound is combined with an additional therapeutic agent, the weight ratio of the Fused Tricyclic Compound to the additional agent will generally range from about 1000:1 to about 1:1000, preferably about 200:1 to about 1:200. Combinations of a Fused Tricyclic Compound and additional therapeutic agents will generally also be within the aforementioned range, but in each case, an effective dose of each active ingredient should be used.

Compositions and Administration

This invention is also directed to pharmaceutical compositions which comprise at least one Fused Tricyclic Compound, or a pharmaceutically acceptable salt of said compound and at least one pharmaceutically acceptable carrier.

When administered to a patient, the Fused. Tricyclic Compounds can be administered as a component of a composition that comprises a pharmaceutically acceptable carrier or vehicle. The present invention provides pharmaceutical compositions comprising an effective amount of at least one Fused Tricyclic Compound and a pharmaceutically acceptable carrier. In the pharmaceutical compositions and methods of the present invention, the active ingredients will typically be administered in admixture with suitable carrier materials suitably selected with respect to the intended form of administration, i.e., oral tablets, capsules (either solid-filled, semi-solid filled or liquid filled), powders for constitution, oral gels, elixirs, dispersible granules, syrups, suspensions, and the like, and consistent with conventional pharmaceutical practices. Examples of pharmaceutically acceptable carriers and methods of manufacture for various compositions may be found in A. Gennaro (ed.), *Remington's Pharmaceutical Sciences,* 18$^{th}$ Edition, (1990), Mack Publishing Co., Easton, Pa. For example, for oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Solid form preparations include powders, tablets, dispersible granules, capsules, cachets and suppositories. Powders and tablets may be comprised of from about 0.5 to about 95 percent inventive composition. Tablets, powders, cachets and capsules can be used as solid dosage forms suitable for oral administration.

Moreover, when desired or needed, suitable binders, lubricants, disintegrating agents and coloring agents may also be incorporated in the mixture. Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum, and the like. Sweetening and flavoring agents and preservatives may also be included where appropriate.

Liquid form preparations include solutions, suspensions and emulsions and may include water or water-propylene glycol solutions for parenteral injection.

Liquid form preparations may also include solutions for intranasal administration.

Liquid form preparations may include compositions suitable for topical applications, such as are used for dermatological applications.

Aerosol preparations suitable for inhalation may include solutions and solids in powder form, which may be in combination with a pharmaceutically acceptable carrier, such as an inert compressed gas.

Also included are solid form preparations which are intended to be converted, shortly before use, to liquid form preparations for either oral or parenteral administration. Such liquid forms include solutions, suspensions and emulsions.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

The Fused Tricyclic Compounds of the present invention may also be delivered transdermally. The transdermal compositions can take the form of creams, lotions, aerosols, foams and/or emulsions and can be included in a transdermal patch of the matrix or reservoir type as are conventional in the art for this purpose.

Additionally, the compositions of the present invention may be formulated in sustained release form to provide the rate controlled release of any one or more of the components or active ingredients to optimize therapeutic effects, i.e., anti-cancer activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

In one embodiment, the Fused Tricyclic Compound is administered orally.

In another embodiment, the Fused Tricyclic Compound is administered intravenously.

In still another embodiment, the Fused Tricyclic Compound is administered sublingually.

In another embodiment, the Fused Tricyclic Compound is administered topically, for example, for use in treating psoriasis. Typically, in such embodiments, the Fused Tricyclic Compound is a component of topical composition which can take the form of solutions, salves, creams, ointments, in liposomal formulations, sprays, gels, lotions, aerosols, foams, or emulsions. Such topical compositions can be administered using a patch, e.g., of the matrix type, as are conventional in the art for this purpose.

In one embodiment, a pharmaceutical preparation comprising at least one Fused Tricyclic Compound is in unit dosage form. In such form, the preparation is subdivided into unit doses containing effective amounts of the active components.

Compositions can be prepared according to conventional mixing, granulating or coating methods, respectively, and the present compositions can contain, in one embodiment, from about 0.1% to about 99% of the Fused Tricyclic Compound (s) by weight or volume. In various embodiments, the present compositions can contain, in one embodiment, from about 1% to about 70% or from about 5% to about 60% of the Fused Tricyclic Compound(s) by weight or volume.

The quantity of the Fused Tricyclic Compound in a unit dose of preparation may be varied or adjusted from about 1 mg to about 2500 mg. In various embodiments, the quantity is from about 10 mg to about 1000 mg, 1 mg to about 500 mg, 1 mg to about 100 mg, and 1 mg to about 50 mg.

For convenience, the total daily dosage may be divided and administered in portions during the day if desired. In one embodiment, the daily dosage is administered in one portion. In another embodiment, the total daily dosage is administered in two divided doses over a 24 hour period. In another embodiment, the total daily dosage is administered in three divided doses over a 24 hour period. In still another embodiment, the total daily dosage is administered in four divided doses over a 24 hour period.

The amount and frequency of administration of the Fused Tricyclic Compounds and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 0.01 mg/day to about 2000 mg/day of the Fused Tricyclic Compounds. In one embodiment, a daily dosage regimen for oral administration is from about 1 mg/day to 1000 mg/day. In another embodiment, a daily dosage regimen for oral administration is from about 1 mg/day to 500 mg/day. In another embodiment, a daily dosage regimen for oral administration is from about 100 mg/day to 500 mg/day. In another embodiment, a daily dosage regimen for oral administration is from about 1 mg/day to 250 mg/day. In another embodiment, a daily dosage regimen for oral administration is from about 100 mg/day to 250 mg/day. In still another embodiment, a daily dosage regimen for oral administration is from about 1 mg/day to 100 mg/day. In still another embodiment, a daily dosage regimen for oral administration is from about 50 mg/day to 100 mg/day. In a further embodiment, a daily dosage regimen for oral administration is from about 1 mg/day to 50 mg/day. In another embodiment, a daily dosage regimen for oral administration is from about 25 mg/day to 50 mg/day. In a further embodiment, a daily dosage regimen for oral administration is from about 1 mg/day to 25 mg/day. The daily dosage may be administered in a single dosage or can be divided into from two to four divided doses.

For topical administration, such as may be used for the treatment of psoriasis, the dose of the Fused Tricyclic Compound will vary, but typically the compound will be present in a pharmaceutically acceptable composition in an amount of from about 0.01 to 50 w/w %, and more typically from about 0.1 to 10 w/w %. In some embodiments, the formulation may be applied to the affected area from 1 to 4 times daily.

The compositions of the invention can further comprise one or more additional therapeutic agents, selected from those listed above herein. Accordingly, in one embodiment, the present invention provides compositions comprising: (i) at least one Fused Tricyclic Compound or a pharmaceutically acceptable salt thereof; (ii) one or more additional therapeutic agents that are not a Fused Tricyclic Compound; and (iii) a pharmaceutically acceptable carrier, wherein the amounts in the composition are together effective to treat disease or disorder associated with inflammation or cancer.

Kits

Another aspect of this invention is a kit comprising a therapeutically effective amount of at least one Fused Tricyclic Compound, or a pharmaceutically acceptable salt of said compound and a pharmaceutically acceptable carrier, vehicle or diluent.

Yet another aspect of this invention is a kit comprising an amount of at least one Fused Tricyclic Compound, or a pharmaceutically acceptable of said compound and an amount of at least one additional therapeutic agent listed above, wherein the amounts of the two or more active ingredients result in a desired therapeutic effect. In one embodiment, the at least one Fused Tricyclic Compound and the at least one additional therapeutic agent are provided in the same container. In one embodiment, the at least one Fused. Tricyclic Compound and the at least one additional therapeutic agent are provided in separate containers.

Another aspect of this invention is a kit containing the at least one Fused Tricyclic Compound (and any additional therapeutic agents) packaged for retail distribution (i.e., an article of manufacture or a kit). Such articles will be labeled and packaged in a manner to instruct the patient how to use the product. Such instructions will include the condition to be treated, duration of treatment, dosing schedule, etc.

The present invention is not to be limited by the specific embodiments disclosed in the examples that are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

A number of references have been cited herein, the entire disclosures of which are incorporated herein by reference.

What is claimed is:
1. A compound of the Formula (I)

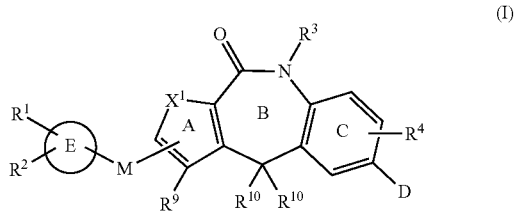

or a pharmaceutically acceptable salt thereof, wherein

E is phenyl, or is a monocyclic or bicyclic heteroaryl ring containing five to 10 ring atoms, wherein said heteroaryl ring contains from one to four heteroatoms selected from the group consisting of N, O, and S;

$R^1$ and $R^2$ are independently present or absent, and if present, are independently $(C_1-C_6)$ alkyl, halo, $(C_1-C_6)$ alkoxy, —CN, $(C_1-C_6)$ haloalkyl, azido, —C(=O)—$(C_1-C_6)$alkyl, —S(O)—$(C_1-C_6)$alkyl, or —S(O)$_2$—$(C_1-C_6)$alkyl, amino, $(C_1-C_6)$ alkylamino, di$(C_1-C_6)$alkylamino, carbamyl, —NH—C(=O)—$(C_1-C_6)$ alkyl, or hydroxyl;

M is —O—, —S(O)—, —S(O)$_2$—, $(C_1-C_4)$ alkylene, $(C_1-C_4)$ alkenylene, $(C_1-C_4)$alkynylene, fluoro$(C_1-C_4)$alkylene, hydroxy$(C_1-C_4)$alkylene, or alkoxy$(C_1-C_4)$alkylene;

or M is absent, such that E is bonded directly to ring A;

$X^1$ is O or S;

$R^9$ is H, $(C_1-C_6)$ alkyl, or halo;

each occurrence of $R^{10}$ is independently H, $(C_1-C_3)$ alkyl, fluoro, $(C_1-C_3)$ fluoroalkyl, or $(C_1-C_3)$ alkoxy;

$R^3$ is H, $(C_1-C_6)$ alkyl, $(C_1-C_6)$ haloalkyl, or $(C_1-C_6)$alkoxy $(C_1-C_6)$alkyl, or $R^3$ is a group of the formula -J-K, wherein J is $(C_1-C_3)$ alkylene, —C(=O)—, or —C(=S)—;

K is $(C_3-C_{10})$ cycloalkyl, $(C_6-C_{10})$ aryl, 5- to 6-membered heteroaryl, or 5- to 6-membered heterocyclyl, wherein said cycloalkyl, aryl, heteroaryl, or heterocyclyl of K is unsubstituted or substituted with one to four moieties, wherein said moieties are the same or different, and wherein said moieties are selected from the group consisting of $(C_1-C_6)$ alkyl, $(C_1-C_6)$ alkoxy, $(C_1-C_6)$ haloalkyl, halo, amino, $(C_1-C_6)$ alkylamino, di$(C_1-C_6)$alkylamino, —CN, —OCF$_3$, and $R^{25}$;

$R^{25}$ is $(C_6-C_{10})$ aryl or 5- to 6-membered heteroaryl, wherein said aryl or heteroaryl of $R^{25}$ is unsubstituted or substituted with one to four moieties, wherein said moieties are selected from the group consisting of $(C_1-C_6)$ alkyl, hydroxyl, $(C_1-C_6)$ alkoxy, halo, amino, $(C_1-C_6)$ alkylamino, di$(C_1-C_6)$alkylamino, —CF$_3$, —OCF$_3$, or —CN;

$R^4$ is absent, halo, —CN, $(C_1-C_6)$ alkyl, or $(C_1-C_6)$ fluoroalkyl;

wherein D is a heterocyclic or heteroaryl ring selected from the group consisting of:

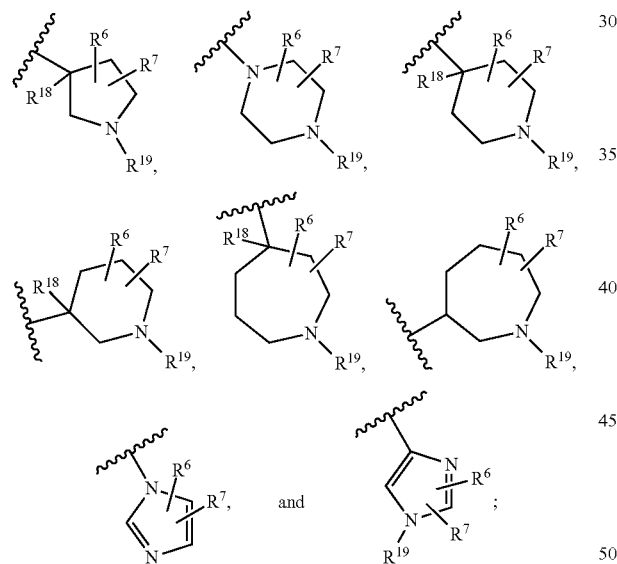

wherein $R^6$ and $R^7$ are independently absent or present, and if present, are independently $(C_1-C_3)$ alkyl, $(C_1-C_3)$ fluoroalkyl, —CH$_2$—O—$(C_1-C_3)$alkyl, —CH$_2$CH$_2$—O—$(C_1-C_3)$alkyl, or —CH$_2$CH$_2$CH$_2$—O—$(C_1-C_3)$alkyl, and wherein $R^6$ and $R^7$ are substituted on a carbon atom;

$R^{18}$ is H, —CN, hydroxy, $(C_1-C_6)$ alkyl, or $(C_1-C_6)$ alkoxy; and $R^{19}$ is H or $(C_1-C_3)$ alkyl.

2. The compound of claim 1, or a pharmaceutically acceptable salt thereof, wherein M is absent.

3. The compound of claim 1, or a pharmaceutically acceptable salt thereof, wherein D is

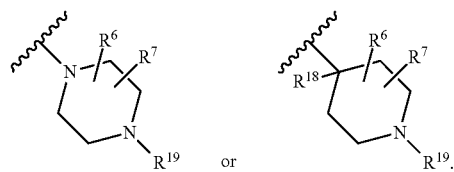

4. The compound of claim 1 having the Formula (Ia):

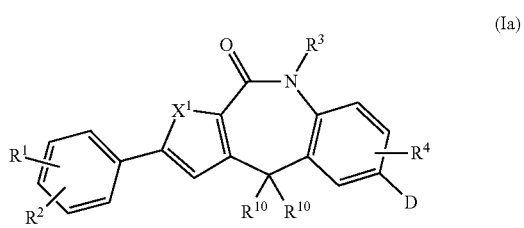

or a pharmaceutically acceptable salt thereof, wherein $R^1$ and $R^2$ are independently absent or present, and if present are independently halo, $(C_1-C_6)$ alkoxy, —CN, $(C_1-C_6)$ haloalkyl, azido, acetyl, propionyl, butanoyl, —S(O)—$(C_1-C_4)$alkyl, or —S(O)$_2$—$(C_1-C_4)$alkyl;

$X^1$ is O or S;

each occurrence of $R^{10}$ is independently H, $(C_1-C_3)$ alkyl, fluoro, $(C_1-C_3)$ fluoroalkyl, or $(C_1-C_3)$ alkoxy;

$R^3$ is H, $(C_1-C_6)$ alkyl, $(C_1-C_6)$ haloalkyl, or $(C_1-C_6)$ alkoxy$(C_1-C_6)$alkyl, or $R^3$ is a group of the formula -J-K, wherein J is $(C_1-C_3)$ alkylene, —C(=O)—, or —C(=S)—;

K is $(C_3-C_{10})$ cycloalkyl, $(C_6-C_{10})$ aryl, 5- to 6-membered heteroaryl, or 5- to 6-membered heterocyclyl, wherein said cycloalkyl, aryl, heteroaryl, or heterocyclyl of K is unsubstituted or substituted with one to four moieties, wherein said moieties are the same or different, and wherein said moieties are selected from the group consisting of $(C_1-C_6)$ alkyl, $(C_1-C_6)$ alkoxy, $(C_1-C_6)$ haloalkyl, halo, amino, $(C_1-C_6)$ alkylamino, di$(C_1-C_6)$alkylamino, —CN, —OCF$_3$, and $R^{25}$;

$R^{25}$ is $(C_6-C_{10})$ aryl or 5- to 6-membered heteroaryl, wherein said aryl or heteroaryl of $R^{25}$ is unsubstituted or substituted with one to four moieties, wherein said moieties are selected from the group consisting of $(C_1-C_6)$ alkyl, hydroxyl, $(C_1-C_6)$ alkoxy, halo, amino, $(C_1-C_6)$ alkylamino, di$(C_1-C_6)$alkylamino, —CF$_3$, —OCF$_3$, and —CN;

each occurrence of $R^{10}$ is independently H, $(C_1-C_3)$ alkyl, fluoro, $(C_1-C_3)$ fluoroalkyl, or $(C_1-C_3)$ alkoxy;

$R^4$ is absent, halo, cyano, $(C_1-C_3)$ alkyl, or $(C_1-C_3)$ fluoroalkyl;

D is a group of the formula:

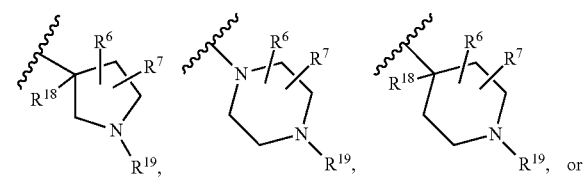

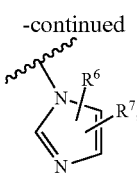

wherein $R^6$ and $R^7$ are independently absent or present, and if present are independently $(C_1-C_3)$ alkyl, $(C_1-C_3)$ fluoroalkyl, —$CH_2$—O—$(C_1-C_3)$alkyl, —$CH_2CH_2$—O—$(C_1-C_3)$ alkyl, —$CH_2CH_2CH_2$—O—$(C_1-C_3)$ alkyl, and wherein $R^6$ and $R^7$ are substituted on a carbon atom;

$R^{18}$ is H, —CN, hydroxy, $(C_1-C_6)$ alkyl, or $(C_1-C_6)$ alkoxy; and $R^{19}$ is H or $(C_1-C_3)$ alkyl.

5. The compound of claim 4 or a pharmaceutically acceptable salt thereof, wherein $R^3$ is -J-K, wherein J is $(C_1-C_3)$ methylene, K is 3- to 6-membered cycloalkyl or phenyl, wherein said cycloalkyl or phenyl of K is unsubstituted or is substituted with one to two moieties, wherein said moieties are the same or different, and wherein said moieties are selected from the group consisting of $(C_1-C_6)$ alkyl, $(C_1-C_6)$ alkoxy, $(C_1-C_6)$ haloalkyl, halo, amino, $(C_1-C_6)$ alkylamino, di$(C_1-C_6)$alkylamino, —CN, —OCF$_3$, and $R^{25}$; and $R^{25}$ is phenyl or 5- to 6-membered heteroaryl, wherein said phenyl or heteroaryl of $R^{25}$ is unsubstituted or substituted with one to four moieties, wherein said moieties are selected from the group consisting of $(C_1-C_6)$ alkyl, hydroxyl, $(C_1-C_6)$ alkoxy, halo, amino, $(C_1-C_6)$ alkylamino, di$(C_1-C_6)$alkylamino, —CF$_3$, —OCF$_3$, and —CN.

6. The compound of claim 5 or a pharmaceutically acceptable salt thereof, wherein $R^{25}$ is pyridyl or pyrimidyl, wherein said pyridyl or pyrimidyl is unsubstituted or substituted with one to four moieties, wherein said moieties are selected from the group consisting of $(C_1-C_6)$ alkyl, hydroxyl, $(C_1-C_6)$ alkoxy, halo, amino, $(C_1-C_6)$ alkylamino, di$(C_1-C_6)$alkylamino, —CF$_3$, —OCF$_3$, and —CN.

7. The compound of claim 4 or a pharmaceutically acceptable salt thereof, wherein D is

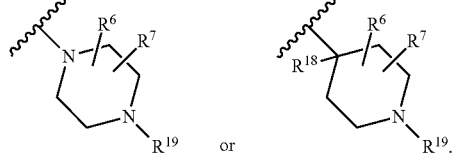

8. The compound of claim 1 having the Formula (Ib):

(Ib)

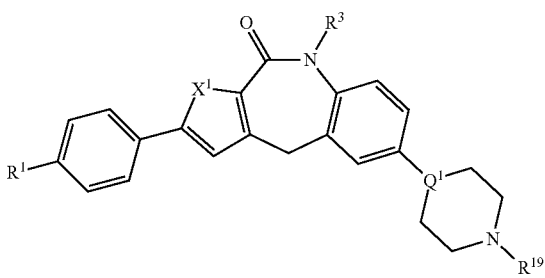

or a pharmaceutically acceptable salt thereof, wherein
$R^1$ is halo or cyano;
$X^1$ is O or S;

$R^3$ is H, $(C_1-C_6)$ alkyl, halo$(C_1-C_6)$alkyl, or $(C_1-C_6)$ alkoxy $(C_1-C_6)$alkyl, or $R^3$ is a group of the formula -J-K,
wherein J is $(C_1-C_3)$ alkylene, —C(=O)—, or —C(=S)—;

K is $(C_3-C_{10})$cycloalkyl, $(C_6-C_{10})$ aryl, 5- to 6-membered heteroaryl, or 5- to 6-membered heterocyclyl, wherein said cycloalkyl, aryl, heteroaryl, or heterocyclyl of K is unsubstituted or substituted with one to four moieties, wherein said moieties are the same or different, and wherein said moieties are selected from the group consisting of $(C_1-C_6)$ alkyl, $(C_1-C_6)$ alkoxy, $(C_1-C_6)$ haloalkyl, halo, amino, $(C_1-C_6)$ alkylamino, di$(C_1-C_6)$alkylamino, —CN, —OCF$_3$, and $R^{25}$;

$R^{25}$ is $(C_6-C_{10})$ aryl or 5- to 6-membered heteroaryl, wherein said aryl or heteroaryl of $R^{25}$ is unsubstituted or substituted with one to four moieties, wherein said moieties are selected from the group consisting of $(C_1-C_6)$ alkyl, hydroxyl, $(C_1-C_6)$ alkoxy, halo, amino, $(C_1-C_6)$ alkylamino, di$(C_1-C_6)$alkylamino, —CF$_3$, —OCF$_3$, or —CN;

$Q^1$ is N or C($R^{18}$);
$R^{18}$ is H, —CN, hydroxy, $(C_1-C_6)$ alkyl, or $(C_1-C_6)$ alkoxy; and
$R^{19}$ is H or $(C_1-C_3)$ alkyl.

9. The compound of claim 8, or a pharmaceutically acceptable salt thereof, wherein $R^3$ is H, methyl, ethyl, propyl, butyl, trifluoromethyl, 2,2,2-trifluoroethyl, 2,2-difluoroethyl, methoxymethyl, ethoxymethyl, propoxymethyl, 2-methoxyethyl, 2-ethoxyethyl, 2-propoxyethyl; or $R^3$ is -J-K, wherein J is methylene, K is 3- to 6-membered cycloalkyl or phenyl, wherein said cycloalkyl or phenyl of K is unsubstituted or is substituted with one to two moieties, wherein said moieties are the same or different, and wherein said moieties are selected from the group consisting of $(C_1-C_6)$ alkyl, $(C_1-C_6)$ alkoxy, $(C_1-C_6)$ haloalkyl, halo, amino, $(C_1-C_6)$ alkylamino, di$(C_1-C_6)$alkylamino, —CN, —OCF$_3$, and $R^{25}$;

$R^{25}$ is phenyl or 5- to 6-membered heteroaryl, wherein said phenyl or heteroaryl of $R^{25}$ is unsubstituted or substituted with one to four moieties, wherein said moieties are selected from the group consisting of $(C_1-C_6)$ alkyl, hydroxyl, $(C_1-C_6)$ alkoxy, halo, amino, $(C_1-C_6)$ alkylamino, di$(C_1-C_6)$alkylamino, —CF$_3$, —OCF$_3$, and —CN.

10. The compound of claim 9, or a pharmaceutically acceptable salt thereof, wherein $R^3$ is H, methyl, 2,2-difluoroethyl, methoxymethyl; or $R^3$ is —$CH_2$—K, wherein K is cyclopropyl, phenyl, or phenyl substituted with one to two moieties, wherein said moieties are the same or different, and wherein said moieties are selected from the group consisting of halo, amino, and $R^{25}$;

wherein $R^{25}$ is phenyl or 5- to 6-membered heteroaryl, wherein said phenyl or heteroaryl of $R^{25}$ is unsubstituted or substituted with one moiety, wherein said moiety is selected from the group consisting of $(C_1-C_6)$ alkoxy and amino.

11. The compound of claim 8 or a pharmaceutically acceptable salt thereof, wherein $Q^1$ is N.

12. The compound of claim 8 or a pharmaceutically acceptable salt thereof, wherein $Q^1$ is C($R^{18}$), wherein $R^{18}$ is H, —CN, hydroxy, $(C_1-C_6)$ alkyl, or $(C_1-C_6)$ alkoxy.

13. The compound of claim 8 or a pharmaceutically acceptable salt thereof, wherein
$R^3$ is H, methyl, 2,2-difluoroethyl, methoxymethyl; or —$CH_2$—K, wherein K is cyclopropyl, phenyl, or phenyl substituted with one to two moieties, wherein said moieties are the same or different, and wherein said moieties are selected from the group consisting of $(C_1-C_6)$ alkyl, $(C_1-C_6)$ alkoxy, $(C_1-C_6)$ haloalkyl, halo, —CN, —OCF$_3$, and $R^{25}$;

$R^{25}$ is phenyl, pyridyl, or pyrimidyl, wherein said phenyl, pyridyl, or pyrimidyl of $R^{25}$ is unsubstituted or substituted with one moiety, wherein said moiety is selected from the group consisting of $(C_1-C_6)$ alkoxy or amino;

$Q^1$ is N or C(H); and $R^{19}$ is H or methyl.

14. The compound of claim 1, or a pharmaceutically acceptable salt thereof, wherein the compound is selected from one of the following compounds:

1
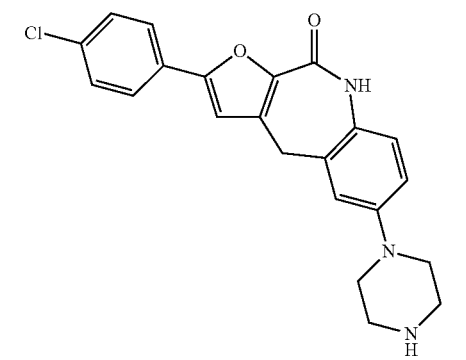

2
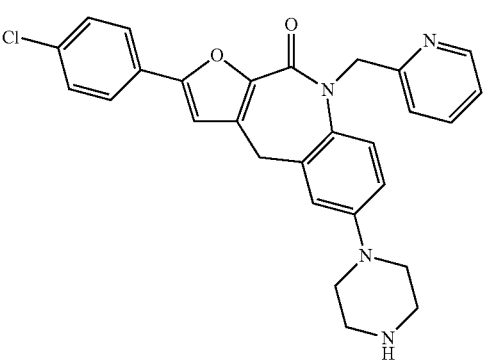

3
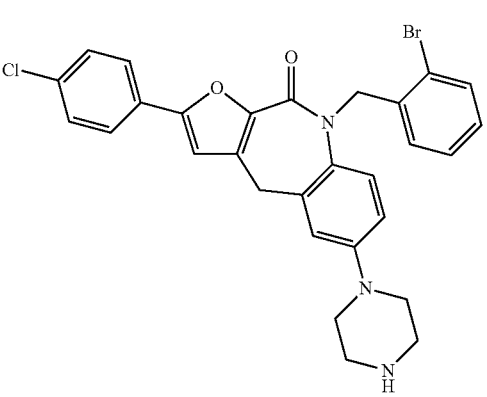

4
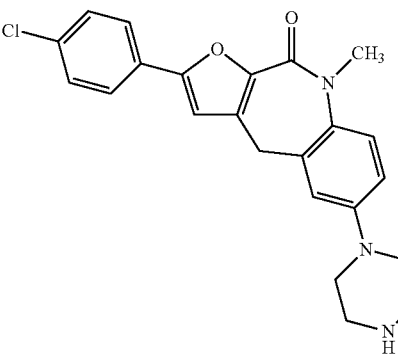

5
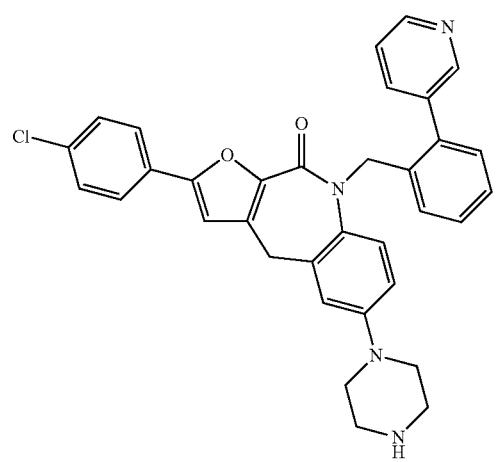

6
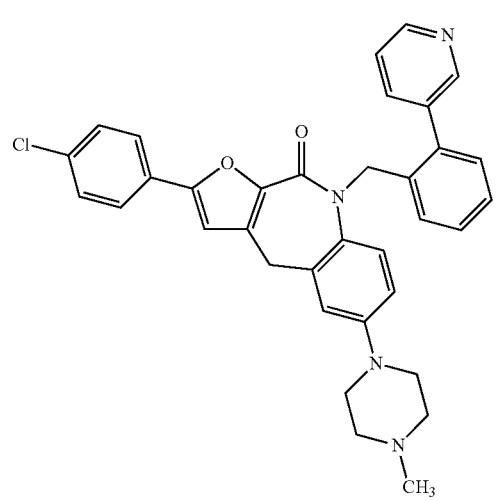

7
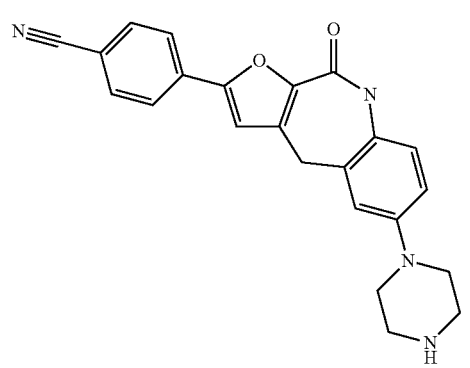

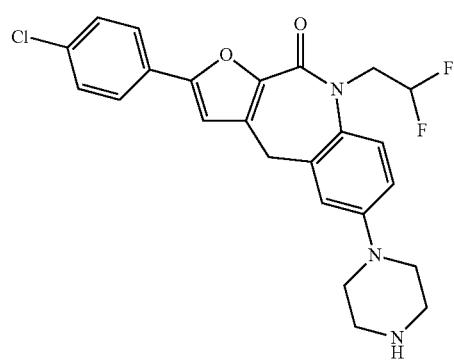
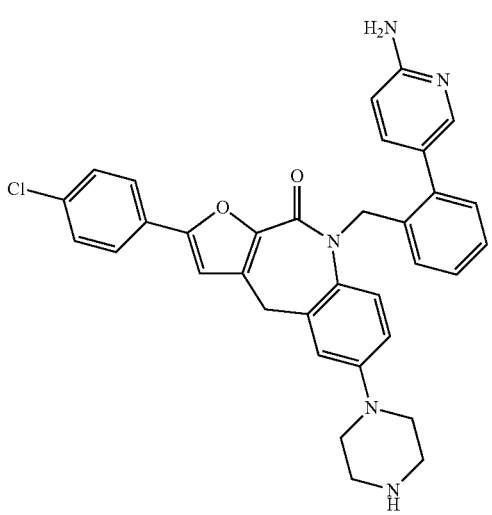
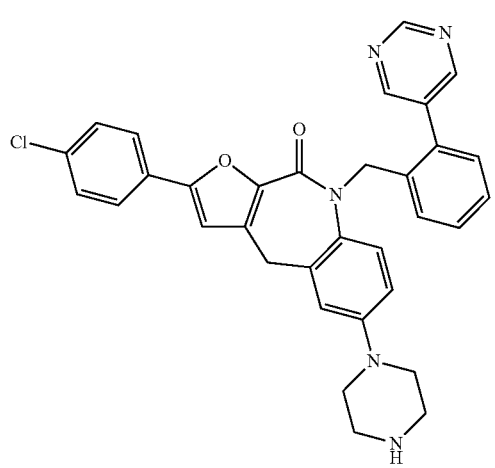
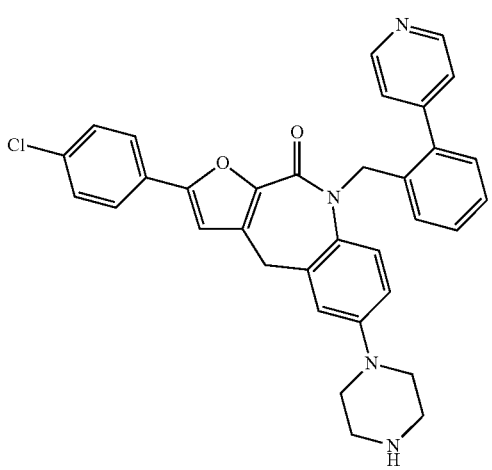
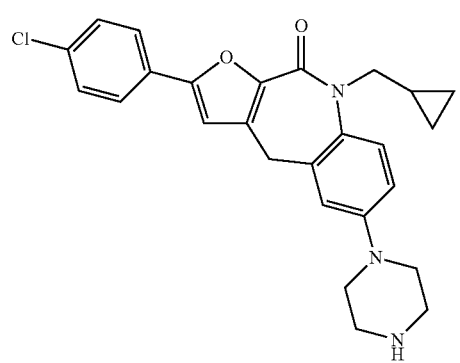
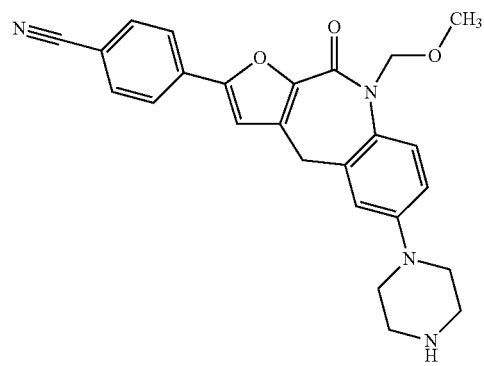

85
-continued
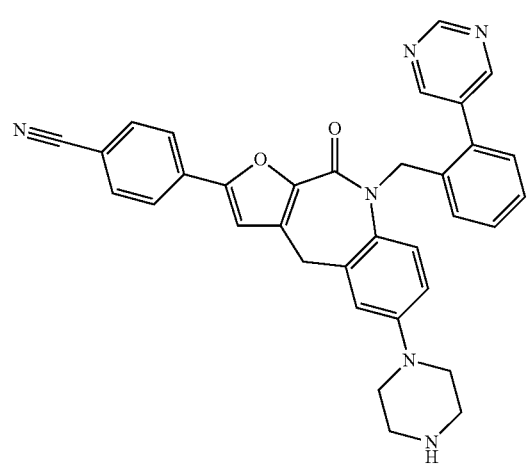
14
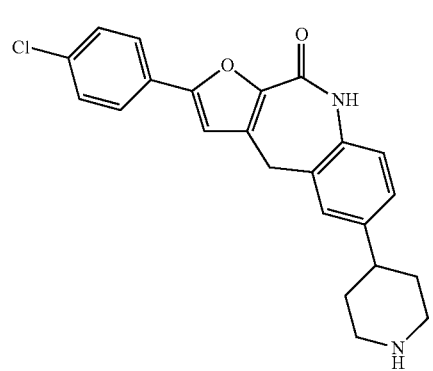
15
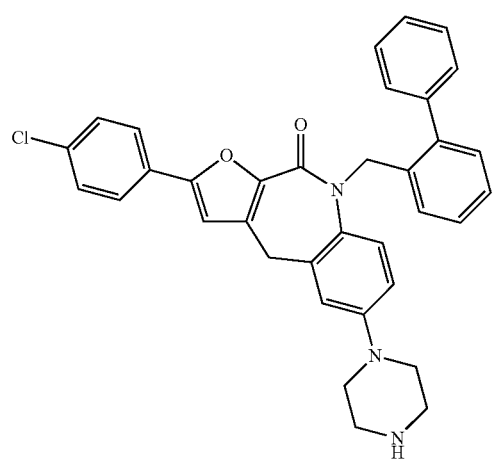
16
86
-continued
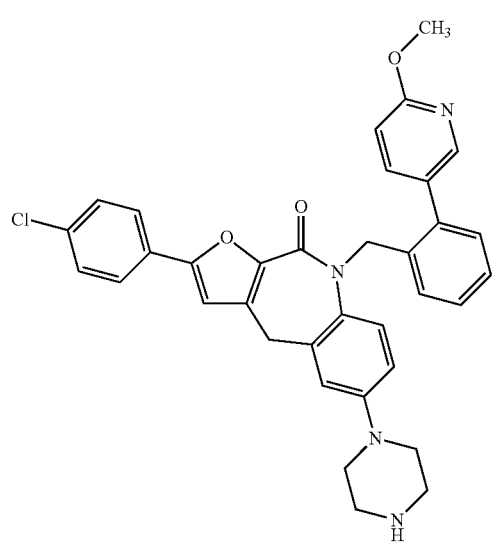
17
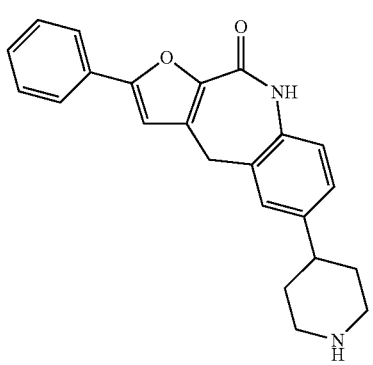
18
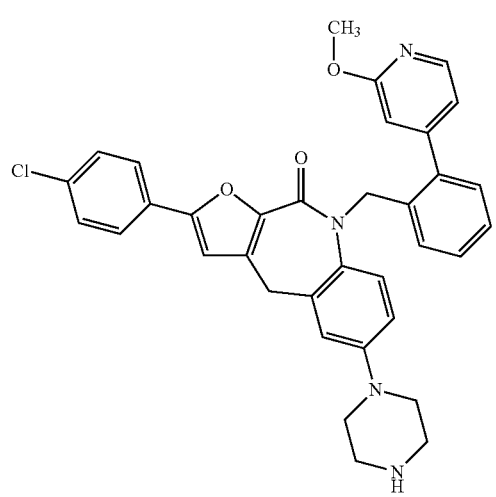
19

87
-continued
20
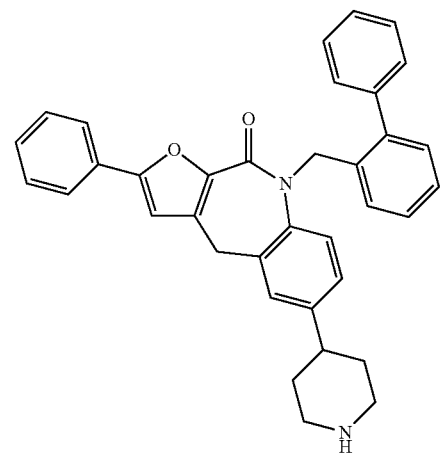
21
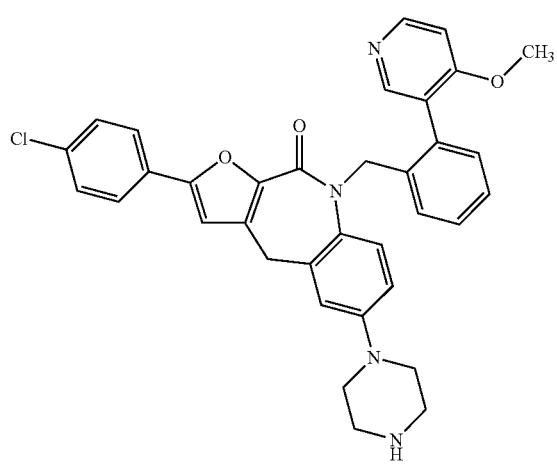
22
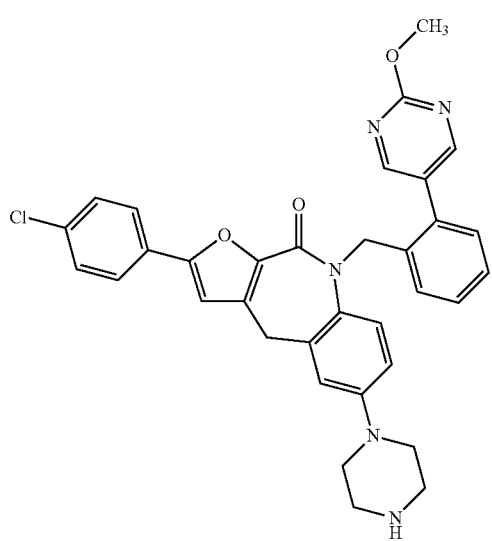
88
-continued
23
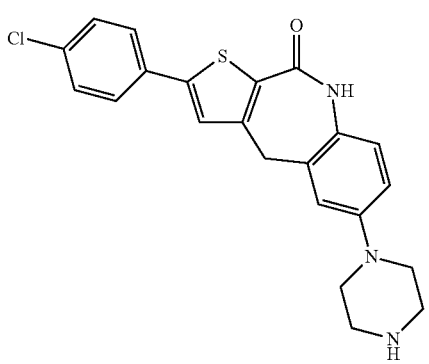
24
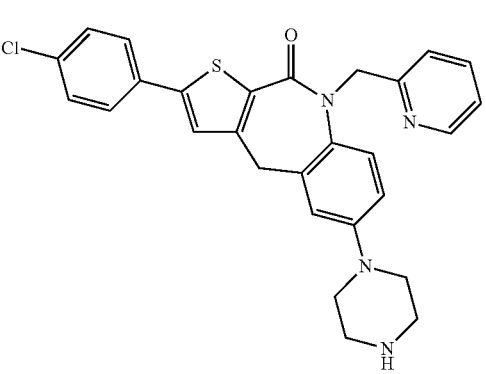
25
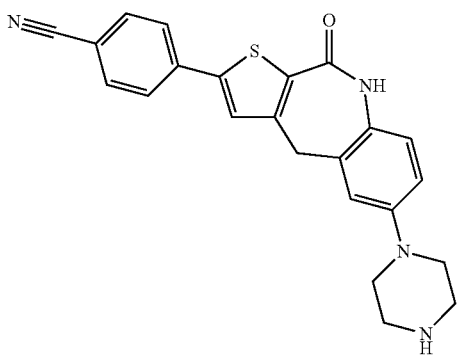
26
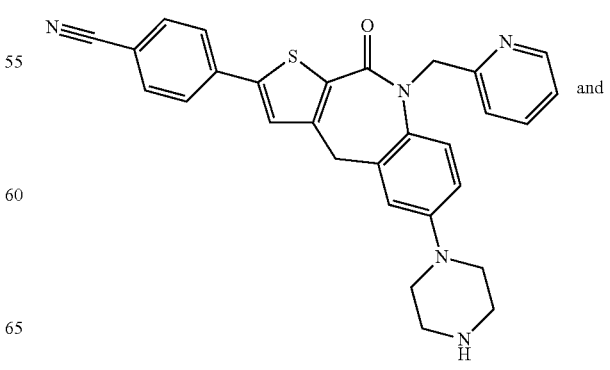
and

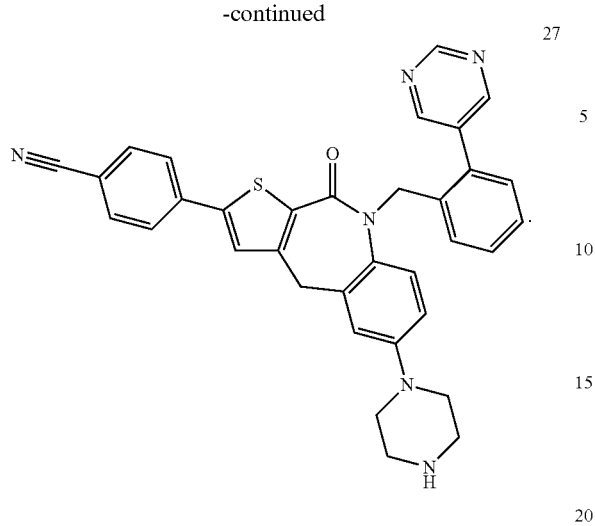

15. A pharmaceutical composition, comprising a therapeutically effective amount of the compound of claim 1, or a pharmaceutically acceptable salt thereof, and a pharmaceutically acceptable carrier.

16. A method of treating an inflammatory disorder selected from the group consisting of rheumatoid arthritis, inflammatory bowel disease, psoriasis, asthma, and chronic obstructive pulmonary disorder, comprising administering a therapeutically effective amount of a compound of claim 1, or a pharmaceutically acceptable salt thereof, to a patient in need of such treatment.

* * * * *